(12) United States Patent  
Middelberg et al.

(10) Patent No.: US 8,039,582 B2
(45) Date of Patent: Oct. 18, 2011

(54) PEPTIDE NETWORKS

(75) Inventors: Anton Peter Jacob Middelberg, Brookfield (AU); Annette Faith Dexter, Toowong (AU)

(73) Assignee: The University of Queensland, St. Lucia, Queensland (AU)

( * ) Notice: Subject to any disclaimer, the term of this patent is extended or adjusted under 35 U.S.C. 154(b) by 877 days.

(21) Appl. No.: 11/817,144

(22) PCT Filed: Feb. 24, 2006

(86) PCT No.: PCT/AU2006/000236
§ 371 (c)(1),
(2), (4) Date: Nov. 1, 2007

(87) PCT Pub. No.: WO2006/089364
PCT Pub. Date: Aug. 31, 2006

(65) Prior Publication Data
US 2010/0152420 A1   Jun. 17, 2010

(30) Foreign Application Priority Data

Feb. 24, 2005  (AU) .............................. 2005900853
Jul. 8, 2005    (AU) .............................. 2005903643
Sep. 27, 2005   (AU) .............................. 2005905323

(51) Int. Cl.
*A61K 38/00* (2006.01)
*A61K 38/04* (2006.01)
*A61K 51/00* (2006.01)
*C07K 5/00* (2006.01)
*C07K 7/00* (2006.01)
*C07K 16/00* (2006.01)
*C07K 17/00* (2006.01)
*A61L 9/01* (2006.01)

(52) U.S. Cl. ......... 530/326; 530/300; 514/1.1; 514/945; 424/1.69; 435/266

(58) Field of Classification Search ........................ None
See application file for complete search history.

(56) References Cited

FOREIGN PATENT DOCUMENTS
WO    WO 01/74864 A1   10/2001

OTHER PUBLICATIONS

Dexter, A.F. et al. 2006 "Reversible active switching of the mechanical properties of a peptide film at a fluid-fluid interface" *Nature Materials* 5(6):502-506.
Morreale, G. et al. 2004 "Bioprocess-centered molecular design (BMD) for the efficient production of an interfacially active peptide" *Biotechnology and Bioengineering* 87(7):912-923.
Supplemental European Search Report for European Application No. EP 06704911, (2008).
Andrews, M.J.I. and Tabor, A.B. 1999. "Forming Stable Helical Peptides Using Natural and Artificial Amino Acis" *Tetrahedron* 55: 11711-11743.
Ariga, et al. 2005 "Turnable pK of Amino Acid Residues at the Air-Water Interface Gives an L-zyme (Langmuir Enzyme)", *J. Am. Chem. Soc.* 127: 12074-12080.
Arndt, K.M. et al. 2000 "A Heterodimeric Coiled-coil Peptide Pair Selected in Vivo from a Designed Library-versus-library ensemble" *J. Mol Biol* 295: 627-639.
Arndt, K.M. et al. 2002 "Comparison of in Vivo Selection and Rational Design of Heterodimeric Coiled Coils" *Sturcture* 10: 1235-1248.
Benhar, I. 2001 "Biotechnological Applications of Phage and Cell Display" *Biotechnol Adv.* 19: 1-33.
Boon, C.L. et al. 2004 "Identification of Stable Heliclal Bundles from a Combinatorial Library of Amphipathic Peptides" *Biopolymers Pept Sci* 76: 244-257.
Bosshard, H.R. et al. 2004 "Protein Stabilization by Salt Brdges: Concepts, Experimental Approaches and Clarification of Some Misunderstandings" *J. Mol Recognit* 17: 1-16.
Caessens, P. et al. 1999 "Beta-lactoglobulin Hydrolysis. 1. Peptide Composition and Functional Properties of Hydrolysates Obtained by the Action of Plasmin, Trypsin, and Staphylococcus Aureus V8 Protease" *J. Agric. Food Chem.*, 47: 2973-2979.
Caessens, P. et al. 1999 "Beta-lactoglobulin hydrolysis. 2. Peptide identification, SH/SS Exchange, and Functional Properties of Hydrolysate Fractions Formed by the Action of Plasmin" *J. Agric. Food Chem.*, 47: 2980-2990.
Cameron, D.R., et al. 1991 "Determination of Interfacial Areas in Emulsions Using Turbidimetric and Droplet Size Data: Correction of the Formula for Emulsifying Activity Index" *J. Agric. Food Chem.*, 39: 655-659.
Cascao-Pereira, L.G., et al: 2003 "Dilatational Rheology of BSA Conformers at the Air/Water Interface" *Langmuir* 19: 2349-2356.
Cascao-Pereira, L.G., et al. 2003 "Interfacial Versus Homogeneous Enzymatic Cleavage of Mandelon" *Biotechnology Bioeng* 83:498-501.
Cascao-Pereira, L.G., et al. 2003 "Surface Forces and Drainage Kinetics of Protein-Stabilized Aqueous Films" *Langmuir* 19: 7503-7513.
Cho, S.J. et al. 1998 "Rational Combinatorial Library Design. 2. A Rational Design of Targeted Combinatorial Peptide Libraries Using Chemical Similarity Probe and the Inverse QSAR Approaches" *J. Chem Inf. Comput. Sci.*, 38: 259-268.
Cochran, D.A.E. et al. 2001 "Effect of the N1 Residue on the Stability of the Alpha-helix for All 20 Amino Acids" *Protein Sci.* 10: 463-470.
Cochran, D.A.E. et al. 2001 "Effect of the N2 Residue on the Stability of the Alpha-helix for All 20 Amino Acids" *Protein Sci.* 10: 1305-1311.
Cohen, C. and Parry, D.A.D. 1990 "α-Helical Coiled Coils and Bundles: How to Design an α-Helical Protein" *Proteins: Struct., Funct., Genet* 7: 1-15.

(Continued)

*Primary Examiner* — Maury Audet
(74) *Attorney, Agent, or Firm* — Knobbe, Martens, Olson & Bear, LLP

(57) ABSTRACT

Methods of modulating interfacial characteristics in a self-assembled, force-transmitting peptide network at a fluid-fluid interface are disclosed. The methods involve exposing a peptide capable of participating in a self-assembled, force-transmitting peptide network, either before or after it interacts with other peptides to form the peptide network to a stimulus that alters the chemical and/or physical properties of the peptide. Use of such methods in applications such as emulsions and foams are also disclosed.

31 Claims, 7 Drawing Sheets

OTHER PUBLICATIONS

De Alba, E. et al. 1999 "De Novo Design of a Monomeric Three-stranded antiparallel beta-sheet" *Protein Sci.*, 8: 854-865.

De Crescenzo, G. et al. 2003 "Real-time Monitoring of the Interactions of Two-stranded de Novo Designed Coiled-coils: Effect of Chain Length on the Kinetic and Thermodynamic Constants of Binding" *Biochemistry* 42: 1754-1763.

De Vocht, M.L. et al. 1998 "Structural Characterization of the Hydrophobin SC3, as a Monomer and After Self-Assembly at Hydrophobic/Hydrophilic Interfaces" *Biophysical Journal* 74:2059-2068.

Degrado, W.F. 2001 "Introduction: Protein Design" *Chem. Rev.* 101: 3025-3026.

Degrado, W.F. et al. 1999 "The Twists and Turns of Beta-peptides" *J. Pept Res.*, 54: 206-217.

Degrado, W.F. Summa et al. 1999 "De Novo Design and Structural Characterization of Proteins and Metalloproteins" *Annu Rev Biochem* 68: 779-819.

Dickinson E. Murray, B.S. and Stainsby, G. 1988 "Coalescence Stability of Emulsion Sized Droplets at a Planar Oil-Water Interface and the Relationship to Protein Film Surface Rheologly" *J. Chem. Soc., Faraday Trans.* 1 84: 871-883.

Faergemand, M. Murray B.S. and Dickinson, E. 1997 "Cross-linking of Milk Proteins with Transglutaminase at the Oil-water Interface" *J. Agric. Food Chem* 45: 2514-2519.

Fairman, R. et al. 1995 "Characterization of a new four-chain coiled-coil: Influence of chain length on Stability" *Protein Science* 4:1457-1469.

Fairman, R. et al. 1996 "Design of Heterotetrameric Coiled Coils: Evidence for Increased Stabilization by Glu(−)-Lys(+) ion Pair Interactions" *Biochemistry* 35: 2824-2829.

Fung, S.Y. et al. 2003 "Concentration Effect on the Aggregation of a Self-assembling Oligopeptide" *Biophys J.* 85: 537-548.

Gauthier, S.F. et al.1993 "Surface Activity and Related Functional Properties of Peptides Obtained from Whey Proteins" *J Dairy Sci* 76:321-328.

Girardet, J.M. et al. 2000 "Viscoelastic Properties of Oil-water Interfaces Covered by Bovine Beta-casein Tryptic Peptides" *J Diary Sci* 83: 2410-2421.

Hill, R.B. et al. 2000 "De Novo Design of Helical Bundles as Models for Understanding Protein Folding and Functions" *Acc. Chem Res.*, 33: 745-754.

Hong, Y. et al. 2003 "Effect of Amino Acid Sequence and pH on Nanofiber Formation of Self-Assembling Peptides EAK 16-II and EAK 16-IV" *Biomacromolecules* 4:1433-1442.

Huang, X.L. et al. 1996 "Improved Emulsifying Properties of β-Barrel Domain Peptides Obtained by Membrane-Fractionation of a Limited Tryptic Hydrolysate of β-Lactoglobulin" *J Agric Food Chem* 44:3437-3443.

Huyghues Despointes, B.M.P. and Baldwin, R.L. 1997 "Ion-pair and Charged Hydrogen-bond Interactions Between Histidine and Asparate in a Peptide Helix" *Biochemistry* 36: 1965-1970.

Jelesarov, I. et al. 1998 "Salt Effects on Hydrophobic Interaction and Charge Screening in the Folding of a Negatively Charged Peptide to a Coiled Coil (leucine zipper)" *Biochemistry*, 37: 7539-7550.

Jones, D.B. and Middleberg, A.P.J. 2002 "Direct determination of the mechanical properties of an interfacially adsorbed protein film" *Chemical Engineering Science* 57:1711-1722.

Jones, D.B. and Middleberg, A.P.J. 2002 "Mechanical Properties of Interfacially Adsorbed Peptide Networks" *Langmuir* 18:10357-10362.

Jones, D.B. and Middleberg, A.P.J. 2002 "Micromechanical Testing of Interfacial Protein Networks Demonstrates Ensemble Behavior Characteristic of a Nanostructured Biomaterial" *Langmuir* 18:5585-5591.

Jones, D.B. and Middleberg, A.P.J. 2003 "Interfacial Protein Networks and Their Impact on Droplet Breakup" *American Institute of Chemical Engineers (AIChE) Journal* 49:1533-1541.

Kerth, A. et al. 2004 "Infrared Reflection Absorption Spectroscopy of Amphipathic Model Peptides at the Air/Water Interface" *Biophys J.* 86: 3750-3758.

Kohn, W.D. and Hodges, R.S. 1998 "De Novo Design of α-helical Coiled Coils and Bundles: Models for the Development of Protein-Design Principles" *Trends Biotechnol.* 16: 379-389.

Kohn, W.D. et al. 1995 "The Effects of Interhelical Electrostatic Repulsions Between Glutamic-Acid Residues in Controlling the Dimerization and Stability of 2-Stranded Alpha-Helical Coiled-Coils" *J. Biol. Chem* 270: 25495-25506.

Kohn, W.D. et al. 1997 "Positional Dependence of the Effects of Negatively Charged Glu Side Chains on the Stability of Two-stranded Alpha-helical Coiled-coils" *J. Pept Sci.* 3: 209-223.

Kohn, W.D. et al. 1997 "Salt Effects on Protein Stability: Two-stranded Alpha-helical Coiled-coils Containing Inter- or Intrahelical Ion Pairs" *J. Mol. Biol* 267: 1039-1052.

Krylov, D. et al. 1998 "Inter-helical Interactions in the Leucine Zipper Coiled Coil Dimer: pH and Salt Dependence of Coupling Energy Between Charged Amino Acids" *J Mol Biol* 279: 959-972.

Kwok, S.C. and Hodges, R.S. 2004 "Effects of Chain Length on Coiled-Coil Stability: Decreasing Stability with Increasing Chain Length" *Biopolymers* 76: 378-390.

Litowski, J.R. and Hodges, R.S. 2001 "Designing Hetrodimeric Two-stranded Alpha-helical Coiled-coils: The Effect of Chain Length on Protein Folding, Stability and Specificity" *J Pept Res* 58: 477-492.

Litowski, J.R. and Hodges, R.S. 2002 "Designing Heterodimeric Two-stranded Alpha-helical Coiled-coils—Effects of Hydrophobicity and Alpha-helical Propensity on Protein Folding, Stability, and Specificity" *J Biol Chem* 277: 37272-37279.

Luck, P.J. et al. 2001 "Factors Determining Yield Stress and Overrun of Whey Protein Foams" *Journal of Food Science* 67:1677-1681.

Marti, D.N. and Bosshard, H.R. 2003 "Electrostatic Interactions in Leucine Zippers: Thermodynamic Analysis of the Contributions of Glu and His Residues and the Effect of Mutating Salt Bridges" *J. Mol Biol* 330: 621-637.

Martin, A.H. et al. 2002 "Network Forming Properties of Various Proteins Adsorbed at the Air/Water Interface in Relation to Foam Stability" *Journal of Colloid and Interface Science* 254:175-183.

Middelberg, A.P.J. et al. 2000 "Peptide interfacial adsorption is kinetically limited by the thermodynamic stability of self association" *Proc Natl Acad Sci USA* 97:5054-5059.

Mohammed, R.A. et al. 1993 "Dewatering of Crude-oil Emulsions 1. Rheological Behavior of the Crude-Oil Water Interface" *Colloids and Surfaces A: Physicochemical and Eng Aspects* 80: 223-235.

Morris, V.J. et al. 2000 "Surfactant-Protein Interactions at Air-Water and Oil-Water Interfaces Observed by Atomic Force Microscopy" *Special Publication—Royal Society of Chemistry (Gums and Stabilizers for the Food industry 10)* 251:328-336.

Mucha, M. et al. 2005 "Unified Molecular Picture of the Surfaces of Aqueous Acid, Base and Salt Solutions" *J. Phys. Chem. B.* 109: 7617-7623.

Rahali, V. et al. 2000 "Emulsification of chemical and enzymatic hydrolysates of β-lactoglobulin: characterization of the peptides adsorbed at the interface" *Nahrung* 44:89-95.

Rapaport, H. et al. 2000 "Two-dimensional Order in Beta-Sheet Peptide Monolayers" *J. Am. Chem. Soc.*, 122: 12523-12529.

Rapaport, H. et al. 2002 "Assembly of Triple-Strained Beta-Sheet Peptides at Interfaces" *J. Am. Chem. Soc.* 124: 9342-9343.

Rausch, J.M. et al. 2005 "Rational Combinatorial Design of Pore-forming Beta-Sheet Peptides" *Proc. Natl. Acad. Sci. USA* 102: 10511-10515.

Regan, L. 1995 "Protein Design—Novel Metal-Binding Sites" *Trends Biochem Sci*, 20: 280-285.

Roth, S. et al. 2000 "Interfacial Shear Rheology of Aged and Heat-Treated β-Lactoglobulin Films: Displacement by Nonionic Surfactant" *J Agric Food Chem* 48:1491-1497.

Sarikaya, M. et al. 2004 "Materials Assembly and Formation Using Engineered Polypeptides" *Annu. Rev. Mater. Res.* 34: 373-408.

Sneer, R. et al. 2004 "Parallel Beta-Sheet Assemblies at Interfaces" *ChemPhysChem* 5: 747-750.

Su, J.Y. et al. 1994 "Effect of Chain-Length on the Formation and Stability of Synthetic Alpha-Helical Coiled-Coils" *Biochemistry* 33: 15501-15510.

Tamerler, C. et al. 2003 "Biomimetic Multifunctional Molecular Coatings Using Engineered Proteins" *Prog. Org. Coat* 47: 267-274.

Van Der Ven, C. et al. 2001 "Emulsion Properties of Casein and Whey Protein Hydrolysates and the Relation with Other Hydrolysate Characteristics" *J Agric Food Chem* 49:5005-5012.

Van Der Ven, C. et al. 2002 "Correlations between Biochemical Characteristics and Foam-Forming and Stabilizing Ability of Whey and Casein Hydrolysates" *J Agric Food Chem* 50:2938-2946.

Vu, C. et al. 2001 "Effects of Charged Amino Acids at b and c Heptad Positions on Specificity and Stability of Four-Chain Coiled Coils" *Protein Sci.* 10: 631-637.

Wang, K. et al. 2005 "Effects of the Sequence and Size of Non-Polar Residues on Self-Assembly of Amphiphilic Peptides" *Int J. Biol Macromol* 36: 232-240.

Wang, T. et al. 2004 "Length Dependent Helix-Coil Transition Kinetics of Nine Alanine-Based Peptides" *J. Phys. Chem. B.* 108: 15301-15310.

Wang, X. et al. 2004 "Probing the Self-Assembly and the Accompanying Structural Changes of Hydrophobin SC3 on a Hydrophobic Surface by Mass Spectrometry" *Biophysical Journal* 87:1919-1928.

Wilde, P.J. et al. 2003 "Interfacial Mechanisms Underlying Lipid Damage of Beer Foam" *Special Publication—Royal Society of Chemistry (Gums and Stabilizers for the Food industry)* 254:200-206.

Williams, A. et al. 1997 "Behaviour of Droplets in Simple Shear Flow in the Presence of a Protein Emulsifier" *Colloids and Surfaces A: Physicochemical and Eng Aspects* 125: 189-200.

Xu, G.F. et al. 2001 "Self-Assembled Monolayers from a Designed Combinatorial Library of De Novo Beta-Sheet Proteins" *Proc. Natl. Acad. Sci. USA* 98: 3652-3657.

Xu, Z., et al. 2004 "Orientation of Peptides in Aqueous Monolayer Films Infrared Reflection-Absorption Spectroscopy Studies of a Synthetic Amphipathic Beta-Sheet" *Langmuir* 20: 3730-3733.

Yu, Y. et al. 1996 "Ion Pairs Significantly Stabilize Coiled-Coils in the Absence of Electrolyte" *J. Mol. Biol.*, 255: 367-372.

Zhang, S. and Altman, M.1999 "Peptide Self-Assembly in Functional Polymer Science and Engineering" *Reactive & Functional Polymers* 41:91-102.

A

B

```
SEQUENCE LISTING

<160> NUMBER OF SEQ ID NOS: 15

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Met Lys Gln Leu Ala Asp Ser Leu Met Gln Leu Ala Arg Gln Val Ser
1               5                   10                  15

Arg Leu Glu Ser Ala
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Met Lys Gln Leu Ala Asp Ser Leu His Gln Leu Ala Arg Gln Val Ser
1               5                   10                  15

Arg Leu Glu His Ala
            20

<210> SEQ ID NO 3
<211> LENGTH: 28
<212> TYPE: PRT
<213> ORGANISM: Artificial Sequence
<220> FEATURE:
<223> OTHER INFORMATION: Synthetic peptide

<400> SEQUENCE: 3

Leu Met Gln Leu Ala Arg Gln Met Lys Gln Leu Ala Asp Ser Leu Met
1               5                   10                  15

Gln Leu Ala Arg Gln Val Ser Arg Leu Glu Ser Ala
            20                  25

<210> SEQ ID NO 4
<211> LENGTH: 21
<212> TYPE: PRT
<213> ORGANISM: Artificial Sequence
<220> FEATURE:
<223> OTHER INFORMATION: Synthetic peptide

<400> SEQUENCE: 4
```

```
Met Lys Glu Leu Ala Asp Ser Leu Met Gln Leu Ala Arg Gln Val Asp
1               5                   10                  15

Arg Leu Glu Ser Ala
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic peptide

<400> SEQUENCE: 5

Met Lys Gln Leu Ala Asp Ser Leu His Gln Leu Ala His Gln Val Ser
1               5                   10                  15

His Leu Glu His Ala
            20

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Pro His Phe Arg Phe Ser Phe Ser Pro
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Pro His Phe Ser Phe Ser Phe Ser Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Pro Ser Phe Arg Phe Ser Phe Ser Pro
1               5

<210> SEQ ID NO 9
<211> LENGTH: 21
<212> TYPE: PRT
<213> ORGANISM: Artificial Sequence
<220> FEATURE:
<223> OTHER INFORMATION: Synthetic peptide

<400> SEQUENCE: 9

Met Glu Glu Leu Ala Asp Ser Leu Glu Glu Leu Ala Arg Gln Val Glu
1               5                   10                  15

Glu Leu Glu Ser Ala
            20

<210> SEQ ID NO 10
<211> LENGTH: 21
```

```
<212> TYPE: PRT
<213> ORGANISM: Artificial Sequence
<220> FEATURE:
<223> OTHER INFORMATION: Synthetic peptide

<400> SEQUENCE: 10

Met Lys Lys Leu Ala Asp Ser Leu Lys Lys Leu Ala Arg Gln Val Lys
1               5                   10                  15

Lys Leu Glu Ser Ala
            20

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Pro His Phe His Phe Ser Phe Ser Pro
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Pro His Phe Ser Phe His Phe Ser Pro
1               5

<210> SEQ ID NO 13
<211> LENGTH: 21
<212> TYPE: PRT
<213> ORGANISM: Artificial Sequence
<220> FEATURE:
<223> OTHER INFORMATION: Synthetic peptide

<400> SEQUENCE: 13

Met Lys Gln Leu Ala Asp Ser Leu His Gln Leu Ala His Lys Val Ser
1               5                   10                  15

His Leu Glu His Ala
            20

<210> SEQ ID NO 14
<211> LENGTH: 21
<212> TYPE: PRT
<213> ORGANISM: Artificial Sequence
<220> FEATURE:
<223> OTHER INFORMATION: Synthetic peptide

<400> SEQUENCE: 14

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 15
<211> LENGTH: 21
<212> TYPE: PRT
<213> ORGANISM: Artificial Sequence
<220> FEATURE:
<223> OTHER INFORMATION: Synthetic peptide

<400> SEQUENCE: 15
```

Lys Ile Ser Ala Leu Lys Glu Lys Ile Ser Ala Leu Lys Glu Lys Ile
1               5                   10                  15

Ser Ala Leu Lys Glu
        20

PEPTIDE NETWORKS

This application is U.S. National Phase of International Application PCT/AU2006/000236, filed Feb. 24, 2006 designating the U.S., and published in English as WO 2006/089364 on Aug. 31, 2006, which claims priority to Australian Patent Application No. 2005900853 filed Feb. 24, 2005, Australian Patent Application No. 2005903643 filed Jul. 8, 2005, and Australian Patent Application No. 2005905323 filed Sep. 27, 2005.

FIELD OF THE INVENTION

The invention generally relates to methods of modulating physical characteristics of self-assembled, peptide ensembles located at a fluid-fluid interface, in order to modify specific interfacial characteristics, in particular the modulation of self-assembled, force-transmitting peptide networks capable of stimuli-responsive modulation of interfacial characteristics and their use in applications such as emulsions, foams, coatings and drug delivery. More particularly, the invention relates to methods of modulating interfacial characteristics in self-assembled, force-transmitting peptide networks at a fluid-fluid interface by exposing the peptide and/or peptide network to a stimulus that alters the chemical and/or physical properties of the peptides in the peptide network.

BACKGROUND OF THE INVENTION

The adsorption of polypeptides and proteins at fluid-fluid interfaces is fundamental to a number of industrial applications ranging from food processing (Faergemand et al., 1997 and references cited therein) and biphasic catalysis (Cascao-Pereira et al., 2003a) to oil recovery (Mohammed et al., 1993). Adsorbed protein layers confer mechanical strength to fluid interfaces, thus altering their properties. In oil-water emulsions, the presence of a protein layer having mechanical strength affects both the ease of initial droplet disruption (Williams et al., 1997) and subsequent emulsion stability during storage (Dickinson et al., 1988). Similarly, in foams, the presence of an interfacial protein layer possessing mechanical strength increases foam stability in the medium to long term (Cascao-Pereira et al., 2003b, Cascao-Pereira et al., 2003c).

The viscoelasticity of a protein layer adsorbed at a fluid-fluid interface can be determined directly (Jones and Middelberg, 2002a, Jones and Middelberg, 2002c) and the presence of a protein layer capable of transmitting force in the interface predicts emulsion stability under conditions where predictions based on interfacial tension fail (Jones and Middelberg, 2003). Furthermore, the ability to transmit force in a fluid interface is not an exclusive property of proteins, but short (11-25 residue) peptides can also form force-transmitting networks at fluid-fluid interfaces (Jones and Middelberg, 2002b). Like proteins, such peptides self-locate to a fluid interface from bulk solution and may form nanostructured networks with defined mechanical properties. Such peptide networks may be useful in the formation of emulsions and foams and could also be useful in coatings or in the formation of drug delivery agents.

However, in a number of situations, stabilization of a fluid-fluid interface, such as formation of a stable emulsion, foam, coating or drug delivery agent may be required for a particular reason but subsequent stabilization of the interface is not required. Alternatively, there may be a requirement to delay formation of a stabilized fluid-fluid interface, thereby delaying formation of a stable emulsion, foam, coating or drug delivery agent. In other applications there may be a requirement to stabilize and destabilize a fluid-fluid interface, for example in an emulsion, foam, coating or drug delivery agent, a plurality of times. An emulsion may be destabilized by the addition of a demulsifier and a foam may be destabilized by the addition of a defoamer. However, the use of traditional demulsifiers and defoamers can be expensive and impose additional complexity and cost on a method. Furthermore, once added, a traditional demulsifier or defoamer causes the breakdown of an emulsion or foam or prevents an emulsion or foam forming but its effects may be difficult to reverse or remove after addition as the chemical composition of the interface is altered by the addition of agents that compete for interfacial space. There is a need for a method which allows modulation of the stabilization of a fluid-fluid interface, such as in an emulsion, foam, coating or drug delivery agent, to allow control of formation, dissipation and the strength or stability of the emulsion, foam, coating or drug delivery agent formed.

The present inventors have now found that interfacial characteristics, such as force transmission, of a self-assembled, force-transmitting peptide network may be modulated allowing the properties of a fluid-fluid interface, such as in an emulsion, foam, coating or drug delivery agent, formed with the peptide network to be manipulated in a predictable manner thus allowing the peptide networks to be formed and dissipated in response to particular stimuli or allowing the strength and/or elasticity and/or rate of formation of the peptide network to be manipulated by a particular stimulus.

SUMMARY OF THE INVENTION

The present invention is predicated in part on the determination that stimuli which alter the chemical and/or physical properties of a peptide modulate the interfacial characteristics, such as force transmission, of a self-assembled, force-transmitting peptide network such that the strength of the network may be enhanced or reduced or the peptide interactions within the network may be entirely dissipated in a predictable manner.

Accordingly, in one aspect of the present invention there is provided a method of modulating interfacial characteristics in a self-assembled, force-transmitting peptide network at a fluid-fluid interface comprising exposing a peptide capable of participating in a self-assembled, force-transmitting peptide network, either before or after it interacts with other peptides to form the peptide network, to a stimulus that alters the chemical and/or physical properties of the peptide. In some embodiments, the interfacial characteristic that is modulated is the ability of the peptide network to transmit force. In some embodiments, modulation provides a switch such that under one set of conditions, a stable peptide network forms and under a second set of conditions the peptide network is unable to form or its ability to transmit force entirely dissipates.

In another aspect of the present invention there is provided a method of modulating interfacial characteristics in a self-assembled, force-transmitting peptide network at a fluid-fluid interface comprising the steps of:
  i) at a first time, exposing a peptide capable of participating in a self-assembled, force-transmitting peptide network, either before or after it interacts with other peptides to form the peptide network, to a first stimulus that alters the chemical and/or physical properties of the peptide; and ii) at a second time, exposing the peptide to a second stimulus that alters the chemical and/or physical properties of the peptide adopted upon exposure to the first stimulus.

In some embodiments, the interfacial property that is modulated is the ability of the peptide network to transmit force. In some embodiments, the first stimulus causes the formation of a peptide network and the second stimulus causes a reduction in the strength of the peptide network, a reduction in the rate at which a network forms at a newly created interface, or complete dissipation of intermolecular peptide interactions within the peptide network. In other embodiments, the peptide network is unable to form or forms slowly at a newly created interface while being exposed to the first stimulus but is able to form or forms rapidly when exposed to the second stimulus thereby delaying formation of the peptide network. In some embodiments steps i) and ii) are repeated one or more times allowing formation or strengthening and dissipation or weakening of the strength of the peptide network, a plurality of times.

Another aspect of the present invention provides a method of modulating the formation of a peptide network at a fluid-fluid interface comprising exposing peptides capable of participating in a self-assembled, force-transmitting peptide network to a first condition or to a second condition, wherein under the first condition individual peptides have a first chemical and/or physical property that causes the peptides to interact with one another to thereby form the network and wherein under the second condition individual peptides have a second physical and/or chemical property that disrupts interactions between or within the peptides resulting in weakening or dissipation of the network.

In still another aspect of the invention there is provided a method of modulating force transmission in a self-assembled, force-transmitting peptide network at a fluid-fluid interface comprising exposing a peptide capable of participating in a self-assembled, force-transmitting peptide network, either before or after it interacts with other peptides to form the peptide network, to a stimulus that alters the chemical and/or physical properties of the peptide. In some embodiments the modulation provides a switch such that under one set of conditions a peptide network is formed and under another set of conditions the peptide network is unable to form, is weakened or entirely dissipates.

In a further aspect, there is provided a method of modulating force transmission in a self-assembled, force-transmitting peptide network at a fluid-fluid interface comprising the steps of:
  i) at a first time, exposing a peptide capable of participating in a self-assembled, force-transmitting peptide network, either before or after it interacts with other peptides to form the peptide network, to a first stimulus that alters the chemical and/or physical properties of the peptide; and
  ii) at a second time, exposing the peptide to a second stimulus that alters the chemical and/or physical properties of the peptide adopted upon exposure to the first stimulus.

In some embodiments, the first stimulus causes the formation of a force-transmitting peptide network and the second stimulus causes a reduction in force transmission by the peptide network or abolition of force transmission by the peptide network. In other embodiments, the peptide network is unable to form or forms slowly at a newly created interface while being exposed to the first stimulus but is able to form when exposed to the second stimulus thereby delaying the formation of the force-transmitting peptide network. In some embodiments, steps i) and ii) are repeated one or more times allowing the formation and dissipation of a force-transmitting peptide network or weakening of the force transmission of the force-transmitting peptide network a plurality of times.

In another aspect of the invention there is provided a self-assembled, force-transmitting peptide network formed at a fluid-fluid interface wherein the peptide network comprises peptides that interact with one another and that have an affinity for the fluid-fluid interface and wherein the force transmission of the peptide network is manipulable by exposure to a stimulus which alters the physical and/or chemical properties of the peptide.

In yet another aspect of the invention there is provided a foam comprising a self-assembled, force-transmitting peptide network formed at a fluid-fluid interface wherein the peptide network comprises peptides that interact with one another and that have an affinity for the fluid-fluid interface and wherein the force transmission of the peptide network is manipulable by exposure to a stimulus which alters the chemical and/or physical properties of the peptide. In some embodiments, the foam is stabilized by the self-assembled, force-transmitting peptide network.

In a further aspect of the invention there is provided an oil-in-water or water-in-oil emulsion comprising a self-assembled, force-transmitting peptide network formed at a fluid-fluid interface wherein the peptide network comprises peptides that interact with one another and that have an affinity for the fluid-fluid interface and wherein the force transmission of the peptide network is manipulable by exposure to a stimulus which alters the chemical and/or physical properties of the peptide. In some embodiments, the emulsion is stabilized by the self-assembled, force-transmitting peptide network.

In yet a further aspect of the invention, there is provided a method of modulating the stability of a foam comprising a self-assembled, force-transmitting peptide network at a liquid-gas interface; said method comprising
  i) at a first time, exposing the liquid-gas interface to a first stimulus that alters the chemical and/or physical properties of a peptide in the peptide network; and
  ii) at a second time, exposing the liquid-gas interface to a second stimulus that alters the chemical and/or physical properties of the peptide in the peptide network adopted upon exposure to the first stimulus.

In some embodiments, the first stimulus causes formation of the force-transmitting peptide network or an increase in the force transmission of the peptide network and the second stimulus causes a reduction in the force transmission of the peptide network or the abolition of force transmission by the peptide network or causes a reduction in the rate of formation of the peptide network. In these embodiments, the stability of the foam is increased upon exposure to the first stimulus and the foam is destabilized upon exposure to the second stimulus, in some cases resulting in collapse of the foam. In other embodiments, the first stimulus reduces the force transmission of the peptide network at the interface and the second stimulus increases the force transmission of the peptide network at the interface. In these embodiments, the foam initially has a reduced stability and upon exposure to the second stimulus, the stability of the foam is increased.

In still a further aspect of the invention, there is provided a method of modulating the stability of an emulsion comprising a self-assembled, force-transmitting peptide network at a liquid-liquid interface; said method comprising:
  ia) at a first time, exposing the liquid-liquid interface to a first stimulus that alters the chemical and/or physical properties of a peptide in the peptide network; and iia) at a second time, exposing the liquid-liquid interface to a second stimulus that alters the chemical and/or physical properties of the peptide in the peptide network adopted upon exposure to the first stimulus.

In some embodiments, the first stimulus causes formation of the force-transmitting peptide network or an increase in the force transmission of the peptide network and the second stimulus causes a reduction in the force transmission of the peptide network or abolition of the force transmission by the peptide network or causes the rate of formation of the peptide network to be reduced. In these embodiments, the stability of the emulsion is increased upon exposure to the first stimulus and the stability of the emulsion is decreased upon exposure to the second stimulus. In some cases the second stimulus may result in destabilization which results in coalescence of the dispersed phase of the emulsion and separation of the phases. In other embodiments, the first stimulus reduces the force transmission of the peptide network at the interface and the second stimulus increases the force transmission of the peptide network at the interface. In these embodiments, the emulsion initially has a reduced stability and upon exposure to the second stimulus, the stability of the emulsion is increased.

DETAILED DESCRIPTION OF THE INVENTION

Definitions

Figure 1:
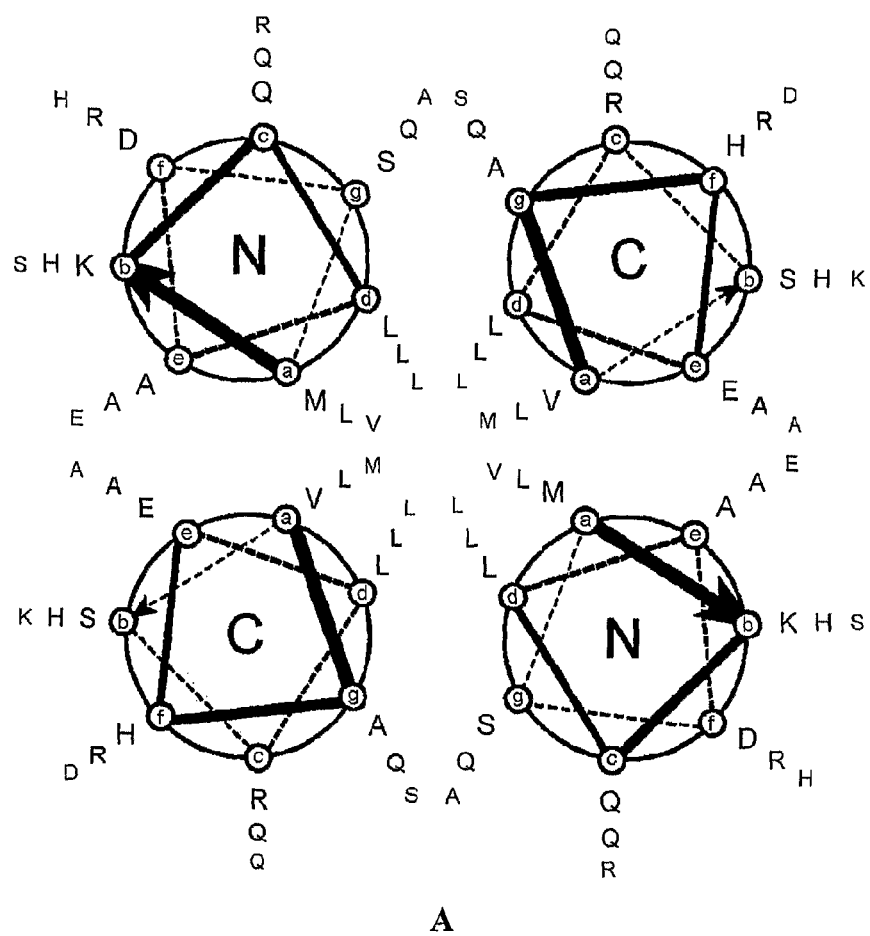
FIG. 1 is a diagrammatic representation of bulk phase tetrameric peptide clusters formed from peptides with SEQ ID NO:1 (A), SEQ ID NO:2 (B) and SEQ ID NO:3 (C). The tetrameric ensembles are shown as antiparallel coiled-coils with a hydrophobic core and a hydrophilic exterior. When exposed to a liquid-liquid interface these clusters disassociate and the monomers self-assemble at the interface creating an ensemble having specific interfacial characteristics.
Figure 1:
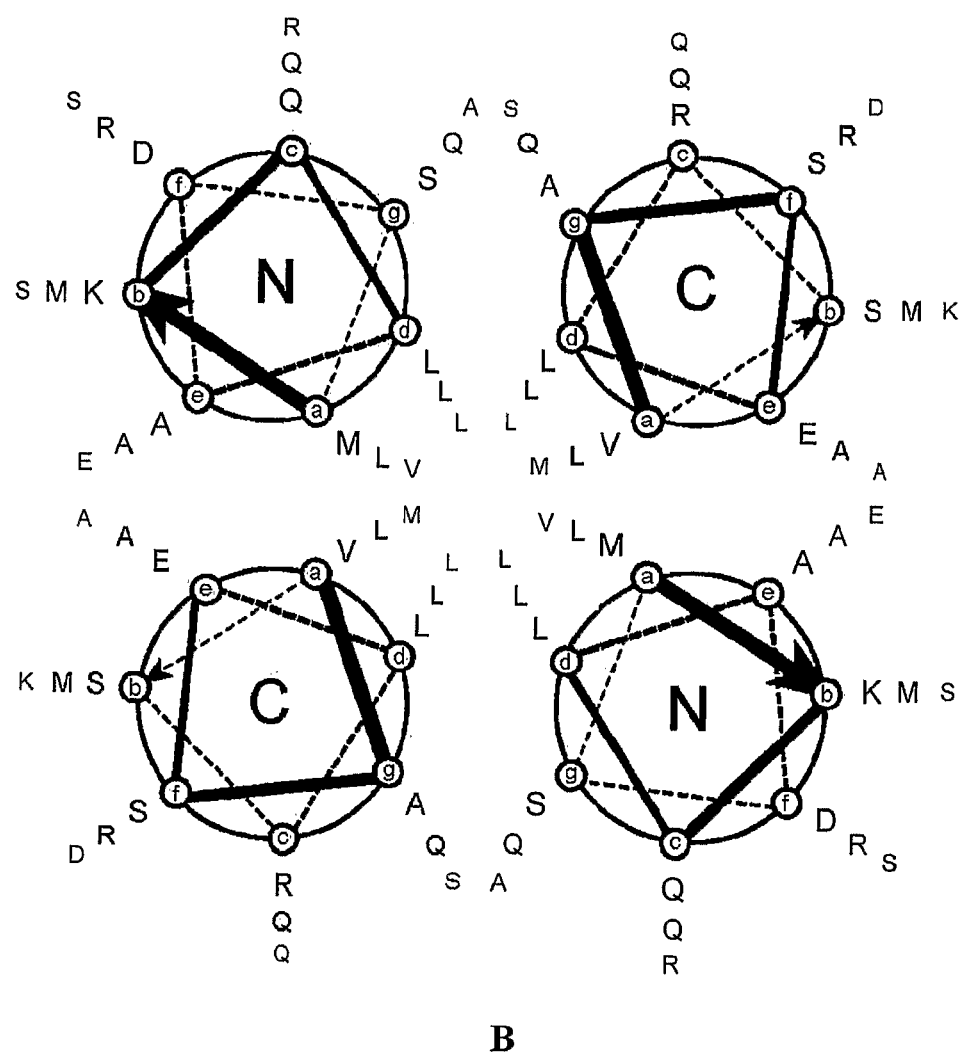
Figure 1:
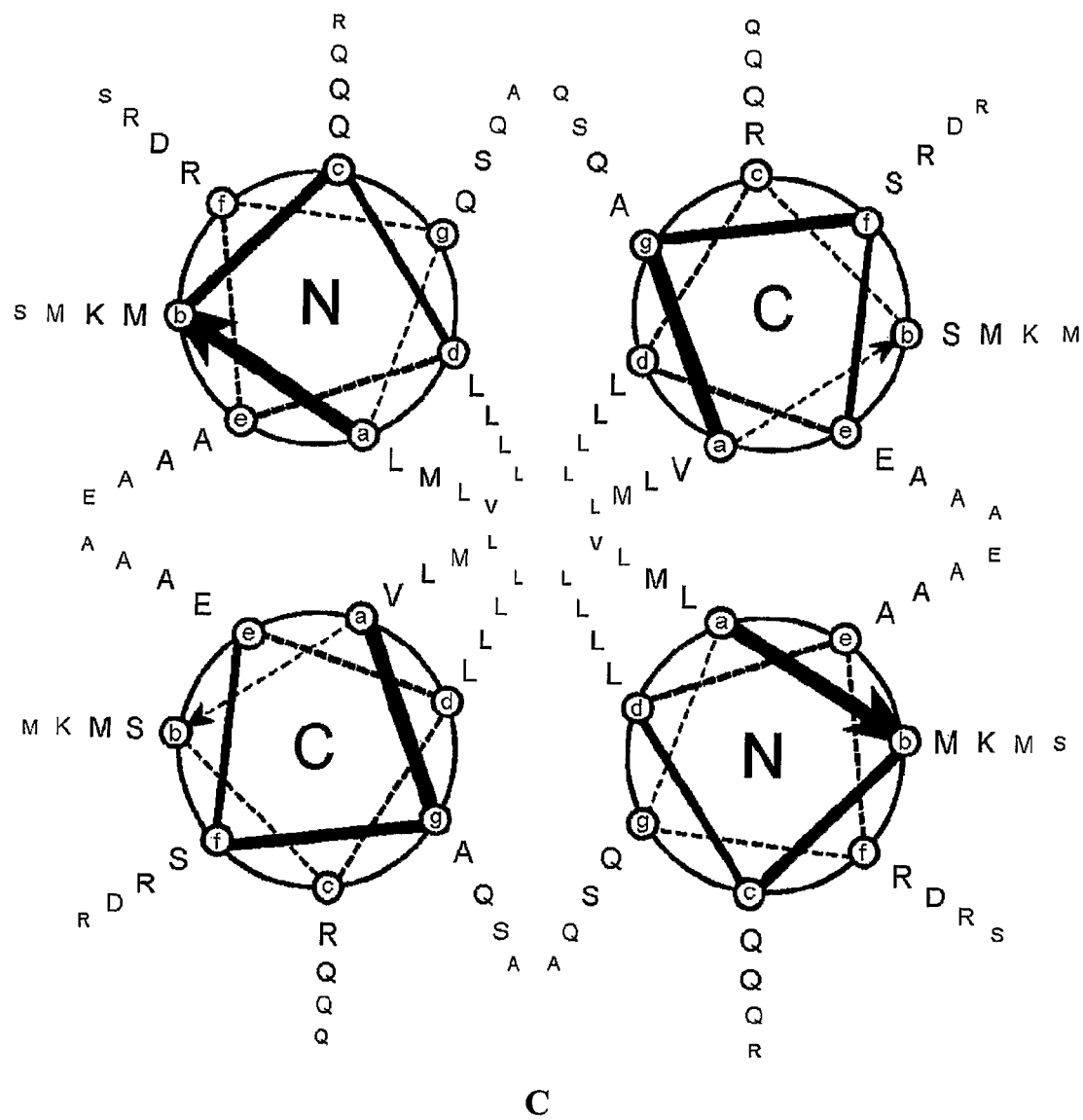

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 20%, or 10% to a reference quantity, level, value, dimension, size, or amount.

As used herein the term "acid" refers to a substance that can donate one or more hydrogen ions ($H^+$) to a second substance, where the receiving substance is a base. The addition of acid lowers the pH of an aqueous solution. Examples of suitable acids include inorganic acids and organic acids. Examples of suitable inorganic acids include, but are not limited to, hydrochloric acid, hydrofluoric acid, hydrobromic acid, hydroiodic acid, nitric acid, sulfuric acid and phosphoric acid. Examples of suitable organic acids include, but are not limited to, acetic acid, formic acid, propionic acid, butyric acid, benzoic acid, citric acid, tartaric acid, malic acid, maleic acid, hydroxymaleic acid, fumaric acid, lactic acid, mucic acid, gluconic acid, oxalic acid, phenylacetic acid, methanesulphonic acid, toluenesulphonic acid, benzenesulphonic acid, salicylic acid, sulphanilic acid, ascorbic acid, valeric acid, succinic acid, glutaric acid and adipic acid.

As used herein the term "affinity for the fluid-fluid interface" means that peptides from a bulk solution are attracted to the fluid-fluid interface such that the concentration of peptides at the fluid-fluid interface is greater than the concentration of peptides in the bulk solution. In general, the peptides have hydrophobic regions and align themselves at the interface to minimize their free energy on adsorption, typically such that their hydrophobic region is in contact with a nonpolar portion of the interface and their hydrophilic region is in contact with a polar portion of the interface.

As used herein, the term "amphipathic" refers to peptides or molecules having both hydrophilic and hydrophobic regions. "Amphipathic" and "amphiphilic" are synonymous and are used interchangeably herein.

The term "base" as used herein refers to a substance that is capable of accepting a hydrogen ion ($H^+$). The addition of base increases the pH of an aqueous solution. Examples of suitable bases include ammonia, organic amines, sodium hydroxide, potassium hydroxide, calcium hydroxide, magnesium hydroxide, sodium carbonate, potassium carbonate, magnesium carbonate, calcium carbonate, sodium bicarbonate, potassium bicarbonate, magnesium bicarbonate and calcium bicarbonate.

As used herein, the term "chaotropic agent" refers to a substance which destabilizes molecular structure, for example, by weakening or disrupting intermolecular or intramolecular interactions hydrogen bonding or hydrophobic interactions. Examples of suitable chaotropic agents include urea and guanidinium chloride.

The term "chelating agent" as used herein refers to a compound that can form a complex with a metal ion. In particular, chelating agents are bi- or polydentate metal ion ligands having at least two heteroatoms capable of simultaneously coordinating with the metal ion. Illustrative examples of chelating agents suitable for use in the invention include ethylenediamine, ethylenetriamine, triethylenetetramine, ethylenediaminetetraacetic acid (EDTA), aminoethanolamine, ethylene glycol bis(2-aminoethyl ether)-N,N,N'N'-tetraacetic acid (EGTA), tris(2-imidazolyl)carbinol, tris[4(5)-imidazolyl]carbinol, bis[4(5)-imidazolyl]glycolic acid, oxaloacetic acid, citric acid, glycine or other amino acids, salicylate, macrocyclic ethers, multidentate Schiff bases, acetylacetone, bis(acetylacetone) ethylenediimine, 2-nitroso-1-naphthol, 3-methoxyl-2-nitrosophenol, cyclohexanetrione trioxime, diethylenetriaminepentaacetic acid (DTPA), N-(hydroxyethyl)ethylenediaminetriacetic acid (HEDTA), tripolyphosphate ion, nitrilotriacetic acid, dimethylglyoxime, dimercaprol and deferoxamine.

As used herein, the term "chemical and/or physical properties of the peptide" refers to the chemical properties such as charge, polarity, and redox state, and physical properties such as peptide conformation, affinity for the interface or aggregation state. For example, a change in pH of the bulk solution may cause ionization of a basic or acidic group such as a carboxylic acid present on the peptide and therefore development of a charge. If the charge is spatially close to other functional groups in another peptide which also have the same charge at the new pH, peptides in the network may repel one another causing weakening of the network or may cause the network to dissipate. If a charge causes a repulsion within a peptide, the conformation of the peptide may change and this in turn may cause weakening or loss of intermolecular interactions within the network. Alternatively, if the charge is spatially close to other functional groups in another peptide having an opposite charge at the new pH, peptides in the network may be more strongly attracted to one another, causing strengthening of the network. If a charge causes an interaction within a peptide, an ordered conformation of the peptide may be stabilized, and this in turn may cause strengthening of intermolecular interactions and strengthening of the network. In another example, a change in pH may cause the average charge on a peptide molecule to approach zero, thus diminishing any charge-charge repulsions between peptides and strengthening the network. In yet another example, a change in pH may cause the average positive or negative charge on a peptide molecule to deviate significantly from zero, thus generating charge-charge repulsions between peptides which weaken the network or cause it to dissipate entirely. Alternatively, a change in charge or polarity or a change in conformation of a peptide may alter the hydrophilic and/or hydrophobic regions of the peptide causing it to have a stronger or weaker affinity for the interface which may in turn provide a peptide concentration at the interface sufficient to allow network formation or may deplete the concentration of peptide at the interface such that it is insufficient for network formation or may alter the rate at which peptides enter the interface and form a network either increasing or decreasing the rate of peptide network formation. In another example, a change in charge or polarity or a change in conformation of a peptide may alter the energy barrier for entry of a peptide to the interface altering the rate at which the network forms at the interface. Another illustrative example is the addition of a metal ion which in the presence of appropriate bridging groups may stabilize the peptide in an α-helical or β-sheet conformation and provide a hydrophobic face or region which has an affinity for the interface. In addition, binding of a metal ion may cause the average charge on a peptide molecule to approach zero, thus diminishing any charge-charge repulsions between peptides and strengthening the network. In addition, a metal ion may bind concurrently to two or more peptide molecules, causing cross-linking of two or more peptide molecules at the interface and thus strengthening the network. In some cases, such cross-linking may lead to formation of a multilayered peptide architecture at the interface. In addition, a metal ion may bind concurrently to two or more peptide molecules, causing cross-linking of two or more peptide molecules in bulk solution and increasing the effective molecular weight of the peptide complex, thus affecting the rate at which peptide can enter the interface to form a peptide network and/or the architecture adopted by peptide molecules at the interface. In addition, a metal ion may bind to a peptide molecule in bulk solution, altering the charge on the peptide and affecting the rate at which the peptide can enter the interface to form a network. Conversely, removal of metal ions may destabilize an alpha helical conformation or may cause the peptide to adopt a random coil conformation which does not have a distinct hydrophobic region and which does not have a high affinity for the interface or may remove metal-mediated cross-linking at the interface. Alternatively, in peptides having different design features, binding of a metal ion may give rise to a local positive charge in a peptide which may interact with a nearby positive charge at a given pH to destabilize the structure of the peptide, thus weakening the network or causing it to dissipate entirely. Alternatively, binding of a metal ion may neutralize a local negative charge which previously stabilized an ordered conformation of the peptide, thus leading to conformational destabilization of the peptide which weakens the network or causes it to dissipate entirely. In another example, binding of a metal ion may cause the average positive charge on a peptide molecule to deviate significantly from zero, thus generating charge-charge repulsions between peptides which weaken the network or cause it to dissipate entirely. Another illustrative example is the use of organic molecules bearing a molecular charge (organic counterions) to stabilize an ordered conformation of a peptide bearing the opposite charge, thus strengthening the network. Another illustrative example is the use of two different peptides bearing opposite charges at a given pH which are able to form a mixed peptide network, where the charge of one or both molecules may be altered by altering the pH of the solution or by adding or sequestering metal ions, thus altering the strength of the network. In some instances only the chemical properties of the peptide are altered. In other instances only the physical properties of the peptide are altered. In some instances both the chemical and physical properties of the peptide are altered. Importantly, because of the relatively simple and well-defined nature of peptides, it is possible to make predictions regarding the physical and chemical properties of a given peptide. It is therefore possible to design peptides to have a predictable network strength and predictable modulation characteristics, such as sensitivity to pH, oxidation/reduction or metal ion chelation.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "emulsion" refers to a suspension or dispersion of a first liquid suspended or dispersed in a second liquid in which the first liquid is poorly soluble or non-miscible. The first liquid is referred to as the dispersed phase and the second liquid is referred to as the continuous phase. The dispersed phase may form droplets which are dispersed throughout the continuous phase in a heterogenous or homogeneous manner. Illustrative examples of emulsions include oil-in-water emulsions in which the oil forms the dispersed phase and the water forms the Continuous phase, and water-in-oil emulsions in which the water forms the dispersed phase and the oil forms the continuous phase. In addition, "multiple emulsions" may be formed in which droplets of a first discontinuous phase contain smaller droplets of a second discontinuous phase, which may or may not be similar in composition to the continuous phase containing the first discontinuous phase. Illustrative examples of multiple emulsions include water-in-oil-in-water emulsions in which the oil forms the first discontinuous phase and water forms the second discontinuous phase, and oil-in-water-in-oil emulsions in which the water forms the first discontinuous phase and oil forms the second discontinuous phase.

As used herein, the term "fluid-fluid interface" refers to a surface forming the common boundary between two adjacent non-miscible fluids. The fluids may be liquids or gases. A fluid-fluid interface includes a liquid-liquid interface and a gas-liquid interface. A gas-liquid interface is the surface forming the common boundary between a gas and a liquid, for example, air and water or air and oil. A liquid-liquid interface is the surface forming the common boundary between two immiscible liquids, such as oil and water.

As used herein, the term "foam" refers to a dispersion of gas bubbles in or on a liquid. The gas bubbles may be dispersed throughout the liquid phase in a heterogeneous or homogeneous manner. Illustrative examples of foams include gases such as air, nitrogen, oxygen, helium or hydrogen entrapped in a liquid such as water or an oil. A foam may be transient, unstable or stable.

The term "force transmission" and "force-transmitting" as used herein refers to a peptide network which is capable of transmitting lateral force along or within a fluid-fluid interface and imparts mechanical strength to the fluid-fluid interface. The force transmission of a peptide network can be assessed by determining the interfacial elasticity modulus from the initial slope of an interfacial stress versus strain curve at a strain near zero, and the peak interfacial stress that the network is able to sustain before rupture. For a peptide network to demonstrate useful force transmission, the interfacial elasticity modulus is usually greater than or equal to 30 mN/m, and the peak or maximum interfacial stress usually greater than 0.5 mN/m.

As used herein, the terms "interact", "interacts", "interaction" and "interacting" refer to attractive forces that occur within a peptide or between peptides. The attractive forces may be responsible for the conformation adopted by a peptide and thereby influence the affinity of the peptide for the fluid-fluid interface, or may promote or discourage association with other peptides. The attractive forces may also be intermolecular thereby encouraging the peptides located at the interface to associate with one another which may result in network formation. Illustrative examples of suitable interactions include ion-pair interactions, dipole interactions, London dispersion forces, salt bridge formation, hydrogen bonding and short range solvation forces such as hydration, hydrophobic interactions, osmotic attractive potential due to the exclusion of ions, and surface charge interactions. In some cases, intermolecular or intramolecular covalent bonding, such as disulfide bond formation may occur between peptides. In the context of peptide network formation, covalent bonding between peptides may be less desirable if stimuli-responsive abolition of the network is desired.

The term "interfacial characteristics" as used herein refers to characteristics of the fluid-fluid interface including surface tension of a liquid at the fluid-fluid interface, the charge properties of the interface, interfacial rheology such as the viscosity and elastic properties of the interface and whether or not force is able to be transmitted through the region of the fluid-fluid interface.

As used herein the term "interfacial elasticity modulus" also known as the "storage modulus" refers to the gradient of the interfacial stress versus strain plot in the limit of zero strain and thus relates to the work required to expand the self-assembled, force-transmitting peptide network at the fluid-fluid interface. The interfacial elasticity modulus is obtained by plotting the interfacial stress versus the strain applied to the peptide ensemble and the slope of the line at a given low range of strain will give the interfacial elasticity modulus. An approximate value for the elasticity modulus may also be obtained using conventional interfacial rheology techniques.

The term "interfacial viscous modulus" also known as "loss modulus" refers to the ability of a self-assembled, force-transmitting peptide network to flow at the fluid-fluid interface thus dissipating any applied force. On an interfacial stress versus strain plot, in the absence of the addition of new peptides to the ensemble, the loss modulus relates to the rate at which measured interfacial stress relaxes when the network is at constant strain.

As used herein, the terms "modulate", "modulation" and "modulating" refer to a regulation or adjustment to a certain measure or proportion. Modulation when applied to interfacial characteristics refers to enhancement, reduction or abolition of the characteristic. For example, modulation when applied to force transmission refers to an enhancement of force transmission, a reduction in force transmission or abolition of force transmission.

As used herein, "peak interfacial stress" refers to the point of maximum interfacial stress on an interfacial stress versus strain curve and is related to the interfacial elastic modulus, the interfacial viscous modulus, the rate of strain and the rate at which new peptides are adsorbed at the interface.

As used herein, the term "peptide" refers to two or more naturally occurring or non-naturally occurring amino acids joined by peptide bonds. Generally, peptides will range from about 2 to about 80 amino acid residues in length, usually from about 5 to about 60 amino acid residues in length and more usually from about 10 to about 40 amino acid residues in length. The peptide may also be a retro-inverso peptide.

As used herein, the term "amino acid" refers to an α-amino acid or a β-amino acid and may be a L- or D-isomer. The amino acid may have a naturally occurring side chain (see Table 1) or a non-naturally occurring side chain (see Table 2). The amino acid may also be further substituted in the α-position or the β-position with a group selected from —$C_1$-$C_6$alkyl, —$(CH_2)_nCOR_1$, —$(CH_2)_nR_2$, —$PO_3H$, —$(CH_2)_n$heterocyclyl or —$(CH_2)_n$aryl where $R_1$ is —OH, —$NH_2$, —$NHC_1$-$C_3$alkyl, —$OC_1$-$C_3$alkyl or —$C_1$-$C_3$alkyl and $R_2$ is —OH, —SH, —$SC_1$-$C_3$alkyl, —$OC_1$-$C_3$alkyl, —$C_3$-$C_{12}$cycloalkyl, —$NH_2$, —$NHC_1$-$C_3$alkyl or —NHC(C=NH)$NH_2$ and where each alkyl, cycloalkyl, aryl or heterocyclyl group may be substituted with one or more groups selected from —OH, —$NH_2$, —$NHC_1$-$C_3$alkyl, —$OC_1$-$C_3$alkyl, —SH, —$SC_1$-$C_3$alkyl, —$CO_2H$, —$CO_2C_1$-$C_3$alkyl, —$CONH_2$ or —$CONHC_1$-$C_3$alkyl.

Amino acid structure and single and three letter abbreviations used throughout the specification are defined in Table 1, which lists the twenty naturally occurring amino acids which occur in proteins as L-isomers.

TABLE 1

(1)

| Amino Acid | Three-letter Abbreviation | One-letter symbol | Structure of side chain (R) |
|---|---|---|---|
| Alanine | Ala | A | —$CH_3$ |
| Arginine | Arg | R | —$(CH_2)_3NHC(=N)NH_2$ |
| Asparagine | Asn | N | —$CH_2CONH_2$ |
| Aspartic acid | Asp | D | —$CH_2CO_2H$ |
| Cysteine | Cys | C | —$CH_2SH$ |
| Glutamine | Gln | Q | —$(CH_2)_2CONH_2$ |
| Glutamic acid | Glu | E | —$(CH_2)_2CO_2H$ |
| Glycine | Gly | G | —H |
| Histidine | His | H | —$CH_2$(4-imidazolyl) |
| Isoleucine | Ile | I | —$CH(CH_3)CH_2CH_3$ |
| Leucine | Leu | L | —$CH_2CH(CH_3)_2$ |
| Lysine | Lys | K | —$(CH_2)_4NH_2$ |
| Methionine | Met | M | —$(CH_2)_2SCH_3$ |
| Phenylalanine | Phe | F | —$CH_2Ph$ |
| Proline | Pro | P | see formula (2) above for structure of amino acid |
| Serine | Ser | S | —$CH_2OH$ |

TABLE 1-continued (1)

| Threonine | Thr | T | —$CH(CH_3)OH$ |
|---|---|---|---|
| Tryptophan | Trp | W | —$CH_2$(3-indolyl) |
| Tyrosine | Tyr | Y | —$CH_2$(4-hydroxyphenyl) |
| Valine | Val | V | —$CH(CH_3)_2$ |

The term "α-amino acid" as used herein, refers to a compound having an amino group and a carboxyl group in which the amino group and the carboxyl group are separated by a single carbon atom, the α-carbon atom. An α-amino acid includes naturally occurring and non-naturally occurring L-amino acids and their D-isomers and derivatives thereof such as salts or derivatives where functional groups are protected by suitable protecting groups. The α-amino acid may also be further substituted in the α-position with a group selected from —$C_1$-$C_6$alkyl, —$(CH_2)_nCOR_1$, —$(CH_2)_nR_2$, —$PO_3H$, —$(CH_2)_n$heterocyclyl or —$(CH_2)_n$aryl where $R_1$ is —OH, —$NH_2$, —$NHC_1$-$C_3$alkyl, —$OC_1$-$C_3$alkyl or —$C_1$-$C_3$alkyl and $R_2$ is —OH, —SH, —$SC_1$-$C_3$alkyl, —$OC_1$-$C_3$alkyl, —$C_3$-$C_{12}$cycloalkyl, —$NH_2$, —$NHC_1$-$C_3$alkyl or —NHC(C=NH)$NH_2$ and where each alkyl, cycloalkyl, aryl or heterocyclyl group may be substituted with one or more groups selected from —OH, —$NH_2$, —$NHC_1$-$C_3$alkyl, —$OC_1$-$C_3$alkyl, —SH, —$SC_1$-$C_3$alkyl, —$CO_2H$, —$CO_2C_1$-$C_3$alkyl, —$CONH_2$ or —$CONHC_1$-$C_3$alkyl.

As used herein, the term "β-amino acid" refers to an amino acid that differs from an α-amino acid in that there are two (2) carbon atoms separating the carboxyl terminus and the amino terminus. As such, β-amino acids with a specific side chain can exist as the R or S enantiomers at either of the α (C2) carbon or the β (C3) carbon, resulting in a total of 4 possible isomers for any given side chain. The side chains may be the same as those of naturally occurring α-amino acids (see Table 1 above) or may be the side chains of non-naturally occurring amino acids (see Table 2 below).

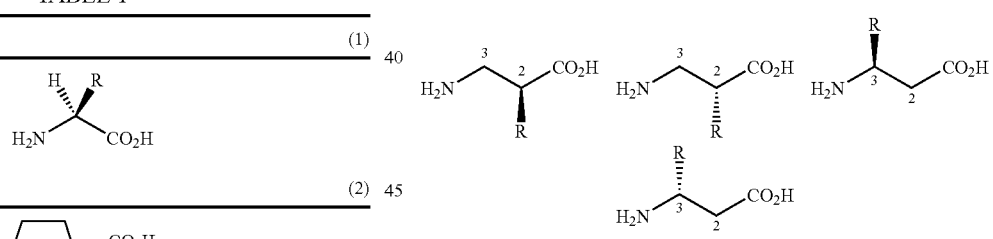

Furthermore, the β-amino acids may have mono-, di-, tri- or tetra-substitution at the C2 and C3 carbon atoms. Mono-substitution may be at the C2 or C3 carbon atom. Di-substitution includes two substituents at the C2 carbon atom, two substituents at the C3 carbon atom or one substituent at each of the C2 and C3 carbon atoms. Tri-substitution includes two substituents at the C2 carbon atom and one substituent at the C3 carbon atom or two substituents at the C3 carbon atom and one substituent at the C2 carbon atom. Tetra-substitution provides for two substituents at the C2 carbon atom and two substituents at the C3 carbon atom. Suitable substituents include —$C_1$-$C_6$alkyl, —$(CH_2)_nCOR_1$, —$(CH_2)R_2$, —$PO_3H$, —$(CH_2)_n$heterocyclyl or —$(CH_2)_n$aryl where $R_1$ is —OH, —$NH_2$, —$NHC_1$-$C_3$alkyl, —$OC_1$-$C_3$alkyl or —$C_1$-$C_3$alkyl and $R_2$ is —OH, —SH, —$SC_1$-$C_3$alkyl, —$OC_1$-$C_3$alkyl, —$C_3$-$C_{12}$cycloalkyl, —$NH_2$, —$NHC_1$-$C_3$alkyl or —NHC(C=NH)$NH_2$ and where each alkyl, cycloalkyl, aryl or heterocyclyl group may be substituted with one or more groups selected from —OH, —$NH_2$, —$NHC_1$-$C_3$alkyl, —$OC_1$-$C_3$alkyl, —SH, —$SC_1$-$C_3$alkyl, —$CO_2H$, —$CO_2C_1$-$C_3$alkyl, —$CONH_2$ or —$CONHC_1$-$C_3$alkyl.

Other suitable β-amino acids include conformationally constrained β-amino acids. Cyclic β-amino acids are conformationally constrained and are generally not accessible to enzymatic degradation. Suitable cyclic β-amino acids include, but are not limited to, cis- and trans-2-aminocyclopropyl carboxylic acids, 2-aminocyclobutyl and cyclobutenyl carboxylic acids, 2-aminocyclopentyl and cyclopentenyl carboxylic acids, 2-aminocyclohexyl and cyclohexenyl carboxylic acids and 2-amino-norbornane carboxylic acids and their derivatives, some of which are shown below:

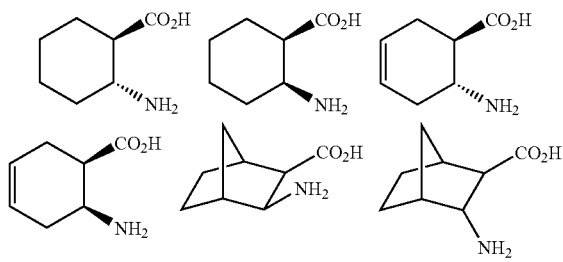

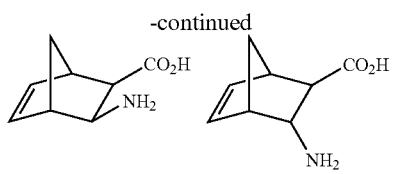

Suitable derivatives of β-amino acids include salts and may have functional groups protected by suitable protecting groups.

The term "non-naturally occurring amino acid" as used herein, refers to amino acids having a side chain that does not occur in the naturally occurring L-α-amino acids listed in Table 1. Examples of non-natural amino acids and derivatives include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, citrulline, sarcosine, 4-amino-3-hydroxy-6-methylheptanoic acid, 2-thienyl alanine and/or D-isomers of amino acids. A list of unnatural amino acids that may be useful herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-N-methylalanine | Dnmala | N-cyclooctylglycine | Ncoct |
| D-N-methylarginine | Dnmarg | N-cyclopropylglycine | Ncpro |

TABLE 2-continued

| Non-conventional amino acid | Code | Non-conventional amino acid | Code |
|---|---|---|---|
| D-N-methylasparagine | Dnmasn | N-cycloundecylglycine | Ncund |
| D-N-methylasparatate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethy)glycine | Nthr |
| D-N-methylhistidine | Dnmhis | N-(hydroxyethy)glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methylnapthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mtrp | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

The term "alkyl" as used herein refers to straight chain or branched hydrocarbon groups. Suitable alkyl groups include, but are not limited to methyl, ethyl, propyl, isopropyl, butyl, isobutyl, pentyl, hexyl, heptyl, octyl, nonyl, decyl, dodecyl, tetradecyl, hexadecyl and octadecyl. The term alkyl may be prefixed by a specified number of carbon atoms to indicate the number of carbon atoms or a range of numbers of carbon atoms that may be present in the alkyl group. For example, $C_1$-$C_3$ alkyl refers to methyl, ethyl, propyl and isopropyl.

The term "alkenyl" as used herein refers to straight chain or branched hydrocarbon groups containing at least one double bond. Suitable alkenyl groups include, but are not limited to vinyl, propenyl, 1-butenyl, 2-butenyl, 3-butenyl, 3-methyl-2-butenyl, 1-pentenyl, 2-pentenyl, 3-pentenyl, 4-pentenyl, 3-methyl-2-pentenyl, 4-methyl-3-pentenyl, 2,4-pentadiene, 1-hexenyl, 2-hexenyl, 3-hexenyl, 4-hexenyl, 5-hexenyl, 3-methyl-2-hexenyl, 4-methyl-3-hexenyl and 5-methyl-4-hexenyl.

The term "alkynyl" as used herein refers to straight chain or branched hydrocarbon groups containing at least one triple bond. Suitable alkynyl groups include, but are not limited to ethynyl, 2-propynyl, 2-butynyl, 3-butynyl, 2-pentynyl, 3-pentynyl, 4-pentynyl, 2-hexynyl, 3-hexynyl, 4-hexynyl and 5-hexynyl.

The term "cycloalkyl" as used herein, refers to cyclic hydrocarbon groups. Suitable cycloalkyl groups include, but are not limited to, cyclopropyl, cyclobutyl, cyclopentyl, cyclohexyl, cycloheptyl, cyclooctyl, cyclononyl, cyclodecyl, cycloundecyl and cyclododecyl.

The term "heterocyclyl" as used herein refers to 5 or 6 membered saturated, partially unsaturated or aromatic cyclic hydrocarbon groups in which at least one carbon atom has been replaced by N, O or S. Optionally, the heterocyclyl group may be fused to a phenyl ring. Suitable heterocyclyl groups include, but are not limited to pyrrolidinyl, piperidinyl, pyrrolyl, thiophenyl, furanyl, oxazolyl, imidazolyl, thiazolyl, isoxazolyl, pyrazolyl, isothiazolyl, pyridinyl, quinolinyl, isoquinolinyl, indolyl, benzofuranyl, benzothiophenyl, oxadiazolyl, tetrazolyl, triazolyl and pyrimidinyl.

The term "aryl" as used herein, refers to $C_6$-$C_{10}$ aromatic hydrocarbon groups, for example phenyl and naphthyl.

The term "peptide ensemble" refers to a population of peptides which have self-assembled at the fluid-fluid interface from the bulk solution because they have an affinity for the fluid-fluid interface. A peptide ensemble is a broad term encompassing any population of peptides at the fluid-fluid interface. Peptide ensembles include:

i) peptide populations in which there is no or very little net interaction between the peptides of the population and therefore no mechanical strength associated with the peptide population at the fluid-fluid interface;

ii) peptide populations in which there is at least some interaction between peptides of the population but the interaction is insufficient to impart mechanical strength on the population at the fluid-fluid interface; and iii) peptide populations in which the peptides are present at a sufficient concentration at the interface and there is sufficient interaction between the peptides to impart mechanical strength on the peptide population at the fluid-fluid interface. Such a peptide population is capable of transmitting force. Herein, this peptide population capable of transmitting force is referred to as a "peptide network".

In ensembles i) and ii) there may be an inadequate concentration of peptide at the interface to allow sufficient interaction to impart mechanical strength by forming a peptide network, possibly because the peptide has a low affinity for the interface. Alternatively, the peptides which have self-assembled at the fluid-fluid interface are not able to interact with each other or the interactions between peptides are non-uniform or are easily disrupted.

The term "self-assembled" refers to a population of peptides with an affinity for the fluid-fluid interface and which relocate themselves from the bulk solution to the fluid-fluid interface to form a peptide ensemble.

The term "self-assembled, force-transmitting peptide network" refers to a peptide ensemble comprising a peptide population which is present in a sufficient concentration at the interface and in which there is sufficient interaction between the peptides to impart mechanical strength upon the peptide population thereby forming a network at the fluid-fluid interface which allows transmission of force when interfacial stress is applied to the peptide network. The peptide network may also be referred to as a film or peptide film.

As used herein the term "stimulus which alters the chemical and/or physical properties of the peptide" is a substance which is capable of altering the chemical properties such as charge, polarity or oxidation state of substituent groups on the peptide or altering the physical properties of a peptide such as conformation, spatial arrangement of functional groups or the affinity of the peptide for the fluid-fluid interface, thereby disrupting or strengthening interactions within a peptide or between peptides within the peptide network and/or reducing or increasing the concentration of peptide at the fluid-fluid interface and/or reducing or increasing the rate of formation of a peptide network. For example, interactions may be disrupted by altering the ionization of the functional groups of the peptide to introduce repulsive forces between amino acids within a peptide or between two peptides. Alternatively, interactions may be strengthened by bringing functional groups which may form cross-links such as hydrogen bonds into closer association with one another or by bridging like functional groups with metal ions. Suitable stimuli which alter peptide conformation include acids, bases, metal ions, metal chelating agents, organic or inorganic charge-bearing species (counterions), oxidizing agents, reducing agents, chaotropic agents, salts and temperature or mixtures thereof. In addition, suitable stimuli may include substances that remove a first stimuli-providing substance from contact with the peptide. For example, the stimuli may remove a first stimuli-providing substance by adsorption onto a surface or by inducing complexation or precipitation of the first stimuli-providing substance.

As used herein, the terms "switch" and "switching" refer to turning on and off a peptide network. For example, the formation or maintenance of a peptide network during exposure to a first stimulus and the abolition or dissipation of the peptide network during exposure to a second stimulus. Alternatively, there may be prevention of peptide network formation or dissipation of the peptide network during exposure to the first stimulus and formation or formation and maintenance of the peptide network during exposure to the second stimulus.

Peptides Capable of Forming Peptide Networks

A large number of peptides are suitable for use in the present invention, therefore it is not possible to provide an exhaustive list of peptides. However, suitable peptides may be identified by a number of means. For example, peptides useful in the invention may be obtained (i) by rational design, (ii) by modification of sequences known in the natural world, (iii) by screening or selection, or by a combination of these three approaches.

i) Rational Design

The process of rational design involves de novo design of the sequence of a peptide, or a combination of two or more peptides, to exhibit a) an amphipathic character, for example as a result of the designed composition of the amino acid residues, of which some have a hydrophilic character in the side chain, and some have a hydrophobic character in the side chain. Possession of an amphipathic character gives rise to a peptide affinity for the fluid-fluid interface. In preferred embodiments, the amphipathic peptide is capable of forming an ordered secondary structure at a fluid-fluid interface. Examples of ordered amphipathic secondary structures include α-helical or β-sheet structures, b) a capacity for interaction with other peptide molecules adsorbed at the fluid-fluid interface under one set of conditions, such that at a sufficient concentration of peptide at the interface, the strength of the interactions are sufficient to allow the formation of a self-assembled, force-transmitting peptide network at the interface, and c) a capacity for modulation of the chemical and/or physical properties of the peptide at the interface under another set of conditions, such that interaction with other peptide molecules at the interface existing under the one set of conditions are weakened or abolished under the other set of conditions, or enhanced affinity for the interface under one set of conditions is reduced under the other set of conditions. This allows the strength of the network to be modulated, weakened or abolished, and may also affect the rate at which the peptide network is formed.

The design of de novo peptide sequences useful in the invention utilizes available knowledge of the forces involved in the stabilization and/or destabilization of peptide structures and stabilization and/or destabilization of peptide-peptide interactions in bulk aqueous solution, and the application of this knowledge to the context of fluid-fluid interfaces having a hydrophobic character in one of the phases, for example a gas phase or an oil phase in contact with an aqueous phase. Rational design may also be assisted by computer modelling and/or automated design algorithms. Modification of amino acid residues within a rationally designed sequence, for example, N- or C-terminus modification or amino acid side chain modification, may also be considered to increase the solubility of peptides, increase affinity for the fluid-fluid interface, increase or introduce interactions between peptides that are capable of manipulation and/or add a further desired functionality to the peptide. The process of rational design was used in the generation of the sequences of peptides having SEQ ID NO:6, SEQ ID NO:7, SEQ ID NO:8, SEQ ID NO:11, SEQ ID NO:12, SEQ ID NO:14 (Litowski and Hodges, 2002) and SEQ ID NO:15 (Litowski and Hodges, 2002).

ii) Modifications of Known Sequences

Modification of sequences known in the natural world to obtain a peptide, or a combination of two or more peptides, useful in the invention involves:

a) selection of the sequence of a peptide, or a combination of two or more peptides, from the natural world, that have an amphipathic character for example, as a result of the selected composition of amino acid residues, of which some have a hydrophilic character in the side chain, and some have a hydrophobic character in the side chain. Possession of an amphipathic character gives rise to peptide affinity for the fluid-fluid interface. In some embodiments, the peptide is capable of forming an ordered structure, such as an α-helix or β-sheet, at the fluid-fluid interface. The sequence of the peptide(s) may in some cases be derived from a larger sequence corresponding to an intact protein structure in the natural world, b) where necessary, modification of the sequence(s) to impart a capacity for interactions with other peptide molecules adsorbed at the fluid-fluid interface under one set of conditions such that at a sufficient concentration of peptide at the fluid-fluid interface, the strength of the interactions is sufficient to allow formation of a self-assembled, force-transmitting peptide network at the interface. In addition, alterations may be made to the termini of the peptide sequence(s), including but not limited to chemical modification of the peptide termini to stabilize an ordered secondary structure of the peptide or to increase the affinity of the peptide for the interface. Optionally, substitutions of amino acids in the sequence(s) may be carried out to obtain a desired functionality, including but not limited to substitutions to increase peptide solubility or to assist in peptide recovery or characterization. This process was used in the generation of the sequence of peptide having SEQ ID NO:1 from the sequence of a larger intact protein (Fairman et al., 1995). In addition, substitutions of amino acids within the sequence(s) may be carried out to increase the stability of an ordered secondary structure of the peptide, for example by placing negatively charged residues near the N-terminus of an α-helical peptide and/or positively charged residues near the C-terminus of an α-helical peptide, to stabilize the helix via charge-dipole interactions (Kohn et al., 1997a). In addition, the length of the peptide may be changed to increase the structural stability of the peptide. This process was used in the generation of the sequence of peptide having SEQ ID NO:3 from the sequence of peptide having SEQ ID NO:1 (Fairman et al., 1995). Where necessary, substitutions of amino acids within the sequence(s) may be carried out to increase the affinity of the peptide for a fluid-fluid interface. A single sequence modification may have multiple effects. For example, the sequence changes which increase the structural stability of peptide having SEQ ID NO:3 relative to peptide having SEQ ID NO:1 also increased the affinity of the peptide having SEQ ID NO:3 for a fluid-fluid interface relative to peptide having SEQ ID NO:1 (Middelberg et al., 2000) and also increased network strength at a fluid-fluid interface for peptide having SEQ ID NO:3 relative to peptide having SEQ ID NO:1, and c) one or more elements are included in the peptide sequence(s) to impart a capacity for modulation of the chemical or physical properties of the peptide at the interface under another set of conditions, such that interaction with other peptide molecules at the interface are weakened or abolished under these conditions or enhanced affinity for the interface under one set of conditions is reduced under another set of conditions. This allows the strength of the network to be modulated, weakened or abolished, and may also affect the rate at which the peptide network is formed. This process was used for the generation of the sequences of peptides having SEQ ID NO:2, SEQ ID NO:4, SEQ ID NO:5, SEQ ID NO:9 (Fairman et al., 1996, Vu et al., 2001), SEQ ID NO:10 (Fairman et al., 1996, Vu et al., 2001), and SEQ ID NO:13.

iii) Screening and/or Selection

In this process, an initial sample containing a large number of different peptide molecules having different sequences is obtained. This sample may be obtained by various different means, which include but are not limited to generation of peptides by limited proteolysis of a single protein or a mixture of proteins (Gauthier et al., 1993, van der Ven et al., 2002, van der Ven et al., 2001, Rahali et al., 2000, Huang et al, 1996, Girardet et at, 2000, Caessens et al., 1999b, Caessens et al., 1999a), combinatorial synthesis of a library of peptides by chemical means (Xu et al., 2001, Arndt et al., 2000, Boon et al., 2004, Cho et al., 1998, Rausch et al., 2005, Arndt et al., 2002), or generation of a library of peptides by biological synthesis, for example using phage display methodology (Benhar, 2001, Tamerler et al., 2003, Sarikaya et al., 2004). In some cases, a peptide library may be constructed by variation on an initial sequence obtained by rational design. In some cases, a peptide library may be constructed by variation on an initial sequence from the natural world. The initial sample containing many different peptide sequences is then subjected to a screening and/or selection process to obtain a sample enriched in a peptide or peptides useful in the invention. Various different means may be employed in a screening and/or selection process to obtain a peptide or peptides useful in the invention. For example, an initial peptide solution may be assessed for an ability to form a self-assembled, force-transmitting peptide network at a fluid-fluid interface by assessing the force transmission at a fluid-fluid interface. Another means of screening and/or selection of peptides useful in the invention is the use of a switchable foam, in which peptides) active in foam stabilization under a first condition are enriched by passing a gas through a mixed peptide solution to generate a foam selectively enriched in peptides capable of foam stabilization under a first condition. The foam is then collected and subjected to a second condition, under which the peptide or peptides of interest are not active in foam stabilization. Sufficient time is then allowed to elapse for collapse of the foam. Optionally, in a second step, the peptide solution enriched after the first selection step is further enriched by passing a gas through the first enriched peptide solution to generate a foam enriched in a peptide or peptides still capable of foam stabilization under a second condition. This second foam may then be removed to leave behind a second enriched peptide solution that is enriched in a peptide or peptides capable of stabilizing a foam under a first condition but not under a second condition. Selection steps of a similar nature may be repeated a multiplicity of times to obtain a peptide solution with desired enriched properties. This solution may be used directly for a particular application, or may be subject to further analysis to determine the sequence of the peptide or combination of peptides responsible for the observed stabilization and destabilization of foaming activity, to permit direct synthesis of the peptide or combination of peptides of interest. Another means of screening and/or selection of peptides useful in the invention is the use of a switchable emulsion, in which peptides active in emulsion stabilization under a first condition are enriched by emulsification with an oil to generate emulsion oil droplets selectively enriched in a coating of peptides capable of emulsion stabilization under a first condition. The oil droplets of the emulsion are then collected and subjected to a second condition, under which the peptide or peptides of interest are not active in emulsion stabilization. Sufficient time is then allowed to elapse for coalescence of the oil droplets stabilized by the peptide or peptides of interest. Optionally, in a second step, the peptide solution enriched after the first selection step is further enriched by emulsification of a mixed peptide solution with an oil to generate emulsion oil droplets enriched in a peptide or peptides still capable of emulsion stabilization under a second condition. The oil droplets of the second emulsion may then be removed to leave behind a second enriched peptide solution that is enriched in a peptide or peptides capable of stabilizing an emulsion under a first condition but not under a second condition. Selection steps of a similar nature may be repeated a multiplicity of times to obtain a peptide solution with desired enriched properties. This solution may be used directly for a particular application, or may be subject to further analysis to determine the sequence of the peptide or combination of peptides responsible for the observed stabilization and destabilization of emulsification activity, to permit direct synthesis of the peptide or combination of peptides of interest.

The peptides useful in the invention and the amino acid residues in the peptides, whether identified by rational design, modification of peptides known in the natural world or identified by screening and/or selection, may be modified during identification or after identification to enhance their properties such as interaction with the interface or other peptides or stability of peptide secondary structure. For example, the N-terminus or C-terminus of a peptide may be modified or a side chain of an amino acid residue within the peptide may be modified. Examples of suitable N-terminus modification include, but are not limited to, acylation with a carboxylic acid containing a straight chain or branched alkyl group or an aryl group. Suitable alkyl groups include, but are not limited to, methyl, ethyl, propyl, isopropyl, butyl, isobutyl, pentyl, hexyl, heptyl, octyl, nonyl, decyl, dodecyl, tetradecyl, hexadecyl and octadecyl. The free amino group at the N-terminus of the peptide may also be modified by addition of other modifying groups known in the art, including, but not limited to, formyl or benzoxycarbonyl groups. Modification of the N-terminus by acylation with a carboxylic acid containing a suitable hydrophobic group may allow enhanced affinity of the peptide for a fluid interface. The free amino group of the peptide may also be modified with additional functional moieties such as metal-binding, fluorescent, or spectroscopically or biologically active species, by using suitably activated derivatives of molecules such as aminocoumarin, biotin, fluorescein, diethylenetriaminepentaacetate, hydrazinonicotinamide or 4-methyl-coumaryl-7-amide, thus providing additional functionality to the peptide.

Examples of suitable C-terminus modification include, but are not limited to, amidation with ammonia or an amine containing a straight chain or branched alkyl group or aryl group or esterification with an alcohol containing straight chain or branched alkyl group or with a phenol or aromatic alcohol. Suitable alkyl groups include, but are not limited to, methyl, ethyl, propyl, isopropyl, butyl, isobutyl, pentyl, hexyl, heptyl, octyl, nonyl, decyl, dodecyl, tetradecyl, hexadecyl and octadecyl. Modification of the C-terminus by amidation with an amine containing a suitable hydrophobic group may allow enhanced affinity of the peptide for a fluid-fluid interface. The free carboxylate group at the C-terminus of the peptide may also be modified by addition of other modifying groups known in the art, including but not limited to, N-oxysuccinimide.

Side chain carboxylate groups of amino acid residues within the peptide, for example the side chain carboxylates of aspartate or glutamate residues, may also be modified by amidation with ammonia or an amine containing a straight chain or branched alkyl group or aryl group or by esterification with an alcohol containing a straight chain or branched alkyl group, a phenol or an aromatic alcohol. Suitable alkyl groups include, but are not limited to, methyl, ethyl, propyl, isopropyl, butyl, isobutyl, pentyl, hexyl, heptyl, octyl, nonyl, decyl, dodecyl, tetradecyl, hexadecyl and octadecyl. Modification of side chain carboxylate groups of amino acid residues within the peptide by esterification or amidation with a carboxylic acid or amine containing a suitable hydrophobic group may allow enhanced affinity of the peptide for a fluid-fluid interface.

Side chain alcohol or phenol groups of amino acid residues within the peptide, for example side chain alcohol or phenol groups of serine, threonine or tyrosine residues, may also be modified by esterification with a carboxylic acid containing a straight chain or branched alkyl group or aryl group. Suitable alkyl groups include, but are not limited to, methyl, ethyl, propyl, isopropyl, butyl, isobutyl, pentyl, hexyl, heptyl, octyl, nonyl, decyl, dodecyl, tetradecyl, hexadecyl and octadecyl. Modification of side chain alcohol or phenol groups of amino acid residues within the peptide by esterification with a carboxylic acid containing a suitable hydrophobic group may allow enhanced affinity of the peptide for a fluid interface. Side chain alcohol or phenol groups of amino acid residues within the peptide may also be reversibly modified by enzymatic or chemical phosphorylation, thus altering the charge on the peptide, as well as the ability of the peptide to bind certain metal ions.

Side chain free amino groups of amino acid residues within the peptide, for example side chain free amino groups of lysine residues, may also be modified by esterification with a carboxylic acid containing a straight chain or branched alkyl group or aryl group. Suitable alkyl groups include, but are not limited to, methyl, ethyl, propyl, isopropyl, butyl, isobutyl, pentyl, hexyl, heptyl, octyl, nonyl, decyl, dodecyl, tetradecyl, hexadecyl and octadecyl. Modification of side chain free amino groups of amino acid residues within the peptide by esterification with a carboxylic acid containing a suitable hydrophobic group may allow enhanced affinity of the peptide for a fluid-fluid interface.

Side chain free thiol groups of amino acid residues within the peptide, including but not limited to side chain thiol groups of cysteine residues, may also be modified by esterification with a carboxylic acid containing a straight chain or branched alkyl group or aryl group. Suitable alkyl groups include, but are not limited to, methyl, ethyl, propyl, isopropyl, butyl, isobutyl, pentyl, hexyl, heptyl, octyl, nonyl, decyl, dodecyl, tetradecyl, hexadecyl and octadecyl. Modification of side chain thiol groups of amino acid residues within the peptide by esterification with a carboxylic acid containing a suitable hydrophobic group may allow enhanced affinity of the peptide for a fluid interface.

The principles governing the structure and interaction of peptides in bulk aqueous solution have been described in the literature, for example, in the case of α-helical peptides including coiled-coil peptides (Andrews and Tabor, 1999, Kohn and Hodges, 1998, Cohen and Parry, 1990, Hill et al., 2000, DeGrado, 2001) and for β-sheet peptides (De Alba et al., 1999, Zhang and Altman, 1999, Hong et al., 2003, Fung et al., 2003, Wang et al., 2005). Principles governing the interactions of peptides with metal ions and the effects of metal ion binding on peptide structures are also described in the literature (Regan, 1995, DeGrado et al., 1999b), and principles governing the structures adopted by peptides composed of β-amino acid residues are being studied (DeGrado et al., 1999a). Some studies on peptide structures at fluid-fluid interfaces have also recently become available (Xu et al., 2004, Sneer et al., 2004, Kerth et al., 2004, Rapaport et al., 2002, Xu et al., 2001, Rapaport et al., 2000). In obtaining peptides useful in the invention, the principles used in designing peptide structures in bulk solution are modified for application to the design of interacting peptide structures at fluid-fluid interfaces. In designing sequences of peptides useful in the invention, either de novo or by modification of a sequence from the natural world, or for interaction with a screening and/or selection process, the following design principles are applied:

i) The peptide should have an amphipathic character, such that a portion of the peptide structure will have a hydrophobic character, and another portion of the peptide structure will have a hydrophilic character, thus imparting to the peptide an affinity for a fluid-fluid interface, such as an air-water or oil-water interface, where one phase possesses a hydrophobic character and the other phase possesses a hydrophilic character. Thus, in the presence of a fluid-fluid interface of this kind, the peptide is capable of adsorbing to form a self-assembled interfacial peptide ensemble.

In some cases, amphipathic properties of the peptide, such as the balance between hydrophobic and hydrophilic properties, may be modulated by protonation or deprotonation of ionizable residues, thus modulating the affinity of the peptide for the interface. For example, in a protonated state, a glutamic acid or aspartic acid residue has a partly hydrophobic character, while in a deprotonated state, the same residue has a more strongly hydrophilic character. Similarly, in a deprotonated state, a lysine residue has a partly hydrophobic character, while in a protonated state, the same residue has a more strongly hydrophilic character. The amphipathic character of a peptide containing these residues can thus be altered simply by changing pH, thus altering the affinity of the peptide for the interface. In some cases, reduction in the affinity of the peptide for the interface by this means may cause weakening or abolition of force transmission in a self-assembled, force-transmitting peptide network at a fluid-fluid interface.

ii) In preferred embodiments, the peptide forms a peptide ensemble composed of monomers capable of assuming an ordered secondary structure at the fluid-fluid interface so that more readily predictable and modulable peptide interactions can be formed between peptides. In some cases, the peptide may also form an ordered secondary structure in aqueous solution. In the most preferred embodiments, the ordered secondary structure at the fluid-fluid interface will be an α-helical structure or a β-sheet structure, and the peptide design will be generated to be consistent with the desired secondary structure at an interface.

Examples of design of amphipathic peptides having an ordered secondary structure are given below:

a. For α-amino acid residues in α-helical or β-sheet secondary structures of peptides, the periodicity of residue positioning is determined by the patterns of hydrogen-bonding between amide bonds in the peptide backbone. In the case of a peptide composed of α-amino acid residues, an α-helix has a periodicity of 3.6 amino acids per helical turn. Thus, for an α-helical secondary structure, repeating hydrophobic residues occurring three or four residues apart within the peptide sequence will be positioned on a single face of the α-helix and hence generate a hydrophobic face to the α-helical structure. The resulting α-helix is an amphipathic α-helix, in which the hydrophobic face of the helix will possess an affinity for the oil or air phase of an oil-water interface or air-water interface, respectively. A table (Table 3, taken from Jones and Middelberg (Jones and Middelberg, 2002b)) showing a scale of hydrophobicity for the twenty naturally occurring α-amino acid residues is given below.

TABLE 3

| amino acid | charge | hydrophobicity | secondary structure formation | |
| --- | --- | --- | --- | --- |
| | | | α-helix | β-sheet |
| alanine | | 0.616 | 1.45 | 0.97 |
| cysteine | | 0.680 | 0.77 | 1.30 |
| aspartate | − | 0.028 | 0.98 | 0.80 |
| glutamate | − | 0.043 | 1.53 | 0.26 |
| phenylalanine | | 1.000 | 1.12 | 1.28 |
| glycine | | 0.501 | 0.53 | 0.81 |
| histidine | + | 0.165 | 1.24 | 0.71 |
| isoleucine | | 0.943 | 1.00 | 1.60 |
| lysine | + | 0.283 | 1.07 | 0.75 |
| leucine | | 0.943 | 1.34 | 1.22 |
| methionine | | 0.738 | 1.20 | 1.67 |
| asparagine | | 0.236 | 0.73 | 0.65 |
| proline | | 0.711 | 0.59 | 0.62 |
| glutamine | | 0.251 | 1.17 | 1.23 |
| arginine | + | 0.000 | 0.79 | 0.90 |
| serine | | 0.359 | 0.79 | 0.72 |
| threonine | | 0.450 | 0.82 | 1.20 |
| valine | | 0.825 | 1.14 | 1.65 |
| tryptophan | | 0.878 | 1.14 | 1.19 |
| tyrosine | | 0.880 | 0.61 | 1.29 |

For the purposes of the invention, a preferred subclass of peptide sequences having a suitable pattern of hydrophobic and hydrophilic residues for the generation of amphipathic α-helices are peptide sequences having a repeating sequence unit (abcdefg) (where n is an integer from 2 to 12, preferably from 2 to 6, more preferably from 2 to 5). In the repeating unit (abcdefg), referred to as a heptad, residues a and d are hydrophobic residues. These hydrophobic residues can interact with other hydrophobic moieties, such as the air phase of an air-water or the oil phase of an oil-water interface, or may also interact with a hydrophobic structure formed by another peptide. Some of these peptides form coiled-coil structures formed in bulk solution by self-association of identical or non-identical peptides, where residues a and d form a hydrophobic core structure (FIG. 1). Although coiled-coil structures are formed in bulk solution, this structure is not necessarily maintained at the fluid-fluid interface. However, such amphipathic α-helical peptides are suitable peptides for use in the present invention as their amphipathic structure provides an affinity for the fluid-fluid interface. As an example, peptide having SEQ ID NO:14 was designed to contain the repeating heptad (EISALEK)$_3$ corresponding to (gabcdef)$_3$, in which residue a is the hydrophobic residue isoleucine (I) and residue d is the hydrophobic residue leucine (L). As a further example, peptide having SEQ ID NO:15 was designed to contain the repeating heptad (KISALKE)$_3$ corresponding to (gabcdef)$_3$, in which residue a is the hydrophobic residue isoleucine (I) and residue d is the hydrophobic residue leucine (L).

Figure 3:
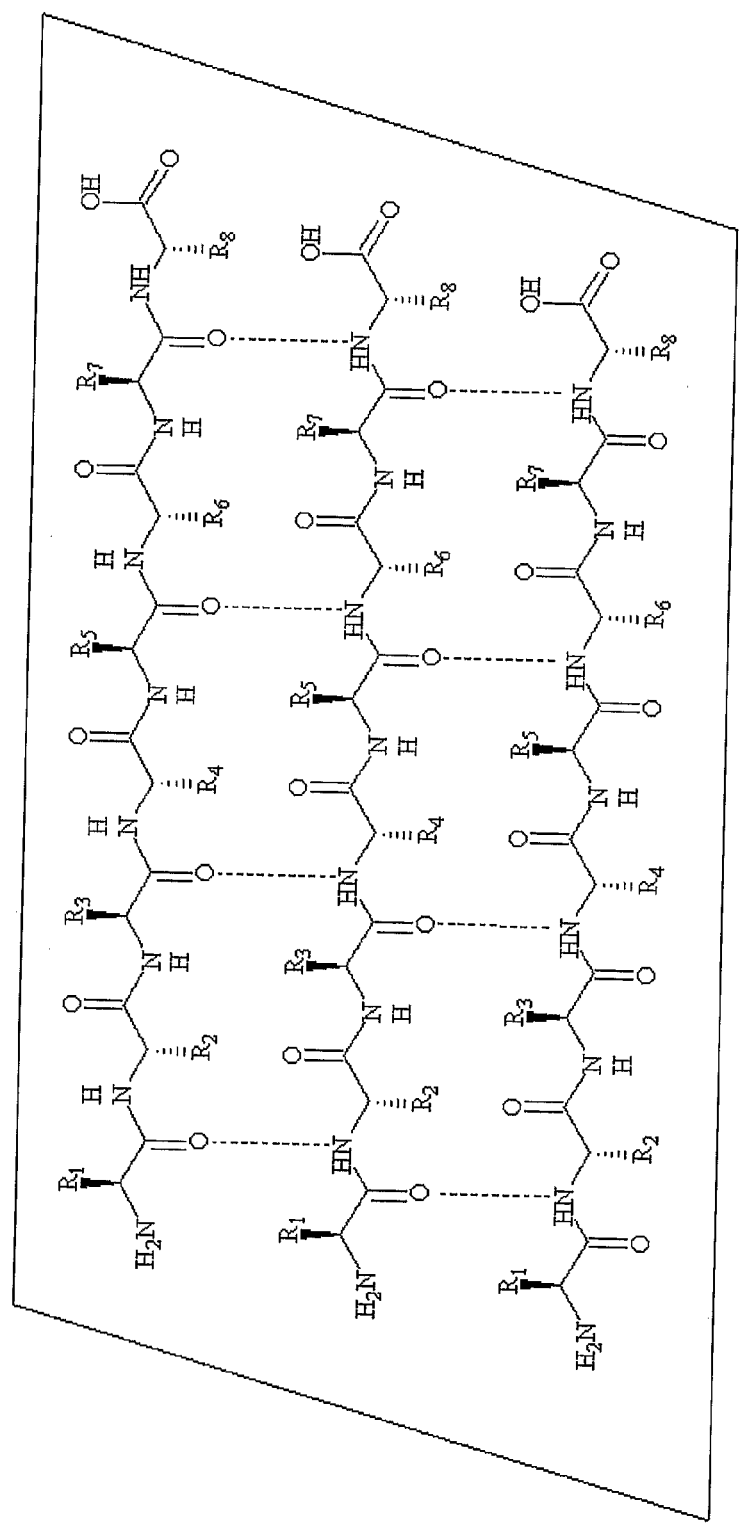
FIG. 3 is a diagrammatic representation of possible interactions between monomeric peptide β-strands at an interface, illustrated for the case of a peptide having eight α-amino acid residues and uncapped N- and C-termini. Three identical peptide molecules are shown interacting at the interface in parallel orientation. The plane of the interface is indicated schematically by the box surrounding the peptide molecules. An anti-parallel orientation of the peptides would also be possible. Potential interactions and repulsions between amino acid side chains can be analysed for an anti-parallel orientation of adjacent peptide molecules using similar principles to those applied here for a parallel orientation of adjacent peptide molecules. The residue side chains in alternating positions along the peptide chain and designated by $R_{odd}$ (i.e. $R_1$, $R_3$, $R_5$ and $R_7$) are hydrophobic residue side chains. The solid wedged bonds indicate that these side chains project above the plane of the interacting peptide β-strands, into the hydrophobic interface. The residue side chains in alternating positions along the peptide chain and designated by $R_{even}$ (i.e. $R_2$, $R_4$, $R_6$ and $R_8$) are hydrophilic residue side chains. The dashed wedged bonds indicate that these side chains project below the plane of the interacting peptide β-strands, into the aqueous phase. The dashed bonds between >C=O and —NH— groups on adjacent peptide molecules indicate hydrogen bonds between the peptide backbones of adjacent peptide molecules in the interface. Interaction or repulsion between side chains of adjacent peptide molecules ($R_{odd}$ with $R_{odd}$, or $R_{even}$ with $R_{even}$), or interaction or repulsion between side chains within a single peptide molecule ($R_{odd}$ with $R_{odd}$, or $R_{even}$ with $R_{even}$), may serve to modulate the strength of the peptide network. In addition, interaction exists between adjacent peptide molecules in the interface based on hydrogen bonds.

It is envisaged that other α-helical sequence designs, not fitting the pattern of a repeating heptad (abcdefg)$_n$, may be generated in which network formation by helical peptides adsorbed at a fluid-fluid interface can be manipulated in a manner similar to that described here. All such peptides are intended to be included within the scope of this invention.

b) In the case of a β-sheet structure, a β-sheet has a usual form that projects the side chains of alternate α-amino acid residues within the sequence above or below a β-sheet structure, where adjacent peptide β-strands within the β-sheet are bound to each other by hydrogen bonds (FIG. 3). Correspondingly, within a β-sheet structure, hydrophobic residues occurring alternately within the peptide sequence will generate a hydrophobic face to a β-strand within the β-sheet structure, thus generating an amphipathic β-strand structure. Table 3 shows a scale of hydrophobicity for the twenty naturally occurring α-amino acid residues. Examples of peptides having alternating hydrophobic and hydrophilic residues include peptides having SEQ ID NO:6 (9 amino acid residues in length, containing alternating hydrophobic residues, proline (P) and phenylalanine (F) and hydrophilic residues histidine (H), arginine (R) and serine (S)); SEQ ID NO:7 (9 amino acid residues in length, containing alternating hydrophobic residues proline (P) and phenylalanine (F) and hydrophilic residues histidine (H) and serine (S)); SEQ ID NO:8 (9 amino acid residues in length, containing alternating hydrophobic residues proline (P) and phenylalanine (F) and hydrophilic residues arginine (R) and serine (S)); SEQ ID NO:11 (9 amino acid residues in length, containing alternating hydrophobic residues proline (P) and phenylalanine (F) and hydrophilic residues histidine (H) and serine (S)); and SEQ ID NO:12 (9 amino acid residues in length, containing alternating hydrophobic residues proline (P) and phenylalanine (F) and hydrophilic residues histidine (H) and serine (S)).

As used herein the term "β-sheet structure" refers to a peptide secondary structure comprising linear peptide segments bound together by intramolecular or intermolecular hydrogen bonding to provide a substantially planar structure. A β-sheet structure may also be defined by a range of angles of rotation around the peptide bonds existing within the peptide structure, such as those defined by a Ramachandran plot. A β-sheet structure may be formed from a single peptide which undergoes folding to provide antiparallel sequences of residues bound together by hydrogen bonding. A β-sheet structure may also be formed from two or more separate linear peptide molecules which are aligned in a parallel or antiparallel manner and interact with one another by hydrogen bonding.

c) As the tendency of a given peptide sequence to adopt an α-helical or β-sheet structure is influenced by the α-helical or β-sheet propensities of individual residues, amino acid residues should be chosen which are consistent with the desired ordered structure of the peptide at the interface. Certain amino acid residues, such as alanine and glutamate, prefer to be present within an α-helical structure, while other amino acid residues, such as isoleucine and methionine, prefer to be present within a β-sheet structure (Table 3). Other residues, such as aspartate, as indicated by neutral values between 0.8 and 1.0 in the right-hand two columns of Table 3, do not have a strong preference for either structure. Other residues, such as proline, prefer not to be present in either α-helical or β-sheet structures, and serve as secondary structure "breakers" at the termini of ordered peptide secondary structures. In addition, the preference of a particular amino acid residue to be present within either an α-helical or a β-sheet structure may be influenced by the position of the amino acid residue within the peptide sequence (Cochran and Doig, 2001, Cochran et al., 2001, Cohen and Parry, 1990, Kohn et al., 1997a).

d) Peptides that lack a defined secondary structure may also be useful in the invention if they have or can be induced to have a hydrophobic portion to interact with the interface, a hydrophilic portion to interact with the bulk solution of peptide and upon self-assembly at the fluid-fluid interface, can interact with adjacent peptides to form a network and that the chemical and/or physical properties of the peptide may be modulated by stimuli. It is likely that suitable peptides lacking defined secondary structure, or having structure different to that discussed in i) to v) above, would initially be identified using screening and/or selection techniques.

iii) The peptides in the interfacial peptide ensemble are at a sufficient concentration at the fluid-fluid interface and are able to interact with one another, under a first condition, with sufficient strength to create a self-assembled, force-transmitting peptide network, and iv) The interaction between peptides in the self-assembled, force-transmitting peptide network is capable of modulation under a second condition in such a manner as to lead to weakening or dissipation of the network.

Figure 2:
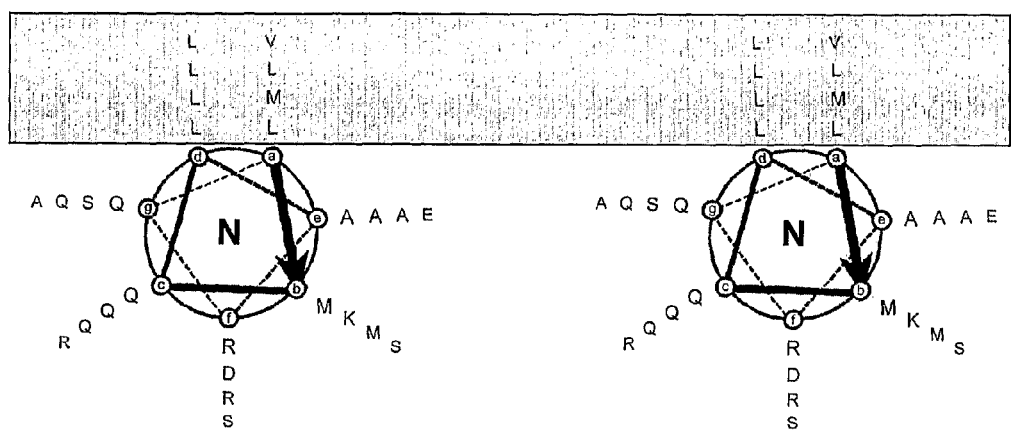
FIG. 2 is a diagrammatic representation of interactions between monomeric peptide α-helices at an interface, illustrated for the case of peptide having SEQ ID NO:3, which contains four heptad repeats abcdefg. The peptides are shown in parallel orientation. An anti-parallel orientation would also be possible. For visual clarity, the residue alignments along the helix are shown as corresponding to a helical periodicity of 3.5 residues per turn, rather than 3.6 residues per turn. The shaded bar at the top of the diagram indicates an idealised fluid-fluid interface, such as an air-water or oil-water interface, of finite depth. The shaded bar is not intended to indicate the true width or position of the interface relative to the dimensions of the molecule. The amphipathic peptide helices interact with the hydrophobic portion of the interface primarily via the side chains of hydrophobic residues located at positions a and d of the heptad repeat of the peptide and locate at the interface because of their dual hydrophilic and hydrophobic nature. The upper arrow indicates intermolecular interactions and/or repulsions between adjacent peptide molecules in the interface, mediated by the side chains of residues located at positions e and g of the heptad repeat. The lower arrow indicates intermolecular interactions and/or repulsions between adjacent peptide molecules in the interface, mediated by the side chains of residues located at positions b and c of the heptad repeat.

Principles for the formation and modulation of interactions between peptides in the peptide network are illustrated here using examples based on peptide networks formed from peptides having either a heptad-based α-helical structure, or a β-sheet structure, at the fluid-fluid interface:

In the case of amphipathic α-helical peptide sequences having a repeating sequence unit (abcdefg), residues e and g on adjacent peptide molecules participate in intermolecular interactions that may stabilize the network, for example, hydrophobic interactions, hydrogen bonding interactions, metal-bridging interactions, or attraction between oppositely charged residues (FIG. 2, upper arrow, illustrated for the case of peptide having SEQ ID NO:3). As an example, peptide having SEQ ID NO:14 was designed to contain the repeating heptad (EISALEK)$_3$ corresponding to (gabcdef)$_3$, in which residues e and g are the acidic residue glutamic acid (E). Under suitably acidic conditions where the glutamic acid residues bear no charge at the interface, glutamic acid residues e and g are expected to promote intermolecular interactions by means of hydrogen bonding as well as interactions between hydrophobic methylene groups within the glutamic acid side chain. Further, glutamic acid residues e and g may be able to participate in metal ion bridging interactions between peptide molecules. As a further example, peptide having SEQ ID NO:15 was designed to contain the repeating heptad (KISALKE)$_3$ corresponding to (gabcdef)$_3$, in which residues e and g are the basic residue lysine (K). Under suitably basic conditions where the lysine residues bear no charge at the interface, lysine residues e and g are expected to promote intermolecular interactions by means of hydrogen bonding as well as interactions between hydrophobic methylene groups within the lysine side chain. Further, lysine residues e and g may be able to participate in metal ion bridging interactions between peptide molecules. Alternately, intermolecular repulsions between e and g residues on adjacent peptide molecules may destabilize the network, for example by electrostatic repulsion. As an example, peptide having SEQ ID NO:14 was designed to contain the repeating heptad (EISALEK)$_3$ corresponding to (gabcdef)$_3$, in which residues e and g are the acidic residue glutamic acid (E). Under suitably basic conditions where the glutamate residues bear a negative charge at the interface, glutamate residues e and g, in the absence of bridging metal ions, are expected to participate in intermolecular charge-charge repulsions. As a further example, peptide having SEQ ID NO:15 was designed to contain the repeating heptad (KISALKE)$_3$ corresponding to (gabcdef)$_3$, in which residues e and g are the basic residue lysine (K). Under suitably acidic conditions where the lysine residues bear a positive charge at the interface, lysine residues e and g are expected to participate in intermolecular charge-charge repulsions. A person skilled in the art will be able to design interactions and/or repulsions between e and g residues in a given peptide or combination of two or more peptides to as to manipulate the strength and switchability of a network containing these peptides.

In addition, in these structures, residues b and c on adjacent peptide molecules participate in intermolecular interactions that may stabilize the network, for example, hydrophobic interactions, hydrogen bonding interactions, metal-bridging interactions, or attraction between oppositely charged residues (FIG. 2, lower arrow, illustrated for the case of peptide having SEQ ID NO:3). As an example, peptide having SEQ ID NO:9 was designed, by modification of a sequence known in the natural world, to contain repeating heptads in which residues b and c are the acidic residue glutamic acid (E). Under suitably acidic conditions where the glutamic acid residues bear no charge at the interface, glutamic acid residues b and c are expected to promote intermolecular interactions by means of hydrogen bonding as well as interactions between hydrophobic methylene groups within the glutamic acid side chain. Further, glutamic acid residues b and c may be able to participate in metal ion bridging interactions between peptide molecules. As a further example, peptide having SEQ ID NO:10 was designed, by modification of a sequence known in the natural world, to contain repeating heptads in which residues b and c are the basic residue lysine (K). Under suitably basic conditions where the lysine residues bear no charge at the interface, lysine residues b and c are expected to promote intermolecular interactions by means of hydrogen bonding as well as interactions between hydrophobic methylene groups within the lysine side chain. Further, lysine residues b and c may be able to participate in metal ion bridging interactions between peptide molecules. Alternately, intermolecular repulsions between b and c residues on adjacent peptide molecules may destabilize the network, for example by electrostatic repulsion. As an example, peptide having SEQ ID NO:9 was designed, by modification of a sequence known in the natural world, to contain repeating heptads in which residues b and c are the acidic residue glutamic acid (E). Under suitably basic conditions where the glutamic acid residues bear a negative charge at the interface, glutamic acid residues b and c are expected to participate in intermolecular charge-charge repulsions. As a further example, peptide having SEQ ID NO:10 was designed, by modification of a sequence known in the natural world, to contain repeating heptads in which residues b and c are the basic residue lysine (K). Under suitably acidic conditions where the lysine residues bear a positive charge at the interface, lysine residues b and c are expected to participate in intermolecular charge-charge repulsions. A person skilled in the art will be able to design interactions and/or repulsions between b and c residues in a given peptide or combination of two or more peptides to as to manipulate the strength and switchability of a network containing these peptides.

Although the interactions described above may be effective when the peptides are aligned so that two N-termini and two C-termini are adjacent to one another, it is also envisaged that throughout the peptide network, the peptides may be aligned in an anti-parallel fashion or may be offset so that, for example, the N-terminal residues of a peptide may interact with adjacent amino acid residues in the centre of or at the C-terminal end of an adjacent peptide. The peptides may self-assemble at the fluid-fluid interface in an aligned or non-aligned manner with sufficient interaction with adjacent peptides to allow network formation.

In addition, it is envisaged that stabilization of an ordered secondary structure at the interface may increase the strength of a self-assembled, force-transmitting peptide network. Modulation of the stability of an ordered secondary structure, such as an α-helical or a β-sheet structure, may be achieved by various means, including but not limited to alteration of the interaction of charged residues within the peptide sequence, alteration of the length of the peptide sequence, or alteration of the pattern of hydrophobic and hydrophilic residues within the peptide sequence.

In bulk solution, the stability of an α-helical or a β-sheet structure in bulk solution is affected by the pattern of charge-charge interactions or repulsions within or between peptide molecules (Vu et al., 2001, Bosshard et al., 2004, Kohn et al., 1997a, Kohn et al., 1995, Yu et al., 1996, Krylov et al., 1998, Marti and Bosshard, 2003, Kohn et al., 1997b, Huyghues Despointes and Baldwin, 1997, Jelesarov et al., 1998). It is believed that the stability of the peptide secondary structure at an interface is affected by sequence charge patterns in a similar manner to the stability of the peptide secondary structure in bulk solution. For example, in an α-helical structure, hydrophilic residues, such as those typically present in b, c, e, f or g positions of repeating heptad sequences, occurring three or four residues apart within the peptide sequence will be spatially positioned on a single face of the α-helix, and may participate in intermolecular interactions that stabilize the α-helical structure, for example, hydrophobic interactions, hydrogen bonding interactions, metal-bridging interactions, or attraction between oppositely charged residues. For example, residues in an f position might participate in stabilizing interactions with residues in a b or c position in a preceding or following turn of an α-helix. As an example, peptide having SEQ ID NO:4 was designed, by modification of a sequence known in the natural world, to contain, at two sites, aspartic acid (D) and glutamic acid (E) residues spaced three residues apart (E-3 with D-6, and D-16 with E-19). Under suitably acidic conditions where the aspartic acid and glutamic acid residues bear no charge at the interface, the paired aspartic acid and glutamic acid residues are expected to promote intramolecular interaction by means of hydrogen bonding as well as interactions between hydrophobic methylene groups within the aspartic acid and glutamic acid side chains. Further, under suitable conditions the paired aspartic acid and glutamic acid residues may be able to participate in metal ion bridging interactions within the peptide molecule. As a further example, peptide having SEQ ID NO:5 was designed, by modification of a sequence known in the natural world, to contain, at two sites, histidine (H) residues spaced three or four residues apart (H-9 with H-13, and H-17 with H-20). Under suitably basic conditions where the histidine residues bear no charge at the interface, the paired histidine residues are expected to promote intramolecular interaction by means of hydrogen bonding as well as interactions between hydrophobic groups within the histidine side chain. Further, under suitable conditions, the paired histidine residues may be able to participate in metal ion bridging interactions within the peptide molecule. As a further example, peptide having SEQ ID NO:13 was designed, by modification of a sequence known in the natural world, to contain, at two sites, histidine (H) residues spaced three or four residues apart (H-9 with H-13, and H-17 with H-20). Under suitably basic conditions where the histidine residues bear no charge at the interface, the paired histidine residues are expected to promote intramolecular interaction by means of hydrogen bonding as well as interactions between hydrophobic groups within the histidine side chain. Further, under suitable conditions, the paired histidine residues may be able to participate in metal ion bridging interactions within the peptide molecule. Alternately, hydrophilic residues occurring three or four residues apart within an α-helical structure will be spatially positioned on a single face of the α-helix, and may participate in intramolecular repulsions, for example electrostatic repulsions, that destabilize the α-helical structure. Destabilization of an ordered secondary structure at a fluid-fluid interface may contribute to a reduction in the strength of a self-assembled, force-transmitting peptide network at the interface. As an example, peptide having SEQ ID NO:2 was designed, by modification of a sequence known in the natural world, to contain, at two sites, histidine (H) and arginine (R) residues spaced three or four residues apart (H-9 with R-13, and R-17 with H-20). Under suitably acidic conditions where both the histidine residues and the arginine residues bear a positive charge at the interface, the paired histidine and arginine residues are expected to participate in intermolecular charge-charge repulsions. As a further example, peptide having SEQ ID NO:4 was designed, by modification of a sequence known in the natural world, to contain, at two sites, aspartic acid (D) and glutamic acid (E) residues spaced three residues apart (E-3 with D-6, and D-16 with E-19). Under suitably basic conditions where the aspartic acid and glutamic acid residues bear a negative charge at the interface, the paired aspartic acid and glutamic acid residues are expected to participate in intermolecular charge-charge repulsions. As a further example, peptide having SEQ ID NO:5 was designed, by modification of a sequence known in the natural world, to contain, at two sites, histidine (H) residues spaced three or four residues apart (H-9 with H-13, and H-17 with H-20). Under suitably acidic conditions where the histidine residues bear a positive charge at the interface, the paired histidine residues are expected to participate in intermolecular charge-charge repulsions. As a further example, peptide having SEQ ID NO:13 was designed, by modification of a sequence known in the natural world, to contain, at two sites, histidine (H) residues spaced three or four residues apart (H-9 with H-13, and H-17 with H-20). Under suitably acidic conditions where the histidine residues bear a positive charge at the interface, the paired histidine residues are expected to participate in intermolecular charge-charge repulsions.

Further, in bulk solution, the stability of ordered peptide secondary structures in bulk solution is affected by the length of the peptide sequence (Fairman et al., 1995, De Crescenzo et al., 2003, Su et al., 1994, Litowski and Hodges, 2001, Wang et al., 2004), with the stability of an ordered secondary structure usually, although not always (Kwok and Hodges, 2004), increasing with the length of the peptide sequence and the concentration of peptides. It is believed that the stability of the peptide secondary structure at an interface is affected by sequence length and the interfacial excess concentration of peptide in a similar manner to the stability of the peptide secondary structure in bulk solution. The peptide may be chosen to have a sequence length consistent with good stability under one condition, and diminished stability under a second condition. Preferably the length is chosen to provide a metastable peptide having a balance between stability and instability. For example, in some embodiments, particularly α-helical peptides, the peptide is between 17 and 25 residues in length, especially between 18 and 24, 19 and 23, 20 and 22, more especially 21 residues in length.

Modulation of the stability of an ordered secondary structure, such as an α-helical structure, at an interface, may also be achieved by modulating the balance of hydrophilic and hydrophobic residues. For example, it is possible to design peptides in which an ionizable residue is placed in an a or d position of a heptad repeat normally occupied by a hydrophobic residue. Under conditions of pH where this residue is uncharged at the interface, it may function as a hydrophobic residue. However, under conditions of pH where this residue bears a charge at the interface, the peptide affinity for the interface may be reduced, leading to weakening or dissipation of the network. Alternately, under conditions of pH where this residue bears a charge at the interface, the ordered structure of the peptide at the interface may be disrupted, leading to weakening or dissipation of the network.

In a β-sheet structure containing individual peptide β-strands at a fluid-fluid interface, interaction between spatially adjacent peptide molecules may be strengthened by interaction between the side chains of amino acid residues projecting into the aqueous phase (FIG. 3, $R_{even}$ side chains), for example, by hydrophobic interactions, hydrogen bonding interactions, metal-bridging interactions, or attraction between oppositely charged residues. This is exemplified by peptides having SEQ ID NO:6, SEQ ID NO:7, SEQ ID NO:11 and SEQ ID NO:12 which were each designed to contain histidine residues. Under suitably basic conditions where the histidine residues bear no charge at the interface, histidine residues on spatially adjacent peptide molecules at the interface are expected to promote intermolecular interaction by means of hydrogen bonding as well as interactions between hydrophobic groups within the histidine side chain. Further, the paired histidine residues may be able to participate in metal ion bridging interactions between peptide molecules. Another example includes peptides having SEQ ID NO:6, SEQ ID NO:7, SEQ ID NO:8, SEQ ID NO:11 and SEQ ID NO:12 which were each designed to contain serine residues. Serine residues on spatially adjacent peptide molecules at the interface are expected to promote intermolecular interaction by means of hydrogen bonding as well as interactions between hydrophobic groups within the serine side chain. In addition in a β-sheet structure containing individual peptide β-strands at a fluid-fluid interface, repulsions, for example electrostatic repulsions, between the side chains of amino acid residues projecting into the aqueous phase (FIG. 3, $R_{even}$ side chains) may be generated between spatially adjacent peptide molecules. For example, peptides having SEQ ID NO:6, SEQ ID NO:7, SEQ ID NO:11 and SEQ ID NO:12 were designed to contain histidine residues. Under suitably acidic conditions where the histidine residues bear a positive charge at the interface, histidine residues on spatially adjacent peptide molecules at the interface are expected to participate in intermolecular charge-charge repulsions. As a further example, peptides having SEQ ID NO:6 and SEQ ID NO:8 were designed to contain arginine residues.

Under suitably acidic conditions where the arginine residues on spatially adjacent peptide molecules at the interface bear a positive charge, the arginine residues are expected to participate in intermolecular charge-charge repulsions. Particularly in the case of β-sheet structures, where adjacent peptide strands within the β-sheet structure interact with each other by means of hydrogen bonds to form a cohesive structure, it is envisaged that repulsions, such as electrostatic repulsions, are important in modulating the strength of a self-assembled, force-transmitting peptide network at a fluid-fluid interface.

In addition, in a β-sheet structure containing individual peptide β-strands at a fluid-fluid interface, stabilization of the secondary structure of individual peptide molecules may be increased by intramolecular interaction between the side chains of spatially adjacent amino acid residues projecting into the aqueous phase (FIG. 3, $R_{even}$ side chains, for example $R_2$ with $R_4$, $R_4$ with $R_6$, or $R_6$ with $R_8$) within a single peptide molecule, for example, by hydrophobic interactions, hydrogen bonding interactions, metal-bridging interactions, or attraction between oppositely charged residues. It is envisaged that stabilization of an ordered secondary structure at the interface may increase the strength of a self-assembled, force-transmitting peptide network, particularly in the case of a β-sheet structure where adjacent peptide strands within the β-sheet structure interact with each other by hydrogen bonds to form a cohesive structure. As an example, peptide having SEQ ID NO:11 was designed to contain spatially adjacent histidine (H) residues within the β-strand structure. Under suitably basic conditions where the histidine bears no charge at the interface, paired histidine residues within a peptide molecule at the interface may stabilize the secondary structure of the peptide by means of hydrogen bonding as well as interactions between hydrophobic groups within the serine side chains. Further, the paired histidine residues may be able to participate in metal ion bridging interactions within the peptide molecule. In addition in a β-sheet structure containing individual peptide β-strands at a fluid-fluid interface, repulsions, for example electrostatic repulsions, between the side chains of amino acid residues projecting into the aqueous phase may be generated within a single peptide molecule (FIG. 3, $R_{even}$ side chains, for example $R_2$ with $R_4$, $R_4$ with $R_6$, or $R_6$ with $R_8$). As an example, peptide having SEQ ID NO:11 was designed to contain spatially adjacent histidine (H) residues within the β-strand structure. Under acidic conditions where the histidine residues bear a positive charge, paired histidine residues within a single peptide molecule at the interface are expected to participate in intermolecular charge-charge repulsions, thus destabilizing the β-strand structure. As a further example, peptide having SEQ ID NO:6 was designed to contain spatially adjacent histidine (H) and arginine (R) residues. Under suitably acidic conditions where both the histidine and the arginine residues bear a positive charge at the interface, paired histidine and arginine residues within a single peptide molecule at the interface are expected to participate in intermolecular charge-charge repulsions, thus destabilizing the β-strand structure. Particularly in the case of β-sheet structures, where adjacent peptide strands within the β-sheet structure interact with each other by means of hydrogen bonds to form a cohesive structure, it is envisaged that repulsions, such as electrostatic repulsions, are important in modulating the strength of a self-assembled, force-transmitting peptide network at a fluid-fluid interface.

Modulation of the stability of an ordered secondary structure, such as an β-sheet structure, at an interface, may also be achieved by modulating the balance of hydrophilic and hydrophobic residues. For example, it is possible to design peptides in which an ionizable residue is placed in a position in a β-sheet-forming peptide that would normally interact with the hydrophobic phase (e.g. $R_{odd}$ (i.e. $R_1$, $R_3$, $R_5$ and $R_7$), FIG. 3). Under conditions of pH where this residue is uncharged at the interface, it may function as a hydrophobic residue. Under conditions of pH where this residue bears a charge at the interface, the peptide affinity for the interface may be reduced, leading to weakening or dissipation of the network. Alternately, under conditions of pH where this residue bears a charge at the interface, the ordered structure of the peptide at the interface may be disrupted, leading to weakening or dissipation of the network.

As used herein the term "secondary structure" refers to the conformation adopted by the amino acid residues in a peptide. An "ordered secondary structure" is one in which the amino acid residues adopt a regular conformation for example, as indicated by a defined range of angles of rotation around the peptide bond, such as those defined by a Ramachandran plot. Examples of peptides having an ordered secondary structure include peptides having α-helical structure or those that form part of or all of a β-sheet structure. Peptides that lack an ordered secondary structure have amino acid residues that adopt random conformations.

In preferred embodiments, the peptides capable of participating in a self-assembled, force-transmitting peptide network have an amphipathic structure that allows adsorption at a fluid-fluid interface and have side chains capable of interacting with an adjacent peptide under one set of conditions and capable of not interacting or repelling an adjacent peptide under another set of conditions. Conveniently, the peptides capable of participating in self-assembled force-transmitting peptide networks have an ordered secondary structure, such as an α-helical or β-sheet structure, as this allows more predictable design and placement of amino acid residues to enable interaction with the interface and manipulation of interactions between adjacent peptides within the network or intra-molecular interactions within a peptide participating in the network.

The peptides in the peptide networks may include naturally occurring or non-naturally occurring amino acids and may include α-amino acids and β-amino acids. The amino acids may also have D- or L-configurations. In some embodiments, the amino acids of the peptide are naturally occurring L-α-amino acids.

In a some embodiments, the peptides are about 2 to about 80 amino acid residues in length, usually from about 5 to 60 amino acid residues in length and more usually from about 10 to 40 amino acid residues in length. Illustrative examples of peptides have 10 to 39, 10 to 38, 10 to 37, 10 to 36, 10 to 35, 15 to 34, 15 to 33, 15 to 32, 15 to 31, 15 to 30 or 20 to 30 amino acid residues.

The peptide network may be formed from peptides having the same amino acid sequence or mixtures of peptides having more than one different amino acid sequence. In some embodiments, the peptides forming the network have the same amino acid sequence and thus form a 'homogeneous peptide network'. In other embodiments two or more different peptides form a 'heterogeneous peptide network'.

Methods of Modulating Interfacial Characteristics

In one aspect, the present invention provides methods of modulating interfacial characteristics in a self-assembled, force-transmitting peptide network at a fluid-fluid interface. These methods generally comprise exposing a peptide capable of participating in a self-assembled, force-transmitting peptide network, either before or after it interacts with other peptides to form the peptide network, to a stimulus that alters the chemical and/or physical properties of the peptide.

The self-assembled, force-transmitting peptide network is an ensemble comprising a plurality of peptides that interact with one another with sufficient strength to allow transmission of force when interfacial stress is applied to the network. The peptide network is formed by self-assembly where peptides in a bulk solution have an affinity for the fluid-fluid interface and therefore migrate to the interface to provide an interfacial concentration of peptide sufficient to allow adjacent peptides to interact with sufficient strength to form a network. In some embodiments, the peptides cover at least 10% of the fluid-fluid interface, especially at least 20% and more especially at least 25% of the fluid-fluid interface. In preferred embodiments, the peptides cover at least 40%, especially at least 50% or at least 60% and more especially at least 80% of the fluid-fluid interface. In some embodiments, the peptide coverage at the fluid-fluid interface is a concentration referred to as $\Gamma$max, where $\Gamma$max is the mass of peptide per area of interface at saturation and is thus the maximum load of peptide in a given ensemble. In some embodiments peptide coverage is greater than 10% of $\Gamma$max, especially greater than 25% of $\Gamma$max, more especially greater than 50% $\Gamma$max.

The peptides in the peptide network may be any peptides that have an affinity for the fluid-fluid interface and a capacity for interaction with other peptides. Preferred peptides have a hydrophobic region which is attracted to the interface and a hydrophilic region which is attracted to the hydrophilic phase; both regions are capable of forming associations or interactions with other peptides depending on the physical and chemical state of the peptides in a given ensemble. Alternatively, the peptides may interact by short-range solvation forces such as hydration, hydrophobic interactions, osmotic attractive potential due to exclusion of ions, surface charge interactions or bridging by non-peptide species such as metal ions or organic molecules bearing a charge complementary to compounds of the peptide network. The peptides may have a helical conformation, a β-sheet conformation, a random conformation or a mixture thereof. In some embodiments, the peptides have an ordered structure such as a helical conformation or a β-sheet and they self-assemble at the interface into an ensemble having order.

The peptides preferably have a number of regions which are capable of interacting with other peptides, for example, hydrophilic regions, hydrophobic regions, amino acid residues with a side chain functional group capable of interacting with another peptide for example, by hydrogen bonding, ion pair interactions and metal ion bridging. For example, amino acid residues capable of participating in hydrogen bonding, ion-pair interactions, hydrophobic interactions and other solvation interactions, dipole interactions, salt bridge formation or covalent cross-linking. Amino acid residues capable of participating in hydrogen bonding include those with amino, hydroxy, carboxy or thiol functional groups. Amino acid residues capable of participating in ion pair interactions include those which have charged functional groups at an appropriate pH, for example, carboxylic acids, imidazole, amino groups, thiol groups, hydroxy groups and guanidino groups. Amino acid residues capable of participating in hydrophobic interactions have hydrophobic side chains and include amino acid residues such as alanine, isoleucine, leucine, phenylalanine, tryptophan, tyrosine and valine or may have hydrophobic regions in their side chains, such as methylene groups of lysine, arginine, glutamatic acid, glycine or aspartic acid residues. Amino acid residues capable of participating in dipole interactions include those with polar functional groups such as guanidino, carboxy, amido, amino, thiol and hydroxy groups. Amino acid residues that are capable of forming covalent cross-linking are those that can form covalent bonds, for example disulfide bonds formed from cysteine residues.

The stimulus that alters the chemical and/or physical properties of the peptide can be any stimulus that alters the ability of the peptides within the peptide network to participate in interactions with one another or that stabilizes or destabilizes the conformation of a peptide or the spatial arrangement of the peptides within the network or that increases or reduces the affinity of the peptide for the fluid-fluid interface or that increases or reduces the rate of network formation. The stimulus may cause the attractive interactions between peptides in the network to be strengthened or may cause the attractive interactions between peptides in the network to be weakened. In some cases the stimulus may cause the attractive interactions between peptides in the network to be abolished thereby causing the intermolecular peptide interactions within the peptide network to dissipate upon exposure to the stimulus or form a peptide ensemble that is not capable of transmitting significant force.

The stimulus that alters the chemical and/or physical properties of the peptide may alter the spatial arrangement of substituent groups on the peptide. For example, the introduction of metal ions may cause the formation of metal ion bridges between the two negatively charged amino acid residues or two amino acid residues having negative dipoles within a peptide and cause stabilization of a peptide conformation such as an α-helical peptide conformation. Stabilization of an α-helical conformation, or a β-sheet conformation within a peptide may allow a more ordered peptide network to be formed resulting in stronger or closer interactions between peptides, Alternatively, metal ions may cause the formation of metal ion bridges between two negatively charged amino acid residues or two amino acid residues having negative dipoles, where the amino acid residues are on different peptides within the peptide network. Metal ion bridges formed between different peptides within the peptide network, strengthen the peptide network to form a stronger peptide network having a higher elastic modulus. Suitable metal ions include any metal ions or combination of metal ions able to form bridges within a peptide or between different peptide molecules. Illustrative examples of suitable metal ions include, but are not limited to, magnesium ions and calcium ions, transition metal ions such as titanium ions, vanadium ions, chromium ions, manganese ions, iron ions, cobalt ions, nickel ions, copper ions, zinc ions and molybdenum ions, and lanthanide ions such as lanthanum ions, cerium ions, praseodynium ions, neodynium ions, promethium ions, samarium ions, europium ions, gadolinium ions, terbium ions, dysprosium ions, holmium ions, erbium ions, thulium ions, ytterbium ions and lutetium ions. In some cases, changes in the oxidation state of the metal may alter the force transmission of a metal ion containing peptide network.

Conversely, the addition of metal ion chelators will bind metal ions in the bulk peptide solution and prevent metal ion bridges forming within a peptide or between peptides in a peptide network or may remove metal ions from metal ion bridges within a peptide or between peptides in a peptide network. A metal ion chelator may therefore weaken the interactions between peptides by destabilizing peptide conformation and/or reducing interactions between peptides. The metal ion chelators may scavenge adventitious metal ions present in the bulk solution or dispersion from which the peptide network is formed.

Alternatively, the metal ion chelators may scavenge metal ions that have been previously added to strengthen the interactions with a peptide or between the peptides of the peptide network. Suitable chelating agents are those which are soluble in the bulk peptide solution from which the peptide network is formed and/or may be selected for suitability or ability to bind a particular metal ion. For example, suitable chelating agents include, but are not limited to, ethylenediamine, ethylenetriamine, triethylenetetramine, ethylenediaminetetraacetic acid (EDTA), aminoethanolamine, ethylene glycol bis(2-aminoethyl ether)-N,N,N'N'-tetraacetic acid (EGTA), tris(2-imidazolyl)carbinol, tris[4(5)-imidazolyl] carbinol, bis[4(5)-imidazolyl]glycolic acid, oxaloacetic acid, citric acid, glycine or other amino acids, salicylate, macrocyclic ethers, multidentate Schiff bases, acetylacetone, bis (acetylacetone) ethylenediimine, 2-nitroso-1-naphthol, 3-methoxyl-2-nitrosophenol, cyclohexanetrione trioxime, diethylenetriaminepentaacetic acid (DTPA), N-(hydroxyethyl)ethylenediaminetriacetic acid (HEDTA), tripolyphosphate ion, nitrilotriacetic acid, dimethylglyoxime, dimercaprol, deferoxamine.

In addition, a metal ion may be removed from interaction with a peptide by addition of an ion with which the metal ion forms an insoluble salt. Suitable ions include, but are not limited to, phosphate ions, borate ions, sulfide ions, arsenate ions, and chloride ions. In addition, in some cases a metal ion may be precipitated as a hydroxide by an increase in pH. The effect is removal of the metal ion by precipitation.

In addition, a metal ion may be removed from interaction with a peptide by addition of a solid substance, such as a resin, which is able to bind metal ions.

In an alternative embodiment, the binding of a metal ion may give rise to a local positive charge which could interact with a nearby positive charge, or may neutralize a negative charge which previously stabilized an ordered conformation, or may cause the average positive charge on a peptide to deviate significantly from zero generating charge-charge repulsions. In these cases, the binding of a metal ion may destabilize the peptide network causing weakening or dissipation of the network and the addition of a chelating agent may stabilize the peptide network by scavenging adventitious metal ions that may cause destabilization.

The stimulus that alters the chemical and/or physical properties of the peptide may alter the charge of substituent groups on a peptide. If two substituents having like charge are in close spatial proximity the two substituents will repel one another and destabilize the conformation of a peptide or the interaction between peptides. For example, at basic pH depending on the ionization constant of the group, an amino group, guanidino group or imidazole group will not have a charge, but at a suitably acid pH depending on the ionization constant of the group, such groups will accept a proton and become charged. For example, at high pH, the imidazolyl group of histidine is uncharged but at low pH, the imidazolyl group is charged. If two imidazolyl groups are at close spatial proximity within a peptide at acid pH, they will repel each other and destabilize the conformation of the peptide at a pH where both groups are charged. If such groups are at close spatial proximity within the peptide network, peptides within the peptide network will repel one another and destabilize the peptide network at a pH where both groups are charged. Such destabilization may weaken the interaction of peptides in a peptide network formed at a pH where no charge repulsion occurs or may be significant enough to abolish all interactions resulting in dissipation of the peptide network and formation of a peptide ensemble that does not transmit force. Similar charge repulsions can be introduced by peptides with substituents that have charge repulsions at a suitably basic pH.

In addition, the ionization constant of an acidic or basic group may be altered as a result of adsorption at an oil-water or air-water interface. (Ariga et al. 2005 and references therein). The ionization constant of an acidic or basic group at an oil-water or air-water interface may also be affected by the ionic strength of the aqueous solution. In general, ionization constants of acidic or basic groups at an oil-water or air-water interface change in a direction that favours electrical neutrality at the interface. For example, in the presence of a spatially adjacent positive charge, an acidic group is likely to dissociate, that is, to lose a $H^+$ ion, at a lower pH at an oil-water or air-water interface than in bulk solution. Similarly, in the presence of a spatially adjacent negative charge, an acidic group is likely to dissociate, that is, to lose a $H^+$ion, at a higher pH at an oil-water or air-water interface than in bulk solution. As the dielectric constant of air is lower than that of oils, larger changes may be expected at the air-water interface than at oil-water interfaces. As a general principle, it is expected that pH effects on the rate of network formation at an interface will reflect acid ionization constants existing in bulk solution, while pH effects on the final strength of networks at an interface will reflect acid ionization constants existing at the interface.

In the context of stabilization of a foam or an emulsion, it may be favourable for the interfacial peptide network to bear a charge sufficient to promote electrostatic repulsion between individual gas bubbles or oil droplets, thus assisting in inhibiting coalescence of the phases. At the same time, it is understood that the net average charge per peptide molecule should not be sufficient to cause dissipation of the peptide network by repulsion between peptide molecules.

For switching of a charged peptide network at a fluid-fluid interface, it may be desirable to employ a stimulus having a charge opposite to that of the interface, in order to facilitate switching of the peptide network in a desired time frame. For example, it was found that acid-induced coalescence of an oil-in-water emulsion stabilized by peptide having SEQ ID NO:2 and Zn(II) ions did not proceed measurably on addition of HCl, but proceeded within seconds on addition of $H_2SO_4$. Without wishing to be bound by theory, it is proposed that this difference results from the difference in the charge on the species donating $H^+$ in each case, in interaction with the charge on the interface. Specifically, it is proposed that on $H_2SO_4$ addition, donation of $H^+$ to the interfacial network, leading to network dissipation, occurs primarily via the $HSO_4^-$ ion. This negatively charged species would not experience electrostatic repulsion on approaching a positively charged interface, such as may be expected to exist for a network containing peptide having SEQ ID NO:2 and Zn(II) ions. In contrast, in the case of HCl, donation of $H^+$ is expected to occur via the $H_3O^+$ ion. This positively charged species should experience an electrostatic barrier to reaction with a positively charged interfacial peptide network. In this case, use of a polyprotic acid for acid switching permits donation of $H^+$ to the peptide network by a negatively charged species, thus overcoming the effects of electrostatic repulsion at the interface. The choice of a suitable polyprotic acid will be determined by the acid dissociation constants of the polyprotic acid and the desired pH of the experiment. Similarly, in cases where it is desirable to switch a peptide network at a negatively charged fluid-fluid interface by removal of $H^+$, it may be desirable to use a polybasic species, such as spermine or polyethyleneimine, to allow removal of $H^+$ from the peptide network by a positively charged species, thus overcoming the effects of electrostatic repulsion at the interface. Similarly, in the context of switching of a peptide network by addition of a chelating agent, it may be necessary to choose a chelating agent having a charge opposite to that of the interface. For example, use of the negatively charged chelating agent EDTA was effective in switching an emulsion containing peptide having SEQ ID NO:2 and Zn(II) ions, in which the interface is expected to carry a positive charge. However, EDTA did not switch an emulsion containing peptide having SEQ ID NO:4 and La(III) ions, in which the interface may bear a negative charge. In addition, the charge on an interface containing a peptide network may differ between air-water and oil-water interfaces in contact with bulk aqueous solutions of similar composition. For example, a foam containing peptide having SEQ ID NO:2 and Zn(II) ions can be switched using HCl, whereas an emulsion containing peptide having SEQ ID NO:2 and Zn(II) ions at a similar concentration cannot be switched using HCl, but requires use of a polyprotic acid such as $H_2SO_4$, citric acid, or $H_3PO_4$. The observed difference between foams and emulsions is consistent with a greater tendency to electrical neutrality at air-water interfaces as compared with oil-water interfaces. In addition, the tendency of particular ions, including $HO^-$ and/or $H_3O^+$ ions, to adsorb at air-water and oil-water interfaces (Mucha et al., 2005 and references therein), may contribute to the total charge present at the interface, in addition to the contribution to interfacial charge from peptide molecules adsorbed at the interface.

The ionization constant of an acidic or basic group may also be altered as a result of binding of a metal ion.

Suitable acids and bases are those which are soluble in and alter the pH of the peptide solution from which the peptide network is formed. The acids and bases may be inorganic or organic. Illustrative examples of suitable inorganic acids include, but are not limited to, hydrochloric acid, hydrofluoric acid, hydrobromic acid, hydroiodic acid, nitric acid, sulfuric acid and phosphoric acid. Illustrative examples of suitable organic acids include, but are not limited to, acetic acid, formic acid, propionic acid, butyric acid, benzoic acid, citric acid, tartaric acid, malic acid, maleic acid, hydroxymaleic acid, fumaric acid, lactic acid, mucic acid, gluconic acid, oxalic acid, phenylacetic acid, methanesulphonic acid, toluenesulphonic acid, benzenesulphonic acid, salicylic acid, sulphanilic acid, ascorbic acid and valeric acid, succinic acid, glutaric acid and adipic acid. Illustrative examples of suitable bases include but are not limited to ammonia, organic amines, sodium hydroxide, potassium hydroxide, calcium hydroxide, magnesium hydroxide, sodium carbonate, potassium carbonate, magnesium carbonate, calcium carbonate, sodium bicarbonate, potassium bicarbonate, magnesium bicarbonate and calcium bicarbonate.

The stimulus may be a chaotropic agent, such as guanidinium chloride or urea or may be high temperature. Chaotropic agents or high temperature may be used to disrupt secondary structure of peptides. Disruption of secondary structure of peptides results in loss of ordered structure, such as $\alpha$-helical or $\beta$-sheet structure, and may reduce the ability of the peptides to form interactions with other peptides or may reduce the affinity of the peptides for the fluid-fluid interface, as a result of loss of ordered secondary structure. Suitable temperatures for disrupting peptide secondary structure include temperatures above 40° C., for example temperatures between 40° C. and 100° C., 40° C. and 80° C., 40° C. and 60° C. or 40° C. and 50° C. In addition, the presence of a chaotropic agent may weaken intermolecular interactions between peptide molecules adsorbed at the fluid-fluid interface by providing alternate interaction partners for the bonding interactions of peptides, such as hydrogen bonding interactions or charge-charge interactions. In addition, the presence of a chaotropic agent may reduce the affinity of the peptides for the fluid-fluid interface by altering the structuring of water in the bulk phase, thus diminishing the hydrophobic driving force for peptide adsorption at the fluid-fluid interface.

The stimulus that alters the chemical and/or physical properties of the peptide may also be a salt. The addition of a salt to a solution will change the ionic strength of the solution and thereby alter or disrupt ionic interactions such as ion pair interactions or dipole-dipole interactions within a peptide or between peptides. The anion of an added salt may also serve as a ligand to metal ions present in solution, which may serve to stabilize metal ion complexes with peptides by altering the non-peptide elements in the coordination sphere of the metal ion. Alternately, the addition of a salt may cause the anion of the salt to displace peptide from the metal coordination sphere. Suitable salts that may be used are any salts soluble in the bulk peptide solution from which the peptide network is formed. For example suitable salts include, but are not limited to, sodium chloride, potassium chloride, calcium chloride, magnesium chloride, sodium nitrate, potassium nitrate, sodium bromide, potassium bromide, sodium iodide, potassium iodide, sodium sulfate and potassium sulfate.

The stimulus that alters the chemical and/or physical properties of the peptide may also be a molecule, other than a chelating agent, that binds to added metal ions. The addition of a non-chelating metal ligand may serve to stabilize metal ion complexes with peptides by altering the non-peptide elements in the coordination sphere of the metal ion. Alternately, under different conditions, the addition of a non-chelating metal ligand may cause the non-chelating metal ligand to displace peptide from the metal coordination sphere. Suitable molecules are any molecules capable of being monodentate ligands and that are soluble in the bulk peptide solution from which the peptide is formed. For example, suitable ligands include, but are not limited to, imidazole and substituted imidazoles, thiols and thiolate anions, thioethers, thiazole and substituted thiazoles, ammonia and organic amines, phenol and substituted phenols, pyrrole and substituted pyrroles, pyridine and substituted pyridines, carboxylic acids, triphenylphosphine, cyanide, cyanate, and thiocyanate. Suitable substituents include those that have no metal ion binding capacity. For example, suitable substituents include alkyl groups, alkenyl groups, alkynyl groups, cycloalkyl groups and aryl groups, particularly $C_{1-6}$alkyl groups, $C_{2-6}$alkenyl groups, $C_{2-6}$alkynyl groups, $C_{3-6}$cycloalkyl groups and $C_{6-10}$aryl groups.

The stimulus that alters the chemical and/or physical properties of the peptide may be an organic or inorganic counterion that can interact with charged residues in the peptide and therefore alter metal ion bridging, ionic attractive interactions or ionic repulsive interactions. Suitable counterions include, but are not limited to, spermine, citrate, malate, oxaloacetate, polyethyleneimine, phosphate and borate. Suitable counterions may also include charged amphipathic species that bind at the interface, such as detergents. One example is the negatively charged detergent, sodium dodecyl sulfate (Example 57). Other positively or negatively charged detergents may also be suitable counterions.

The stimulus that alters the chemical and/or physical properties of the peptide may be an oxidizing or reducing agent. Addition of an oxidizing agent will result in oxidation of the sides chains of amino acid residues that are susceptible to oxidation. For example, the hydroxy groups of serine residues may be oxidized to aldehydes or carboxylic acid groups and the hydroxy group of threonine residues may be oxidized to a carbonyl group. Such oxidations will alter the interactions that may occur within a peptide, for example by breaking hydrogen bonds that the hydroxy group was participating in, allowing new hydrogen bonds to form with a carbonyl group or providing carboxyl group which could be ionized to form a charged residue. The addition of an oxidizing group may also result in the formation of disulfide bonds between two spatially adjacent cysteine residues within a peptide or within the peptide network. Similarly the addition of a reducing agent will result in reduction of the side chains of amino acid residues that are susceptible to reduction. For example, the carboxylic acids present on aspartic acid or glutamic acid side chains may be reduced to aldehydes or primary alcohols. Carboxylic acids, aldehydes or carbonyl groups present on amino acid residues that had been previously oxidized, may also be reduced to primary or secondary alcohols in the presence of a reducing agent. Furthermore, disulfide bonds between cysteine residues, either within a peptide or between peptides, may be reduced to free thiol groups in the presence of a reducing agent. Illustrative examples of suitable oxidizing agents include, but are not limited to, hydroxyethyldisulfide, oxygen, alkaline potassium permanganate, osmium tetroxide, peroxybenzoic acid, sodium meta-periodate and Dess Martin Reagent. Illustrative examples of reducing agents include, but are not limited to, $H_2$, dithiothreitol and β-mercaptoethanol.

In one aspect of the invention there is provided a method of modulating interfacial characteristics, such as force transmission, in a self-assembled, force-transmitting peptide network at a fluid-fluid interface comprising the steps of:
  i) at a first time, exposing a peptide capable of participating in a self-assembled, force-transmitting peptide network, either before or after it interacts with other peptides to form the peptide network, to a first stimulus which alters the chemical and/or physical properties of the peptide; and
  ii) at a second time, exposing the peptide to a second stimulus which alters the chemical and/or physical properties of the peptide adopted upon exposure to the first stimulus.

This aspect of the invention allows the formation of the peptide network under a first set of conditions at a first time and the weakening or disruption of the peptide network under a second set of conditions at a second time. Alternatively, the formation of a peptide network may be delayed by preventing its formation at a first time by a first set of conditions then allowing the peptide network to form at a second time under a second set of conditions. In some embodiments, this method is used in the formation and dissipation of an emulsion or foam in a predictable manner or the delay of the formation of a foam or emulsion until a desired time.

The force transmission of a self-assembled peptide network may be determined using an interfacial tensiometer such as the Cambridge Interfacial Tensiometer (CIT), (Jones and Middelberg, 2002a, Jones and Middelberg, 2002c). The CIT may also be used to determine whether a particular peptide is capable of forming a peptide network which transmits force such that it has an elastic or storage modulus significantly greater than zero.

Determination of the properties of the interfacial peptide network may also employ methods of interfacial rheology, such as shear rheology. In addition, the elastic or viscous properties of the interfacial peptide network may be studied by means of interfacial dilational rheology.

In one example of determining force transmission, an aliquot of peptide is dissolved in buffer to provide the desired final concentration, typically 1.0-10 μM, in a desired volume, typically 8.2-9.0 mL. A fixed volume of the peptide solution is transferred into the CIT bath at time=0 to give a meniscus approximately 1-2 mm above the CIT bath edge and level with pre-aligned T-pieces at an initial separation of 1000 μm. The interface is then allowed to age for 60 minutes allowing the peptide to migrate to the interface at a sufficient concentration to form a peptide ensemble or in some cases allow interaction to occur between peptide molecules, thereby forming the peptide network. After aging of the interface, the T-pieces are separated to subject the interface to a 5% strain repeatedly and the force measured each time to provide an interfacial stress versus strain curve. The slope of the curve to 1% strain is then used to determine the interfacial elasticity modulus. Maximum interfacial stress that may be applied to a peptide ensemble or peptide network may be determined directly from an interfacial stress versus strain curve where 0% to 300% interfacial stress is applied.

In some embodiments, the peptide network has an interfacial elasticity modulus greater than or equal to 30 mN/m, especially greater than or equal to 50 mN/m, even more especially greater than or equal to 100 mN/m. In some embodiments, the peptide network has a peak or maximum interfacial stress of greater than 0.5 mN/m, especially greater than 1.5 mN/m and more especially greater than or equal to 5 mN/m.

It is possible to design peptides for use in the methods of the invention that are capable of forming a self-assembled, force-transmitting peptide network under a first set of conditions and which do not form a peptide network or form a much weaker peptide network under a second set of conditions. It is also possible to design peptides for use in the invention that form a force-transmitting network under a first set of conditions which can be entirely dissipated to form a non-force transmitting peptide ensemble under a second set of conditions.

For example, it is possible to design a peptide which at a suitably neutral or basic pH is uncharged but at a suitably acidic pH is protonated. In such a case, incorporating two amino acids into the peptide which are spatially adjacent in the peptide and which may both be protonated and therefore charged at acidic pH is one means of designing a peptide such that under a given set of conditions a peptide network will not form or will be disrupted.

In another example, it is possible to design a peptide to include polar or charged residues in spatial proximity which may be able to bind to a metal ion thereby stabilizing a peptide conformation which favours peptide network formation. Alternatively, the polar or charged residues may be on different peptides and binding of metal ions results in an interaction between the different peptides which strengthens the peptide network.

An example of a peptide designed to display both pH dependent destabilization of a peptide network and metal ion stabilization of helical peptide conformation is a peptide having SEQ ID NO:2.

SEQ ID NO: 2: Ac-MKQLADS LHQLARQ VSRLEHA-CONH$_2$

Peptide SEQ ID NO:2 is derived from peptide SEQ ID NO:1 which has previously been shown not to transmit force (Middelberg et. al., 2000).

SEQ ID NO: 1: Ac-MKQLADS LMQLARQ VSRLESA-CONH$_2$

Under some conditions, peptides having SEQ ID NO:1 form a coiled-coil tetrameric structure as shown in FIG. 1, A in bulk solution. In SEQ ID NO:2, the Met-9 and Ser-20 residues of SEQ ID NO:1 have been replaced by histidine. This substitution introduces a charge repulsion between ionized His-9 and His-20 and their adjacent cationic residues in the helical peptide structure, Arg-13 and Arg-16, at acidic pH. Therefore this peptide was expected to form a network at neutral or basic pH but have a substantially weakened network or no network at acid pH. Furthermore, the spatial proximity of His-9 to other polar residues, Lys-2 and Asp-6, offers the possibility of transition metal ion binding to provide stabilization of the coiled-coil structure (FIG. 1, B). Alternately, either His-9 or His-20 may participate in metal ion bridging interactions whereby a metal ion bound to either His-9 or His-20 also binds to a metal-binding group of a spatially adjacent peptide at an interface.

Initial experiments with peptide networks formed from peptides having SEQ ID NO:2 showed the peptide network transmits force at the air-water interface at pH 8 (Example 1). The measured interfacial elasticity modulus was 81.4 mN/m and the maximum interfacial stress transmitted was 1.9 mN/m. However at pH 3 (Example 2), force transmission at the air-water interface was essentially abolished as the interfacial elasticity modulus was 19.7 mN/m and the maximum stress was 0.3 mN/m. The force transmission at pH 3 for peptide ensembles formed from peptides having SEQ ID NO:2, was very similar to the results shown for peptides having SEQ ID NO:1 (Example 3) which were known not to transmit significant force at the air-water interface (Jones and Middelberg, 2002b). Similar results were also obtained for Tween 80 (Example 4), a surface active agent which lacks the ability to form a significant interfacial network.

Peptides having SEQ ID NO:2 are capable of forming a self-assembled, force-transmitting peptide network at the air-water interface at pH 8.0 but form a peptide ensemble without network-forming capacity at the air-water interface at pH 3.0.

Furthermore, once formed, a self-assembled, force-transmitting peptide network formed from peptides having SEQ ID NO:2 can be disrupted or dissipated by altering the pH from neutral or basic to acidic pH. A self-assembled, force-transmitting peptide formed from peptides having SEQ ID NO:2 was formed at pH 8 (Example 5). The interfacial elasticity modulus at the air-water interface was determined to be 67.0 mN/m and the maximum interfacial stress 1.2 mN/m. The pH of the bulk peptide solution was then acidified to pH 3 without disturbing the interface where measurements were being recorded and the interface allowed to age at the new pH before further measurement. After aging, the interfacial elasticity modulus at the air-water interface was reduced to 4 mN/m and the maximum strain reduced to 0.2 mN/m. These results show that a force-transmitting peptide network formed at one pH can be switched to a non-force transmitting peptide ensemble upon acidification.

A possible effect of peptide conformational stability in the ability of a peptide to form a self-assembled, force-transmitting peptide network is shown by the contrast in force transmission between peptides having SEQ ID NO:1 and SEQ ID NO:3.

SEQ ID NO: 3:
Ac-LMQLARQ MKQLADS LMQLARQ VSRLESA-CONH$_2$

Peptides having SEQ ID NO:3 form significantly more stable helical coiled-coils in bulk solution than peptides having SEQ ID NO:1 (Fairman et al., 1995). This is due to the increased length of peptides having SEQ ID NO:3 and an increased strength of intermolecular hydrophobic interactions in the coiled-coil tetramer formed by peptides having SEQ ID NO:3. Both peptides having SEQ ID NO:1 and SEQ ID NO:3 are capable of forming coiled-coil tetramers at a sufficiently high concentration in bulk solution (FIG. 1, A and C), however, under the conditions of force transmission used, peptides having SEQ ID NO:3 self-assemble in bulk solution into coiled-coil tetramers whereas peptides having SEQ ID NO:1 are largely monomeric and assume a random coil structure. Without wishing to be bound by theory, it is postulated that this increased inter-peptide interaction in bulk solution translates to an increased inter-peptide interaction at the fluid-fluid interface.

At pH 8.0, a peptide network formed from peptides having SEQ ID NO:3 displays an average interfacial elasticity modulus at the air-water interface of 266.8 mN/m and average maximum interfacial stress of 20.5 mN/m (Example 14), significantly higher than for peptide ensembles formed from peptides having SEQ ID NO:2 and higher than values for the industrially important protein β-lactoglobulin (interfacial elasticity modulus at the air-water interface 150 mN/m and maximum interfacial stress at the air-water interface 14 mN/m at 0.1 mg/mL for β-lactoglobulin in phosphate-buffered saline).

At pH 6.0 and 11.0, force transmission by peptide networks formed at the air-water interface from peptides having SEQ ID NO:3 is equivalent within experimental error to that measured at pH 8.0. However, at pH 3.0 the values of the interfacial elasticity modulus and maximum interfacial stress at the air-water interface fall by a factor of two. This does not appear to be due to a change in peptide conformation, as bulk peptide structure is unchanged under these conditions, with a $\theta_{222}/\theta_{208}$ ratio close to 1.0, obtained by circular dichroism spectroscopy (FIG. 4, upper graph) consistent with a coiled coil structure. Without wishing to be bound by any one theory, while the values of interfacial elasticity modulus and maximum strength at pH 3.0 remain high by comparison to peptide networks formed by peptides having SEQ ID NO:2, it appears an increased positive charge on peptides having SEQ ID NO:3 at lower pH weakens either the affinity of peptides having SEQ ID NO:3 for the hydrophobic air-water interface (leading to lower interfacial coverage and weaker network formation) or the strengths of interactions between peptides having SEQ ID NO:3 in the interface.

Without wishing to be bound by theory, the possible importance of helical structure to force transmission by peptide networks formed from peptides having SEQ ID NO:3 is shown by the effect of adding a chaotropic agent at a high enough concentration to abolish secondary structure. Force transmission is abolished by inclusion of 6 M urea in the buffer (Example 15). Interestingly, force transmission is not abolished, but merely reduced, for the protein β-lactoglobulin under the same conditions, suggesting that the longer protein sequence may participate in enough weak interactions even in the presence of 6 M urea as to maintain force transmission in the absence of significant secondary structure. This is most likely through an "entanglement" mechanism where the protein sequences are physically entangled with one another. Alternately, abolition of force transmission by peptides having SEQ ID NO:3 in the presence of a chaotropic agent may be a result of a loss of peptide secondary structure at the interface, leading to a weakening of peptide-peptide interactions, or may be a result of the replacement of peptide-peptide interactions at the interface, such as hydrogen bonding interactions, by peptide-chaotrope interactions. Finally, the presence of a high concentration of chaotrope may result in desorption of peptide from the interface, as a result of a loss of peptide secondary structure at the interface, or as a result of a reduced hydrophobic driving force for peptide adsorption at the interface due to alteration in bulk water structure, or both.

A possible effect of stabilization of the helical conformation can also be demonstrated by the presence of metal ions. Added transition metal ions might be expected to stabilize the helical structure of peptides having SEQ ID NO:2 by forming a stabilizing interaction between the amino acid residues at the surface of the helix. Alternatively, metal ions may cross-link different peptide molecules at the interface, leading to an increase in network strength via a different mechanism. Example 6 shows the effect of initially present Ni(II) or metal chelating agent EDTA on force transmission by peptides having SEQ ID NO:2. The presence of 1 mM divalent nickel increases force transmission substantially above the level seen for peptides having SEQ ID NO:2 alone, with an interfacial elasticity modulus of 105.3 mN/m and a maximum interfacial stress of 6.1 mN/m at the air-water interface. In the presence of 5 mM EDTA which scavenges or removes any adventitious metal ions bound to the peptide, the interfacial elasticity modulus is reduced to 32.6 mN/m, and the maximum interfacial stress falls to 0.5 mN/m. Comparison of these values with those obtained for peptide networks formed from peptides having SEQ ID NO:2 alone (interfacial elasticity modulus 65.8 mN/m, maximum interfacial stress 1.6 mN/m at the air-water interface in the same buffer system suggest that peptides having SEQ ID NO:2 bind adventitious metal ions under normal handling conditions, and that this contributes to a higher level of force transmission relative to peptides having SEQ ID NO:1.

To test whether enhancement of force transmission by peptide networks formed from peptides having SEQ ID NO:2 with added nickel was reversible, a peptide network was prepared at the air-water interface in the presence of 1 mM Ni(II), and force transmission was verified, before addition of an amount of EDTA sufficient to give 5 mM bulk solution concentration, in such a way as to avoid mechanical disruption of the interface where measurements were being recorded. As with acidification of a network of peptides having SEQ ID NO:2, the addition of EDTA to a Ni(II)-SEQ ID NO:2 interface leads to significant reduction in force transmission, with reduction of the interfacial elasticity modulus from 103.4 to 49.0 mN/m and maximum interfacial stress from 5.9 to 1.0 mN/m (Example 7).

The results are consistent with the enhancement of stability of the amphipathic α-helix, allowing for the formation of a highly structured interface with ordered interaction capacity. Alternatively, the results are consistent with a model in which added metal ions serve to cross-link different peptide molecules at the interface. The removal of bound metal ion from the peptide by addition of a chelator leads to reduction in force transmission similar to that seen for addition of acid to peptide networks formed by peptides having SEQ ID NO:2.

Metal ions other than Ni(II) can also enhance force transmission by peptide networks formed from peptides having SEQ ID NO:2. When 100 μM Zn(II) was added to a network of peptide having SEQ ID NO:2 formed at the air-water interface initially in the absence of metal ions, the force transmission was significantly enhanced. Subsequent addition of 200 μM EDTA reduced force transmission to levels observed in the absence of added metal ions (Example 8).

Zinc-containing networks formed from peptides having SEQ ID NO:2 can be dissipated by the addition of acid. When a peptide network was formed at the air-water interface in the presence of 100 μM Zn(II) at an initial pH of 7.4, significant levels of force transmission were observed. Addition of sufficient HCl to reduce the solution pH to 3.8 completely abolished force transmission, while subsequent addition of sufficient NaOH to restore the solution pH to 7.4 restored force transmission (Example 9). Similar results were obtained when the acid used was $H_2SO_4$ in a sufficient amount to reduce the solution pH to 3.6 (Example 17).

Similarly, when 100 μM Cu(II) was added to a network of peptide having SEQ ID NO:2 formed at the air-water interface initially in the absence of metal ions, the force transmission was significantly enhanced. Subsequent addition of 200 μM EDTA reduced force transmission to levels observed in the absence of added metal ions (Example 10).

Cu(II)-containing networks formed from peptides having SEQ ID NO:2 can be dissipated by the addition of acid. When a peptide network was formed at the air-water interface in the presence of 100 μM Cu(II) at an initial pH of 7.4, significant levels of force transmission were observed. Addition of sufficient HCl to reduce the solution pH to 3.8 completely abolished force transmission, while subsequent addition of sufficient NaOH to restore the solution pH to 7.4 restored force transmission (Example 11).

Addition of metal ions or EDTA to a bulk solution containing peptides having SEQ ID NO:2 can be shown to alter the kinetics of entry of the peptide into the air-water interface (Example 12). The final interfacial tension is only slightly different between solutions of peptide having SEQ ID NO:2 in the presence of 100 µM EDTA, 100 µM Zn(II), 100 µM Ni(II) or 100 µM Cu(II), indicating that the interface is populated by peptide in each case. However, the rate of reduction in interfacial tension is different. Reduction in interfacial tension is most rapid in the presence of 100 µM EDTA, suggesting that the peptide is relatively unstructured under these conditions and does not experience steric barriers to entry to the interface. In the presence of 100 µM Cu(II), peptide entry into the interface, as determined by the changes in interfacial tension, is slower and biphasic, suggesting that the peptide has undergone an increase in structuring in the presence of the added metal ion. Similar results have been observed with peptides having SEQ ID NO:3 (Middelberg et al., 2000), which are known to be highly structured in solution (Fairman et al., 1995). In the presence of 100 µM Zn(II) or Ni(II), peptide adsorption at the interface is slower, but no biphasic kinetics are observed, suggesting that the mode of peptide structuring in solution may be different with Zn(II) compared to that with Cu(II).

Bubble tensiometry also showed that peptides having SEQ ID NO:2 adsorbed at the air-water interface to a similar extent at neutral pH in the presence or absence of Zn(II) ions, or following acidification to pH 3.6 (Example 18). In the presence of EDTA, added to scavenge adventitious metal ions, peptides having SEQ ID NO:2 rapidly lowered the interfacial tension at the air-water interface, achieving a value of 52.9 mN/m after 1000 s. When 100 µM Zn(II) was present, the interfacial tension at 1000 s was 52.1 mN/m, while inclusion of $H_2SO_4$ to a pH of 3.6 gave a slightly higher interfacial tension of 54.6 mN/m. Formation of force transmitting rather than non-force transmitting states was therefore not accompanied by large changes in peptide concentrations at the interface.

To test whether network formation by an interfacially active peptide increases the emulsifying activity of the peptide, a test emulsion was prepared using peptides having SEQ ID NO:2 in the presence of either 70 µM Cu(II) or 100 µM EDTA (Example 16). The initial peptide concentration in the aqueous solution was 156 µg mL$^{-1}$ in 25 mM MOPS, 100 mM NaCl, pH 6.2. Silicone oil was added to a volume fraction of 10% and the mixture was stirred at maximum speed in a rotor-stator homogenizer. Using standard methods, the emulsifying activity index (EAI) of the peptide was determined to be 118 m$^2$ g$^{-1}$ in the presence of added Cu(II) and 99 m$^2$ g$^{-1}$ in the presence of added EDTA, showing that peptide network formation enhances emulsification. This occurs even though final interfacial tension does not appear to be significantly different between solutions of peptides having SEQ ID NO:2 containing added EDTA, and solutions of peptides having SEQ ID NO:2 containing added Cu(II). It is likely that under the conditions of the experiment, in particular the pH, the low concentration of EDTA used was not fully effective in sequestering adventitious metal ions which may bind to peptide having SEQ ID NO:2, and that the true EAI of metal-free peptide having SEQ ID NO:2 is lower. By way of comparison, peptide having SEQ ID NO:1 showed an EAI of only 36 m$^2$ g$^{-1}$ under similar conditions. Further, when an emulsion was prepared containing peptide having SEQ ID NO:2 in the presence of 100 µM Cu(II), subsequent addition of 1 mM EDTA led to rapid coalescence of the emulsion and separation of the phases.

To further test the effects of the stimuli-responsive interfacial peptide film on emulsion stability, a toluene-in-water emulsion was prepared in the presence of micromolar concentrations of peptides having SEQ ID NO:2 and Zn(II) in 25 mM HEPES, pH 7.4 (Example 19). Under these conditions peptides having SEQ ID NO:2 were an effective emulsifying agent, with a high emulsifying activity index (EAI) (Cameron et al., 1991) of 360 m$^2$ g$^{-1}$. The peptide-Zn(II) emulsion was stable to phase coalescence over 20 hours at room temperature. However, when an aliquot of $H_2SO_4$ was added to disrupt Zn(II)-peptide binding, the emulsion rapidly coalesced, with gross phase separation occurring in a matter of seconds and clean recovery of both phases possible within 10 min. Similarly, when excess EDTA was added, the peptide-Zn(II) emulsion rapidly coalesced. It appears that under non-network conditions, the peptide is not effective at stabilizing oil-in-water emulsions based on lowering of interfacial tension alone. Support for this interpretation is provided by the observation that an peptide having SEQ ID NO:2-containing toluene-in-water emulsion prepared in the presence of 100 µM EDTA coalesced within seconds after mixing. Similarly, when a peptide having SEQ ID NO:2-Zn(II) solution was acidified before homogenization with toluene, the dispersion coalesced in seconds after the end of mixing. Strongly emulsion-stabilizing properties thus appear to correlate with the interfacial network state of peptides having SEQ ID NO:2, not the non-force transmitting state.

To demonstrate the effects of pH-dependent changes in charge on force transmission at the interface using a mixed or heterogeneous peptide network, peptides having SEQ ID NO:9 and peptides having SEQ ID NO:10 were employed (Example 23). At pH 7.0, the two peptides are expected to bear opposite charges, with peptide having SEQ ID NO:9 bearing a net negative charge and peptide having SEQ ID NO:10 bearing a net positive charge. An interfacial network assembled from a bulk solution containing peptide having SEQ ID NO:9 and peptide having SEQ ID NO:10 at pH 7.0 gave an interfacial elasticity modulus of 53 mN/m and a maximum interfacial stress of 2.0 mN/m. On addition of an aliquot of HCl solution, sufficient to reduce the bulk solution pH to 3.0, followed by re-equilibration of the interface, force transmission was found to be significantly increased, giving an interfacial elasticity modulus of 146 mN/m and a maximum interfacial stress of 9.1 mN/m. On addition of an aliquot of NaOH solution, sufficient to restore the bulk solution pH to 7.0, followed by reequilibration of the interface, force transmission was found to be reduced to levels close to the original level, with an interfacial elasticity modulus of 60 mN/m and a maximum interfacial stress of 2.6 mN/m. Without wishing to be bound by theory, it is proposed that the level of force transmission at pH 7.0 in a heterogenous network formed from peptides having SEQ ID NO:9 and peptides having SEQ ID NO:10 reflects interaction between peptide molecules having opposite charges in the interface.

The interaction is probably based partly on intermolecular salt bridges between the side chain amino groups of charged glutamate residues in the b and c positions of the heptad of peptides having SEQ ID NO:9, and side chain amino groups of charged lysine residues in the b and c positions of the heptad of peptides having SEQ ID NO:10. The interaction is probably also based partly on hydrophobic interactions between, among others, methylene groups of charged glutamate residues in the b and c positions of the heptad of peptide having SEQ ID NO:9, and methylene groups of charged lysine residues in the b and c positions of the heptad of peptides having SEQ ID NO:10. Without wishing to be bound by theory, it is proposed that the increase in force transmission at pH 3.0 by a heterogeneous network formed from peptides having SEQ ID NO:9 and peptides having SEQ ID NO:10 reflects preferential population of the interface by peptides having SEQ ID NO:9 at pH 3.0, resulting in a stronger network with a relatively higher content of SEQ ID NO:9 at pH 3.0. The restoration of force transmission on return to a bulk solution pH of 7.0 indicates that the changes in the interfacial ensemble are reversible.

To demonstrate the effects of an added organic counterion on force transmission at the interface, a peptide having SEQ ID NO:9 was employed (Example 26). At pH 8.0, the peptide is expected to bear a significant negative charge. An interfacial ensemble assembled from a bulk solution containing peptide having SEQ ID NO:9 at pH 8.0 in the absence of added organic counterions gave an interfacial elasticity modulus of 3 mN/m and a maximum interfacial stress of 0.3 mN/m. On addition of an aliquot of polyethyleneimine (PEI) solution, sufficient to give a bulk solution of 0.2% (w/v), followed by re-equilibration of the interface, force transmission was found to be increased, with an interfacial elasticity modulus of 18 mN/m and a maximum interfacial stress of 0.9 mN/m. Without wishing to be bound by theory, it is proposed that the increased level of force transmission at pH 8.0 in the presence of 0.2% (w/v) PEI, by peptides having SEQ ID NO:9 reflects binding of the positively charged PET by negatively charged peptides having SEQ ID NO:9. While not wishing to be bound by theory, the interaction may be based in part on neutralization of the negative charge on the peptide by binding of PEI, and may also involve stabilization of an ordered structure of the peptide by binding of PEI and may also involve bridging of PEI between spatially adjacent peptide molecules within the network.

To further demonstrate the effects of added multivalent counterions on force transmission at the interface, a peptide having SEQ ID NO:10 was employed (Example 28). At pH 7.3, the peptide is expected to bear a significant positive charge. An interfacial ensemble assembled from a bulk solution containing peptide having SEQ ID NO:10 at pH 7.3 in the absence of added multivalent counterions gave an interfacial elasticity modulus of 29 mN/m and a maximum interfacial stress of 0.5 mN/m. On addition of an aliquot of a mixed solution of sodium phosphate, sodium citrate and sodium borate, sufficient to give bulk solution concentrations of 1 mM sodium phosphate, 1 mM sodium citrate and 1 mM sodium borate, followed by re-equilibration of the interface, force transmission was found to be increased, with an interfacial elasticity modulus of 51 mN/m and a maximum interfacial stress of 1.4 mN/m. Without wishing to be bound by theory, it is proposed that the increased level of force transmission at pH 7.0 in the presence of 1 mM sodium phosphate, 1 mM sodium citrate and 1 mM sodium borate, by peptides having SEQ ID NO:10 reflects binding of the negatively charged phosphate, citrate and/or borate ions by positively charged peptides having SEQ ID NO:10. The interaction is probably based in part on neutralization of the positive charge on the peptide by binding of phosphate, citrate and/or borate ions, and may also involve stabilization of an ordered structure of the peptide by binding of phosphate, citrate and/or borate ions and may also involve bridging of phosphate, citrate and/or borate ions between spatially adjacent peptide molecules within the network.

In another embodiment, the self-assembled, force-transmitting peptide network is formed from a peptide having a β-sheet conformation. Preferred peptides having a β-sheet conformation have a hydrophobic face and a hydrophilic face, the hydrophobic face having an affinity for the fluid-fluid interface.

To further illustrate the effects of pH on force transmission at the interface where the network is formed with peptides having a β-sheet structure, a peptide having SEQ ID NO:6 was employed (Example 35). An interfacial network assembled from a bulk solution containing peptide having SEQ ID NO:6 at pH 6.0 gave an interfacial elasticity modulus of 355 mN/m and a maximum interfacial stress of 14.6 mN/m. On addition of an aliquot of HCl solution, sufficient to reduce the bulk solution pH to 3.0, followed by re-equilibration of the interface, force transmission was found to be reduced, with an interfacial elasticity modulus of 119 mN/m and a maximum interfacial stress of 6.1 mN/m. On addition of an aliquot of NaOH solution, sufficient to restore the bulk solution pH to 6.0, followed by re-equilibration of the interface, force transmission was restored to initial levels, with an interfacial elasticity modulus of 315 mN/m and a maximum interfacial stress of 14.3 mN/m. Without wishing to be bound by theory, it is proposed that the reduction in force transmission at acid pH results from protonation of some of the peptide histidine residues at the interface at pH 3, resulting in enhanced repulsion between peptide molecules at the interface bearing protonated arginine residues and protonated histidine residues. It is found that reduction of the bulk solution pH to approximately 2 results in complete dissipation of the peptide network (Example 49), consistent with an acidic species ionizing in this pH range at the interface. It is also proposed that this acidic species is the histidine residue of the peptide, the ionization constant of which has been altered in the context of the interface and adjacent species of like charge, particularly the arginine residue of the peptide. It is also proposed that dissipation of the network formed by a β-peptide of this length, which can interact with neighbouring peptide molecules at the interface by nine hydrogen bonds per peptide, requires the ionic repulsion generated by two like charges present per peptide molecule. Consistent with this theory, no force transmission is observed for peptide having SEQ ID NO:11 at a bulk solution pH of 2 (Example 53) or peptide having SEQ ID NO:12 at a bulk solution pH of 2 (Example 54), where each peptide is expected to bear a net charge close to +2 at the interface. Further consistent with this theory, force transmission is weaker but not abolished for peptide having SEQ ID NO:7 at a bulk solution pH of 2 (Example 56) or peptide having SEQ ID NO:8 at a bulk solution pH of 2 (Example 55), where each peptide is expected to bear a net charge close to +1 at the interface.

To illustrate the effects of metal ions on force transmission at the interface where the network is formed with peptides having a β-sheet structure, a peptide having SEQ ID NO:6 was employed (Example 50). A peptide network formed in the presence of 200 μM Ni(II) displayed an interfacial elasticity modulus of 516 mN/m and a maximum interfacial stress 15.4 mN/m. After addition of sufficient chelating agent to sequester the added metal ion, the interfacial elasticity modulus was reduced to 282 mN/m and the maximum interfacial stress to 11.1 mN/m. The result illustrates that force transmission by a β-sheet peptide network can be enhanced by the inclusion of metal ions, but force transmission is not abolished by the removal of metal ions. Without wishing to be bound by theory, it is proposed that metal ion-independent network strength is based on hydrogen bonds between peptides in the interfacial β-sheet, and additional network strength is derived from metal ion-dependent cross-linking between hydrophilic amino acid side chains, in this case histidine side chains, in contact with the aqueous phase.

To further test the effects of the stimuli-responsive interfacial peptide film on emulsion stability, a crude oil-in-water emulsion was prepared in the presence of micromolar concentrations of peptides having SEQ ID NO:2 and Zn(II) in 25 mM HEPES, pH 7.4 (Examples 46, 47). The oil used was a waxy crude oil which is solid at room temperature, and was warmed slightly to liquidefy the oil before emulsification. The peptide-Zn(II) crude oil emulsion was stable to coalescence over at least one hour at room temperature. When an aliquot of $H_2SO_4$ was added to disrupt Zn(II)-peptide binding, the emulsion coalesced within one minute. Similarly, when excess EDTA was added, the peptide-Zn(II) emulsion coalesced within one minute.

To demonstrate the utility of a peptide-stabilized emulsion in increasing the productivity of a biocatalytic reaction, a series of peptide-stabilized toluene-in-water emulsions containing peptide having SEQ ID NO:2 were prepared (Example 48). The toluene phase of the emulsion contained 1 M racemic methyl mandelate in each case to serve as the biocatalytic substrate. Oil volume fractions of 10% (v/v), 20% (v/v), 30% (v/v) and 50% (v/v) were employed, giving final methyl mandelate concentrations in the emulsion of 100 mM, 200 mM, 300 mM and 500 mM, respectively. The emulsions also contained a final concentration of 10 mM Tris.HCl, 40 mM NaCl, pH 8.0. For comparison, monophasic reaction media were prepared using a water-miscible solvent, acetonitrile, to increase the solubility of methyl mandelate. Volume fractions of 10% (v/v), 20% (v/v), 30% (v/v) and 50% (v/v) of a 1 M stock of methyl mandelate in acetonitrile were employed, giving final methyl mandelate concentrations in the acetonitrile medium of 100 mM, 200 mM, 300 mM and 500 mM, respectively. The acetonitrile media also contained a final concentration of 10 mM Tris.HCl, 40 mM NaCl, pH 8.0. Reactions in both peptide-stabilized emulsions and acetonitrile media were conducted in a volume of 1 mL over 3-5 h at 37° C. with 5 mg of a commercial immobilized enzyme (Lipolase lipase), and samples were taken at intervals to determine the level of biocatalytic conversion of methyl mandelate to mandelic acid. At each methyl mandelate concentration, biocatalytic productivity was higher in the peptide-stabilized emulsion than in the acetonitrile cosolvent system, with the difference being greater at higher substrate and solvent concentrations.

Accordingly, another aspect of the present invention provides a self-assembled, force-transmitting peptide network formed at a fluid-fluid interface wherein the peptide network comprises peptides that interact with one another and that have hydrophobic regions having an affinity for the fluid-fluid interface and wherein force transmission by the peptide network is manipulable by exposure to a stimulus which alters the chemical and physical properties of the peptide, with the proviso that the peptide network is not formed from SEQ ID NO:3.

Preferably the peptide network is formed from peptides which have amphipathic character and an ordered conformation such as a helical conformation, or a β-sheet conformation. Especially preferred conformations are α-helical conformations, or β-sheet conformations which have a hydrophobic face and a hydrophilic face.

Preferably the peptides of the invention may be designed to include amino acids which will contribute to interactions within a peptide and/or between peptides under a given set of conditions including but not limited to pH, temperature, ionic strength or the presence of metal ions or organic charge-bearing species but will not contribute to interactions under other conditions. Alternatively, peptides may be designed to include intramolecular or intermolecular interactions under a given set of conditions, e.g. pH, and which may have intramolecular or intermolecular repulsion under a second set of conditions. A person skilled in the art could manipulate a peptide sequence to include intramolecular or intermolecular attraction or repulsion by methods known in the art.

Examples of other peptides designed to have switchable properties suitable for use in the peptide networks of the invention are peptide sequences having SEQ ID NOs: 4 to 15.

```
SEQ ID NO: 4:    Ac-MKELADSLMQLARQVDRLESA-CONH2
SEQ ID NO: 5:    Ac-MKQLADSLHQLAHQVSHLEHA-CONH2
SEQ ID NO: 6:    Ac-PHFRFSFSP-CONH2
SEQ ID NO: 7:    Ac-PHFSFSFSP-CONH2
SEQ ID NO: 8:    Ac-PSFRFSFSP-CONH2
SEQ ID NO: 9:    Ac-MEELADSLEELARQVEELESA-CONH2
SEQ ID NO: 10:   Ac-MKKLADSLKKLARQVKKLESA-CONH2
SEQ ID NO: 11:   Ac-PHFHFSFSP-CONH2
SEQ ID NO: 12:   Ac-PFFSFHFSP-CONH2
SEQ ID NO: 13:   Ac-MKQLADSLHQLAHKVSHLEHA-CONH2
SEQ ID NO: 14:   Ac-EISALEKEISALEKEISALEK-CONH2
SEQ ID NO: 15:   Ac-KISALKEKISALKEKISALKE-CONH2
```

In one embodiment of the invention there is provided a peptide having SEQ ID NO:2.

In another embodiment of the invention there is provided a peptide having SEQ ID NO:4.

In another embodiment of the invention there is provided a peptide having SEQ ID NO:5.

In yet another embodiment of the invention there is provided a peptide having SEQ ID NO:6.

In a further embodiment of the invention there is provided a peptide having SEQ ID NO:7.

In yet a further embodiment of the invention there is provided a peptide having SEQ ID NO:8.

In another embodiment of the invention there is provided a peptide having SEQ ID NO:11.

In yet another embodiment of the invention there is provided a peptide having SEQ ID NO:12.

In yet another embodiment of the invention there is provided a peptide having SEQ ID NO:13.

The peptides of the invention may be prepared by known methods of the art such as solid phase synthesis or solution phase synthesis. Amino acids used in such methods may be commercially available or may be synthesised using methods known in the art, such as those provided in Jones, 1992. The peptides may also be prepared by recombinant peptide synthesis as known in the art.

Applications

The modulation of interfacial characteristics such as force transmission in self-assembled, force-transmitting peptide networks at fluid-fluid interfaces can be useful in applications such as emulsions, foams, coatings and drug delivery agents. For example, emulsion and/or foam stability and the control of coalescence of a dispersed gas or liquid phase in the foam or emulsion to allow a particular rate of coalescence or coalescence at a particular time is useful in foods, drinks, pharmaceuticals, cosmetics, inks and printing, paints and coatings, surfactants, waste water treatment, explosives, mineral recovery, bioremediation, corrosion inhibition, petrochemicals and oil recovery, medicine, dentistry, biocatalysis and biotechnology.

The invention may be useful in a plurality of applications in which it is desirable to transfer a desired material from an oil to a water phase, or from a water to an oil phase. The invention may further be useful in a plurality of applications in which it is desirable to transfer an undesired material, such as a waste product or contaminant, from an oil to a water phase, or from a water to an oil phase. In these cases, initial formation of a network allows stabilization of a large interfacial area in a finely dispersed oil-in-water or water-in-oil emulsion, enhancing the overall rate of transfer of a material from one liquid phase into another in which it is more soluble. Subsequent dissolution or weakening of the network allows breaking of the emulsion and coalescence of the liquid phases, followed by recovery of a desired material in a separated oil or water phase depending on solubility. Alternatively, subsequent dissolution or weakening of the network allows breaking of the emulsion and coalescence of the liquid phases, followed by removal of an undesired material, such as a waste product or contaminant, in a separated oil or water phase depending on solubility. For example, emulsion formation and breaking in this controlled manner may be useful in the extraction of valuable natural products from biological sources. In a further example, emulsion formation and breaking in this manner may be useful in the removal of toxic materials, such as organic pesticides, from waste water. In yet another example, emulsion formation and breaking in this manner, may be useful in the removal of corrosion-causing species from oil or more generally in enhanced oil recovery operations.

The invention may further be useful in a plurality of applications in which it is desirable to promote a process or reaction, which occurs exclusively or to an enhanced degree at the interface between a gas and a liquid or between a liquid and a second, immiscible liquid. For example, in applications where a catalyst present in a water phase acts on a reagent present in an oil phase, the catalysis occurring at the oil-water interface. Alternatively, in applications where a catalyst present in an oil phase acts on a reagent present in a water phase, the catalysis occurring at the oil-water interface. In these cases, initial formation of a network allows stabilization of a large interfacial area in a finely dispersed oil-in-water or water-in-oil emulsion, enhancing the rate of the desired process, such as catalytic transformation of a less desired material into a more desired material or of an undesired material, such as a waste product or contaminant, into a less undesired material, such as a breakdown product of a waste product or contaminant. This process may optionally be followed by transfer of the transformed material from one liquid phase into another, depending on solubility. Subsequent dissolution or weakening of the network allows breaking of the emulsion and coalescence of the liquid phases, followed by recovery of a more desired material in a separated oil or water phase depending on solubility. Alternatively, subsequent dissolution or weakening of the network allows breaking of the emulsion and coalescence of the liquid phases, followed by removal of a less undesired material, such as a breakdown product of a waste product or contaminant, in a separated oil or water phase depending on solubility.

The invention may further be useful in a variety of catalytic or biocatalytic applications in which a catalyst, for example an enzyme, present in the aqueous phase of an oil-in-water or water-in-oil emulsion, acts on a substrate which is sparingly soluble in water but is soluble or partly soluble in the oil phase of an oil-in-water or water-in-oil emulsion, or itself constitutes the oil phase of an oil-in-water or water-in-oil emulsion. The catalyst, for example an enzyme, may be dissolved in the aqueous phase or may be present in suspended form or adsorbed or otherwise bound, for example covalently bound, on a solid support, for example on a finely divided resin, beads or membrane, on solid fibres or within hollow fibres, or on the walls of a containing vessel. The enzyme may be present during initial emulsification, or may be contacted by a preformed emulsion, especially in the case of an oil-in-water emulsion in which water constitutes the continuous phase. The substrate in the aqueous phase is depleted by the action of the enzyme, and is replenished by diffusion of substrate in the oil phase into the aqueous phase. In these cases, initial formation of a network allows stabilization of a large interfacial area in a finely dispersed emulsion, enhancing the rate of replenishment of substrate in the aqueous phase and thus enhancing the rate of the reaction. This process may optionally be followed by transfer of the product of the catalytic reaction, for example an enzyme reaction, from the water to the oil phase, depending on solubility. Subsequent dissolution or weakening of the network allows breaking of the emulsion and coalescence of the liquid phases, followed by recovery of the product in the separated oil or water phase depending on solubility. The catalyst, for example an enzyme, may be recovered in soluble form in the aqueous phase, or if present in insoluble form or adsorbed or otherwise bound, for example covalently bound, on a solid support, for example on a finely divided resin, beads or membrane, on solid fibres or within hollow fibres, or on the walls of a containing vessel, may be separated from the emulsion either before or after breaking of the emulsion. This is exemplified in relation to the biotransformation of methyl mandelate to mandelic acid using a lipase enzyme.

The invention may further be useful in a plurality of applications in which it is desirable to employ a foam for the recovery or purification of a desired material by flotation. The invention may further be useful in a plurality of applications in which it is desirable to employ a foam for the removal of an undesired material, such as a waste material or contaminant, by flotation. In these cases, the use of a foam for flotation recovery or purification of a desired material may be followed by breaking of the foam for convenient further applications of the desired material. Alternatively, the use of a foam for flotation removal of an undesired material, such as a waste material or contaminant, may be followed by breaking of the foam for convenient further disposal of the undesired material.

The application may further be useful in controlling the contact of a first material contained in the oil phase of a first oil-in-water emulsion with a second material contained in the oil phase of a second oil-in-water emulsion. The two oil-in-water emulsions are prepared and then combined together under a first set of conditions where the network is stable and inhibits or prevents coalescence of the oil droplets, such that the first material and the second material are prevented from contacting each other. A second set of conditions is then applied under which weakening or dissolution of the peptide network occurs, with the result that oil droplet coalescence occurs and the first material and the second material are able to contact each other. One application of this would be in controlling a chemical reaction between a first material and a second material in an oil phase. For example, reaction between a first material and a second material might be desired only if a decrease in solution pH occurred, with the reaction acting as a indicator of pH change. Alternatively, reaction between a first material and a second material might be desired only in a specific biological context, defined by a particular temperature, pH, or metal ion concentration, for example in medical treatments. In another illustrative example, the application may be useful in controlling the contact of a first material contained in the water phase of a first water-in-oil emulsion with a second material contained in the water phase of a second water-in-oil emulsion. The two water-in-oil emulsions are prepared and then combined together under a first set of conditions where network formation occurs in the emulsion and inhibits or prevents coalescence of the water droplets, such that the first material and the second material are prevented from contacting each other. A second set of conditions is then applied under which weakening or dissolution of the peptide network occurs, with the result that water droplet coalescence occurs and the first material and the second material are able to contact each other. One application of this would be in controlling a chemical reaction between a first material and a second material in a water phase.

The invention may be useful in a plurality of applications where it is desirable that the properties of a foam or emulsion respond to contact with the human body, for example by responding to a change in temperature, pH, or the presence of metal ions or certain organic species. For example, it may be desirable to alter the stability of a food emulsion or foam on exposure to the pH and temperature characteristic of the human mouth, altering the flavour release properties, mouthfeel, viscosity or other properties of the emulsion or foam. Alternatively, it may be desirable to alter the stability of a dental emulsion or foam on exposure to the pH and temperature characteristic of the human mouth or the mouth of a particular non-human species, for example to transform a stable and less active stored form of a dental care product into a more active form. In other illustrative examples, it may be desirable to alter the stability of a pharmaceutical emulsion on exposure to the temperature and pH characteristic of the human stomach or other parts of the human intestinal tract, or the stomach or other parts of the intestinal tract of a particular non-human species. For example a stable and less active stored form of a pharmaceutical product may be transformed into a more active form. Alternatively, it may be desirable to alter the stability of a cosmetic emulsion or foam on exposure to the temperature and pH characteristic of human skin, for example to enhance the appearance of a cosmetic product. In another example, it may be desirable to alter the stability of a pharmaceutical emulsion or foam on exposure to the temperature and pH characteristic of human skin, for example to enhance skin permeation by a pharmaceutical product.

The invention may be useful in a plurality of applications where it is desirable to control the wetting or coating of a surface. In these cases a peptide-containing foam, emulsion, solution, or dispersion is provided which has particular properties of wetting or coating a surface under a first set of conditions, and distinct properties of wetting or coating a surface under a second set of conditions. This may be useful either in controlling the wetting of an entire surface, in the generation of desired patterns on a surface. Alternately, such controllable wetting may be useful in sensor applications, or in imaging.

The invention may also be useful in the oil industry for oil recovery or cleaning up oil spills. For example, stabilization of an emulsion formed from oil and water in an oil well can allow easy extraction of the emulsion from the well. After the emulsion has been recovered, de-emulsification may be stimulated by breaking up the peptide network, which stabilized the emulsion. The oil and water phases may then be separated. Alternatively, after an oil spill, an oil/water emulsion may be stabilized by a peptide network and recovered then at a desired time the peptide network may be weakened or dissipated allowing the phases of the emulsion to separate followed by recovery of the oil phase. This principle may be applied to waste water treatment in many industries where water is contaminated with an oil soluble contaminant. The oil soluble contaminant may be allowed to dissolve in an added oil phase during emulsion formation and stabilization. Then after adequate time for the contaminant to diffuse into the oil phase has elapsed, the emulsion could be broken by adding a stimulus that dissipates the network. After phase separation, uncontaminated waste water may be recovered.

The invention may also be useful in the oil industry for the transport of heavy oils. For example, emulsification of a heavy oil with a solution of peptide in water may generate an oil-in-water or water-in-oil emulsion which is easier to pump or transport by other means than the same heavy oil not so emulsified. After the emulsion has been transported to a desired location, de-emulsification may be stimulated by breaking up the peptide network, which stabilized the emulsion. The oil and water phases may then be separated.

The invention may also be useful in applications involving complex compositions, such as those present in cosmetics, pharmaceuticals and cleaning products, subject to the condition that the presence of a self-assembled, force-transmitting peptide network within the complex composition alters the properties of the composition. Other components which may be present in such complex compositions include, but are not limited to, detergents, salts, organic ions, and metal ions. In some cases, the other components present in a complex composition may enhance or diminish the strength of a force-transmitting peptide network self-assembled at a fluid-fluid interface. Examples of complex compositions in which the presence of a self-assembled, force-transmitting peptide network alters the properties of the composition, include crude oil-in-water emulsions in which surfactants are present in the crude oil (Examples 46, 47), and a foam containing peptide having SEQ ID NO:2 and the anionic detergent SDS (Examples 57, 66).

In a further aspect, there is provided a foam comprising a self-assembled, force-transmitting peptide network at a liquid-gas interface; said method comprising
  i) at a first time, exposing the liquid-gas interface to a first stimulus that alters the chemical and/or physical properties of a peptide in the peptide network; and
  ii) at a second time, exposing the liquid-gas interface to a second stimulus that alters the chemical and/or physical properties of the peptide in the peptide network adopted upon exposure to the first stimulus.

In some embodiments, the first stimulus causes formation of the self-assembled, force-transmitting peptide network, for example, by increasing the affinity of the peptide for the gas-liquid interface or altering the charge of the peptide side chains to remove repulsions or allow ionic interactions to occur. In some embodiments, the first stimulus causes an increase in the force transmission by the peptide network by, for example, increasing the number of interactions or the strength of interactions between peptides in the peptide network. In these embodiments, the second stimulus causes a reduction in the force transmission by the peptide network, for example, for reducing the number or strength of interactions between peptides, or causes abolition of force transmission by, for example, introducing repulsions between peptides within the network and/or by reducing the affinity of the peptide in the network for the gas-liquid interface. This results in stabilization of the foam upon exposure to the first stimulus and destabilization upon exposure to the second stimulus. In some cases, the foam is destabilized to an extent that coalescence of the dispersed gas droplets occurs and the foam collapses.

In other embodiments, the first stimulus reduces the force transmission of the peptide network at the gas-liquid interface by, for example, reducing the number and/or strength of interactions between peptides in the network. The second stimulus then increases force transmission of the peptide network at the gas-liquid interface by, for example, increasing the number and/or strength of interactions between peptides within the network. In these embodiments, the foam initially has a reduced stability and upon exposure to the second stimulus, the stability of the foam is increased.

The foam comprising the self-assembled, force-transmitting peptide network may be prepared by:
a) dissolving or dispersing a peptide capable of forming a self-assembled, force-transmitting peptide network in a liquid to form a solution or dispersion; and
b) mixing the solution or dispersion with a gas to form a foam.

The mixing may be any means of mixing liquid and gas known in the art to form foams. In some embodiments, the gas is bubbled through the liquid phase. In other embodiments, the liquid is mixed or agitated in the presence of gas. The vigorousness of agitation, or mixing or the rate of flow of gas into and through the liquid will determine the speed with which the foam forms and the size of the droplets in the dispersed gas phase as is known in the art of foam formation.

The self-assembled, force-transmitting peptide network may be formed at the fluid-fluid interface as the foam forms. During formation of the foam, more peptides migrate from the bulk phase to the interface to form the peptide network. Alternatively, the peptide network may form after agitation or mixing during a period of aging where the peptide migrates from bulk solution to the liquid-gas interface. The formation of the peptide network during or after foam formation will depend at least in part, on the concentration of peptide in the bulk solution and its affinity for the gas-liquid interface. A high concentration of peptide which has a high affinity for the gas-liquid interface, a low energy barrier for entry to the interface, and an ability to interact with other peptides will accelerate formation of the peptide network in the foam.

In some embodiments, the formation of a foam may be delayed by exposing the solution or dispersion of peptide capable of forming a self-assembled, force-transmitting peptide network to a first stimulus which reduces the likelihood of stable foam formation, for example, by reducing the affinity of the peptide for the gas-liquid interface or by causing repulsions between peptides at the gas-liquid interface. After a period of mixing the solution or dispersion with the gas, a second stimulus is introduced to the solution or dispersion which causes formation of the peptide network and stabilization of the foam.

In some embodiments, the foam may be stabilized and destabilized a plurality of times by repeating steps i) and ii), and optionally step b) if the foam has collapsed after destabilization, one or more times.

In some embodiments, the liquid phase is a polar liquid which is capable of dissolving the peptide that is capable of forming a self-assembled, force-transmitting peptide network to form a solution. Alternatively, the peptide is insoluble or only partially soluble in the polar liquid and a dispersion is formed. In other embodiments, the liquid phase is a non-polar liquid capable of dissolving the peptide to form a solution. Alternatively, the peptide is insoluble or only partially soluble in the non-polar liquid and a dispersion is formed. Examples of suitable polar liquids include, but are not limited to, water, methanol, ethanol, isopropanol, acetonitrile or mixtures thereof. Examples of suitable non-polar liquids include, but are not limited to, hydrocarbons such as pentane, hexane, octane and mixtures of hydrocarbons, liquid oils such as olive oil, sunflower oil, safflower oil, grapeseed oil, sesame oil, coconut oil, canola oil, corn oil, flaxseed oil, palm oil, palm kernel oil, peanut oil and soybean oil or triacylglycerols which are rich in unsaturated fatty acids or mixtures thereof. The gas may be any gas suitable for the application for which the foam is used. Suitable gases include, but are not limited to, air, nitrogen, oxygen, hydrogen, helium and argon.

In yet a further aspect there is provided a method of modulating the stability of an emulsion comprising a self-assembled, force-transmitting peptide network at a liquid-liquid interface; said method comprising:
ia) at a first time, exposing the liquid-liquid interface to a first stimulus that alters the chemical and/or physical properties of a peptide in the peptide network; and
iia) at a second time, exposing the liquid-liquid interface to a second stimulus that alters the chemical and/or physical properties of the peptide in the peptide network adopted upon exposure to the first stimulus.

In some embodiments, the first stimulus causes formation of the self-assembled, force-transmitting peptide network, for example, by increasing the affinity of the peptide for the liquid-liquid interface or by altering the charge or polarity of the peptide to remove repulsions or allow further interactions between peptides to occur. In some embodiments, the first stimulus causes an increase in force transmission by the peptide network by, for example, increasing the number and/or strength of the interactions between peptides in the peptide network. In these embodiments, the second stimulus causes a reduction in force transmission by the peptide network, for example, by reducing the number and/or the strength of interactions between peptides within the network, or may cause abolition of force transmission by, for example, introducing repulsions between peptides within the network and/or reducing the affinity of the peptides for the liquid-liquid interface. This results in stabilization of the emulsion upon exposure to the first stimulus and destabilization upon exposure to the second stimulus. In some cases, the emulsion is destabilized to the extent that coalescence of the dispersed phase occurs resulting in separation of the two phases.

In other embodiments, the first stimulus reduces the force transmission of the peptide network at the liquid-liquid interface by, for example, reducing the number and/or strength of interactions between peptides in the network. The second stimulus then increases the force transmission of the peptide network at the liquid-liquid interface by, for example, increasing the strength of and/or number of interactions within the network. In these embodiments, the emulsion is initially reduced in stability and upon exposure to the second stimulus, the stability of the emulsion is increased.

The emulsion comprising the self-assembled, force-transmitting peptide network may be prepared by:
A) dissolving or dispersing a peptide capable of forming a self-assembled, force-transmitting network in a first liquid to form a solution or dispersion; and
B) mixing the solution or dispersion with a second liquid which is immiscible with the first liquid to form an emulsion.

The mixing may be any means of mixing two immiscible liquids known in the art to form emulsions. Suitable means of mixing include but are not limited to agitation of the two liquids by shaking or stirring, homogenization, applying shear and pumping the two liquids into a container at high speed or pressure. The vigorousness of mixing will determine the speed at which the emulsion forms and the size of the droplets in the dispersed liquid phase as is known in the art of emulsion formation.

The self-assembled, force-transmitting peptide network may be formed at the fluid-fluid interface as the emulsion forms. During emulsion formation, more peptides migrate from the bulk phase to the interface to form the peptide network. Alternatively, the peptide network may form after the emulsion has been formed, during a period of aging where the peptide migrates from the bulk solution to the liquid-liquid interface. The formation of the peptide network during or after emulsion formation will depend on, at least in part, the concentration of the peptide in the bulk solution and its affinity for the liquid-liquid interface. A high concentration of peptide that has a high affinity for the liquid-liquid interface, a low energy barrier for entry to the interface and an ability to interact with other peptides will accelerate formation of the peptide network in the emulsion.

In some embodiments, the formation of an emulsion may be delayed by exposing the solution or dispersion formed in step A) to a first stimulus which reduces the likelihood of stable emulsion formation, for example, by causing repulsions between peptides at the liquid-liquid interface or by reducing the affinity of the peptide for the liquid-liquid interface. After a period of mixing of the first and second immiscible liquids, a second stimulus is introduced to the solution or dispersion which causes formation of the peptide network and stabilization of the emulsion.

In some embodiments, the emulsion may be stabilized and destabilized a plurality of times by repeating steps ia) and iia) and optionally step B) if the two liquid phases have separated after destabilization, one or more times.

In some embodiments, the first liquid is a polar liquid that is capable of dissolving the peptide that is capable of forming a self-assembled, force-transmitting peptide network to form a solution. In other embodiments, the peptide is not soluble or is only partially soluble in the polar liquid and a dispersion is formed. In these cases, the second liquid is a non-polar solvent that is immiscible with the polar solvent. In some embodiments the first liquid is a non-polar liquid which is capable of dissolving the peptide capable of forming a self-assembled, force-transmitting peptide network to form a solution. Alternatively, the peptide is not soluble or is only partially soluble in the non-polar liquid and a dispersion is formed. In these cases, the second liquid is a polar solvent that is immiscible with the non-polar solvent. Examples of suitable polar liquids include, but are not limited to, water, methanol, ethanol, isopropanol, acetonitrile or mixtures thereof. Examples of suitable non-polar liquids include, but are not limited to, hydrocarbons such as pentane, hexane, octane and mixtures of hydrocarbons, liquid oils such as olive oil, sunflower oil, safflower oil, grapeseed oil, sesame oil, coconut oil, canola oil, corn oil, flaxseed oil, palm oil, palm kernel oil, peanut oil and soybean oil or triacylglycerols which are rich in unsaturated fatty acids or mixtures thereof.

In order that the invention may be readily understood and put into practical effect, particular preferred embodiments will now be described by way of the following non limiting Examples.

EXAMPLES

Reagents were of analytical grade unless otherwise indicated. Ultrapure water was produced by a MilliQ water purification unit (Millipore, North Ryde, NSW, Australia) and had a resistivity of >18.2 M Ωcm. Glassware was cleaned by soaking in 2% (v/v) Decon90 (Decon Laboratories Ltd, Hove, East Sussex, UK), rinsed extensively with MilliQ water, soaked for 30 minutes in freshly prepared piranha solution (equal parts of 30% (v/v) $H_2O_2$ and 98% (v/v) $H_2SO_4$), then rinsed with copious amounts of MilliQ water, followed by final rinses with ethanol and acetone.

β-Lactoglobulin (90%), methyl mandelate (97%), mandelic acid (99%), lipase acrylic resin from *Candida antarctica* (Lipolase) and *Candida rugosa* lipase Type VII were from Sigma (St Louis, Mo., USA). Protein concentrations for β-lactoglobulin were determined using $A_{280}=1.08$ for a 1.0 mg/mL solution. Phosphate-buffered saline (PBS) contained 137 mM NaCl, 2.7 mM KCl, 12 mM $Na_2HPO_4$, 1.8 mM $KH_2PO_4$, adjusted to pH 7.4 with HCl. $Ni(NO_3)_2.6H_2O$ was laboratory grade. Crude oils (Rang Dong waxy crude oil, Arab medium crude oil) were a gift from BP. Toluene and acetonitrile were of HPLC grade.

Reversed-phase HPLC analysis of biocatalytic samples containing methyl mandelate and mandelic acid used a $C_{18}$ reversed phase column (150×4.6 mm, Jupiter 5 µm, 300 Å, Phenomenex, Torrance Calif.) and employed isocratic elution with 20% acetonitrile in 0.1% (v/v) trifluoroacetic acid (TFA). Peaks were detected by absorbance at 254 nm. Prior to HPLC analysis, biocatalytic samples obtained from peptide-stabilized toluene-in-water emulsions or acetonitrile media were diluted 1:5 in 0.1% (v/v) TFA and filtered through a 0.45 µM Teflon membrane.

Peptides were prepared by solid-phase synthesis and were synthesised by Auspep Pty Ltd (SEQ ID NO:1, SEQ ID NO:2, Parkville, Victoria, Australia), GLS Biochem (Shanghai) Ltd (SEQ ID NO:3, SEQ ID NO:9, SEQ ID NO:10, Shanghai, China) or Genscript Corporation (SEQ ID NO:2, SEQ ID NO:4, SEQ ID NO:6, SEQ ID NO:7, SEQ ID NO:8, SEQ ID NO:11, SEQ ID NO:12, SEQ ID NO:13, SEQ ID NO:14, SEQ ID NO:15, Piscataway, N.J., USA) under instruction. SEQ ID NO:5 may be made by solid-phase synthesis in the same manner. Peptide purity was ≧95% in all cases. Following receipt, peptides were dissolved at a known weight concentration (0.5-0.7 mg/mL) in MilliQ water and aliquots of peptide (0.2-0.5 mL) were lyophilized. Lyophilized peptide aliquots were stored at −80° C. and were warmed to room temperature and dissolved in buffer immediately before use. Peptide concentrations were determined using quantitative amino acid analysis (QAA, Australian Proteome Analysis Facility, Sydney, NSW, Australia). The sequences of peptides designated SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 and SEQ ID NO:15 are shown in Table 4.

TABLE 4

Peptide sequences

| Peptide | Sequence |
| --- | --- |
| SEQ ID NO: 1 | Ac-MKQLADSLMQLARQVSRLESA-CONH$_2$ |
| SEQ ID NO: 2 | Ac-MKQLADSLHQLARQVSRLEHA-CONH$_2$ |
| SEQ ID NO: 3 | Ac-LMQLARQMKQLADSLMQLARQVSRLESA-CONH$_2$ |
| SEQ ID NO: 4 | Ac-MKELADSLMQLARQVDRLESA-CONH$_2$ |
| SEQ ID NO: 5 | Ac-MKQLADSLHQLAHQVSHLEHA-CONH$_2$ |
| SEQ ID NO: 6 | Ac-PHFRFSFSP-CONH$_2$ |
| SEQ ID NO: 7 | Ac-PHFSFSFSP-CONH$_2$ |
| SEQ ID NO: 8 | Ac-PSFRFSFSP-CONH$_2$ |
| SEQ ID NO: 9 | Ac-MEELADSLEELARQVEELESA-CONH$_2$ |
| SEQ ID NO: 10 | Ac-MKKLADSLKKLARQVKKLESA-CONH$_2$ |

TABLE 4-continued

Peptide sequences

| Peptide | Sequence |
|---|---|
| SEQ ID NO: 11 | Ac-PHFHFSFSP-CONH$_2$ |
| SEQ ID NO: 12 | Ac-PFFSFHFSP-CONH$_2$ |
| SEQ ID NO: 13 | Ac-MKQLADSLHQLAHKVSHLEHA-CONH$_2$ |
| SEQ ID NO: 14 | Ac-EISALEKEISALEKEISALEK-CONH$_2$ |
| SEQ ID NO: 15 | Ac-KISALKEKISALKEKISALKE-CONH$_2$ |

Cambridge Interfacial Tensiometer (CIT)

Instrument configuration and data processing were as previously reported (Jones and Middelberg 2002c, Jones and Middelberg 2002a). Fibre optic T-pieces were mounted over a stainless steel bath (external dimensions 157×49×20 mm, internal dimensions 80×20×3 mm) or a Teflon bath of similar dimensions. T-pieces were brought into alignment in contact with each other on a meniscus ca. 2 mm above the bath edge, obtained by filling the bath with 8.0 mL MilliQ water in the case of the stainless steel bath, or 6.5 mL MilliQ water in the case of the Teflon bath.

Before first use, mounted T-pieces were passivated with β-lactoglobulin by conducting an initial force transmission experiment using 0.1 mg/mL β-lactoglobulin in phosphate-buffered saline. Following 60 minutes aging, an interfacial elasticity modulus of 150 mN/m and maximum interfacial stress of 14 mN/m were obtained for 0.1 mg/mL β-lactoglobulin in PBS, similar to previously published results (Jones and Middelberg, 2002c).

Peptide Force Transmission

Lyophilized peptide aliquots (25-90 nmol) were brought from storage at −80° C., warmed to room temperature, then dissolved in buffer immediately before use. An aliquot of peptide stock was diluted in the same buffer to the desired final concentration (typically 5 µM) in a volume of 7-9 mL. A fixed volume (8.0 mL, steel bath, or 6.5 mL, Teflon bath) of the peptide solution was transferred into the CIT bath at t=0 to give a meniscus approximately 1-2 mm above the CIT bath edge and level with pre-aligned T-pieces at an initial separation of 1000 µm. After aging (60 minutes unless otherwise indicated), interfaces were subjected to eight replicate load cycles to 5% strain (used for averaging), followed by a single load cycle to 300% strain, using a motor speed set to 100-200 µm/s with 250-300 Hz data acquisition. Where modification of a pre-formed interface by addition of a stimulus which alters the physical and/or chemical properties of the peptide was desired, a small volume (typically less than 200 µL) of a concentrated solution of the stimulus was pipetted into the CIT bath beneath the T-bars without disturbing the interface between the T-pieces, and the interface was allowed to age further before load cycles to 5% and 300% strain were repeated. Between experiments, the T-pieces and bath were rinsed in situ with ten changes of MilliQ water. Where necessary to remove any residual metal ion, the CIT bath was soaked briefly in 5 mM EDTA before rinsing with MilliQ water.

The interfacial elasticity modulus was determined as the slope of the interfacial stress-strain curve to 1% strain (data pooled from 8 replicate load cycles on a single interface), divided by 1% strain. Values of maximum interfacial stress were read directly from the interfacial stress-strain curve to 300% strain.

Circular Dichroism

Spectra of 2.5 µM peptide having SEQ ID NO:3 were recorded in mixed 1 mM sodium phosphate, 1 mM sodium citrate, 1 mM sodium borate buffer at pH 3.0, 6.0, 8.0 or 11.0 from 260-190 nm on a Jasco J-810 spectropolarimeter (Jasco Inc., Easton, Md., USA) at a scan speed of 50 nm/min using 0.5 nm data pitch, 0.5 nm bandwidth, 4 sec response time and 5 accumulations. Buffer baselines were recorded for each pH and used to correct the spectrum recorded for peptide at the same pH.

Spectra of 100 µM peptide having SEQ ID NO:2 were recorded in 25 mM MOPS, pH 6.2 containing either 100 µM CuSO$_4$, 100 µM ZnSO$_4$, 100 µM Ni(NO$_3$)$_2$, or 100 µM EDTA, from 260-190 nm on a Jasco J-810 circular dichroism spectrometer at 50 nm/min scan rate, with 0.1 nm data pitch, 1 nm bandwidth, 2 sec response time and 5 accumulations.

Interfacial Tension

In some cases, interfacial tension measurements were made using drop tensiometry.

Peptide having SEQ ID NO:2 (5 µM in 25 mM HEPES, 100 mM NaCl, pH 7.4 containing 100 µM CuSO$_4$, 100 µM Ni(NO$_3$)$_2$ or 100 µM EDTA) was filled into a glass syringe attached to a needle of known external diameter. The needle was inverted and positioned with the tip inside the humidity chamber of a Krüss Drop Shape Analysis System DSA 10 (Krüss GmbH, Hamburg, Germany) located on an anti-vibration table. For each time course, at time=0 seconds, a drop of 10-20 µL initial volume was formed containing peptide having SEQ ID NO:2. Changes in the interfacial tension of the drop were determined over 500 seconds by axisymmetric drop shape analysis in conjunction with manufacturer-supplied software prop Shape Analysis 1.10. A minimum of 3 drops of peptide solution were formed and discarded immediately before each drop measurement, to avoid accumulation of contaminants. Parallel experiments using buffer in the absence of peptide showed a stable interfacial tension, indicating that very low levels of any surface-active contaminant were present.

Alternately, interfacial tension was determined by bubble tensiometry using the same instrumentation as described for drop tensiometry. A solution of 5 µM peptide having SEQ ID NO:2 in 25 mM HEPES, pH 7.4 containing 100 µM ZnSO$_4$ or EDTA, or 5 µM peptide having SEQ ID NO:2 in 25 mM HEPES acidified to pH 3.6 with H$_2$SO$_4$ was filled into a quartz cuvette (Hellma GmbH & Co., Müllheim, Germany). Air bubbles (ca. 9 µL) were formed inside the cuvette using an inverted needle connected to a U-shaped needle of known external diameter. Changes in the interfacial tension were determined automatically over 1000 s by axisymmetric bubble shape analysis. A minimum of 3 air bubbles were formed and discarded immediately before each bubble measured, to avoid accumulation of contaminants. Interfacial tension at 1000 s was determined as an average of 15 values determined from bubble shape analysis. Parallel experiments in buffer in the absence of peptide showed a stable interfacial tension close to 73 mN/m, indicating that insignificant levels of surface-active contaminant were present.

Emulsion Preparation

Oil-in-water emulsions were prepared by vigorous mechanical stirring of an aqueous solution of a peptide of choice with an oil of choice, using an Ystral X10 rotor-stator homogenizer (Ystral GmbH, Ballrechten-Dottingen, Germany) operating at the maximum speed of 24,000 rpm for 3 minutes. The peptide solution and oil had a combined volume of up to 3.5 mL and were homogenized in a 4 mL glass vial into which the homogenizer dispersing tool was inserted. Typical oil volume fractions were 10-20%. Immediately after homogenization, a sample of the emulsion was diluted in buffer and the optical density at 500 nm determined. The emulsifying activity index (EAI) was calculated according to Cameron (Cameron et al., 1991) in units of square meters of interface stabilized per gram of added emulsifier:

$$EAI = \frac{2T}{1000 \times c(1-\phi)} \quad (1)$$

where T is the turbidity, c is the emulsifier concentration in mg mL$^{-1}$, and $\phi$ is the oil volume fraction in the emulsion. Turbidity is calculated from the optical density at 500 nm as:

$$T = \frac{2.303 \times OD_{500} \times D}{pathlength} \quad (2)$$

where D is the dilution factor (typically 100-200) and the pathlength is given in meters (0.01 m=1 cm in this case).

Foam Preparation

Figure 5:
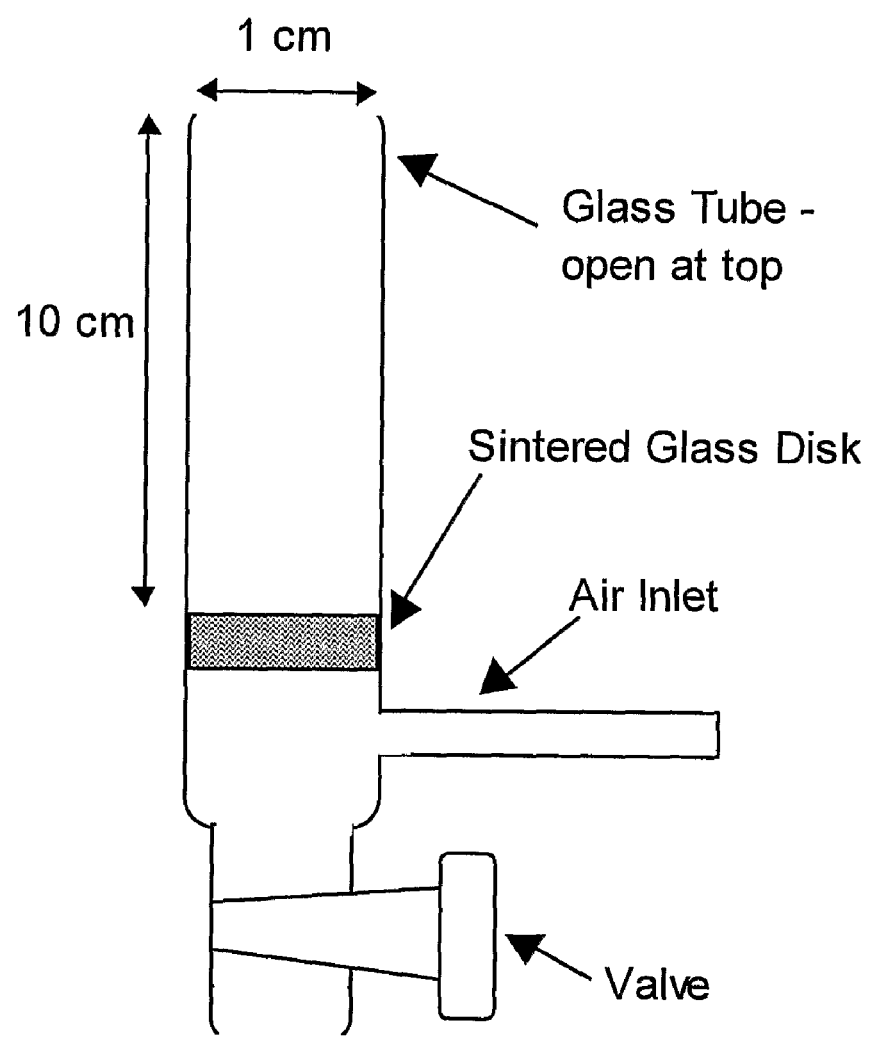
FIG. 5 visually represents the design of an apparatus used to test the stability of peptide-containing foams generated from aqueous solutions having different compositions.

Peptide-containing foams were prepared by pipetting an aliquot (0.8 mL) of peptide solution into a custom-made glass apparatus as shown in FIG. 5. Air was then bubbled through the sintered filter of the apparatus for approximately 6 seconds to produce a column of foam. The stability of the foam was observed visually and the time required for partial or complete foam collapse was noted. To modulate the stability of the foam, an aliquot (typically 2-10 µL) of a concentrated stock solution was added to the glass apparatus to change the bulk solution composition before production of a new foam. In some cases, addition of the stock solution to the top of an existing column of foam caused partial or complete collapse of the foam.

Example 1

Force Transmission at the Air-Water Interface by a Peptide Network Formed from Peptides having SEQ ID NO:2 at pH 8

A network was allowed to self-assemble over 60 minutes at the air-water interface from a solution of peptides having SEQ ID NO:2 (3.3 µM in 1 mM sodium phosphate, 1 mM sodium citrate and 1 mM sodium borate, pH 8). Eight replicate load cycles to 5% strain were carried out. Linear regression analysis for 1% strain on the pooled data gave an interfacial elasticity modulus of 81.4 mN/m. A single load cycle to high strain gave a maximum interfacial stress of 1.9 mN/m at 12% strain. The results show that peptide networks formed from peptides having SEQ ID NO:2 transmit force at an air-water interface at pH 8.

Example 2

Force Transmission at the Air-Water Interface by a Peptide Network Formed from Peptides having SEQ ID NO:2 at pH 3.

The experiment described in Example 1 was repeated with peptides having SEQ ID NO:2 in the same buffer except at pH 3. After aging, the interfacial elasticity modulus was 19.7 mN/m and the maximum interfacial stress was 0.3 mN/m. The results show that force transmission in a peptide network formed from peptides having SEQ ID NO:2 was essentially abolished at pH 3.

Example 3

Force Transmission at the Air-Water Interface by a Peptide Network Formed from Peptides having SEQ ID NO:1 at pH 8

The experiment described in Example 1 was repeated with peptides having SEQ ID NO:1 at pH 8 and at a concentration of 7.0 µM. After aging, the interfacial elasticity modulus was 18.2 mN/m and the maximum interfacial stress was 0.3 mN/m. As also previously shown (Jones and Middelberg, 2002b) peptides having SEQ ID NO:1 lack the ability to form an interfacial peptide network.

Example 4

Force Transmission at the Air-Water Interface by Surfactant Tween 80

An air-water interface was prepared using the surface active agent Tween 80 (0.02% w/v in MilliQ water). After aging, the interfacial elasticity modulus was 9.5 mN/m and the maximum interfacial stress was 0.4 mN/m. The results show that Tween 80 is a surface active agent which lacks the ability to form an interfacial network.

Example 5

Disruption of Force Transmission at the Air-Water Interface by a Peptide Network formed from Peptides having SEQ ID NO:2

An air-water interface was prepared using peptides having SEQ ID NO:2 (10 µM in 1 mM sodium phosphate, 1 mM sodium citrate and 1 mM sodium borate, pH 8). After aging, the interfacial elasticity modulus was 67.0 mN/m and the maximum interfacial stress was 1.2 mN/m at 11% strain. HCl was then added to reduce the pH of the solution to 3.0. After aging, the interfacial elasticity modulus was 4 mN/m and the maximum interfacial stress was 0.2 mN/m. These results indicate that pH can affect the ability of a peptide to form a network and can disrupt and disperse a network that was already formed at an interface.

Example 6

Effects of Added Ni(II) on Force Transmission at the Air-Water Interface by a Peptide Network Formed from Peptides having SEQ ID NO:2

Air-water interfaces were prepared using peptides having SEQ ID NO:2 (3.5 µM in 25 mM HEPES, 100 mM NaCl at pH 7.4 containing either 1 mM Ni(NO$_3$)$_2$ or 5 mM EDTA). After aging, the interfacial elasticity modulus was 105.3 mN/m in the presence of Ni(II) and 32.6 mN/m in the presence of EDTA and the maximum interfacial stress was 6.1 mN/m at 29% strain in the presence of Ni(II) and 0.5 mN/m in the presence of EDTA. In comparison with the peptide network of peptides having SEQ ID NO:2 alone, without added Ni(II) or EDTA, in the same buffer and under same conditions, the presence of Ni(II) increases the interfacial elasticity modulus from 65.8 mN/m to 105.3 mN/m and the maximum interfacial stress from 1.6 mN/m to 6.1 mN/m. On the other hand, the presence of EDTA, a metal chelating agent, decreased the interfacial elasticity modulus from 65.8 mN/m to 32 mN/m and the maximum interfacial stress from 1.6 mN/m to 0.5 mN/m. These results suggest that peptides having SEQ ID NO:2 bind adventitious metal ions during normal handling and the presence of the metal ions strengthens the peptide network.

Example 7

Disruption of Force Transmission at the Air-Water Interface by a Ni(II)-Containing Peptide Network Formed from Peptides having SEQ ID NO:2

An air-water interface was prepared using peptides having SEQ ID NO:2 (3.5 µM in 25 mM HEPES buffer, 100 mM NaCl, pH 7.4 in the presence of 1 mM Ni(NO$_3$)$_2$). After aging, the interfacial elasticity modulus was 103.4 mN/m and the maximum interfacial stress was 5.9 mN/m at 29% strain. EDTA was then added to give a bulk solution concentration of 5 mM. After EDTA addition and further aging, the interfacial elasticity modulus was 49.0 mN/m and the maximum interfacial stress was 1.0 mN/m at 12% strain.

Example 8

Effects of added Zn(II) on Force Transmission at the Air-Water Interface by a Peptide Network Formed from Peptides having SEQ ID NO:2 and Disruption of Force Transmission by Addition of EDTA An air-water interface was prepared using peptides having SEQ ID NO:2 (5.0 µM in 25 mM HEPES buffer, pH 7.4, in the absence of added metal ions). After aging, the interfacial elasticity modulus was 35 mN/m and the maximum interfacial stress was 0.5 mN/m. ZnSO$_4$ was then added to give a bulk solution concentration of 100 µM. After ZnSO$_4$ addition and aging, the interfacial elasticity modulus was 131 mN/m and the maximum interfacial stress was 8.1 mN/m at 41% strain. EDTA was then added to give a bulk solution concentration of 200 µM. After EDTA addition and further aging, the interfacial elasticity modulus was 30 mN/m and the maximum interfacial stress was 0.6 mN/m.

Example 9

Disruption of Force Transmission at the Air-Water Interface by a Zn(II)-Containing Peptide Network Formed from Peptides having SEQ ID NO:2 by the Addition of Acid and Restoration of Force Transmission by Neutralization with Base An air-water interface was prepared using peptides having SEQ ID NO:2 (5.0 µM in 25 mM HEPES, 100 mM NaCl, pH 7.4 in the presence of 100 µM ZnSO$_4$). After aging, the interfacial elasticity modulus was 103 mN/m and the maximum interfacial stress was 6.9 mN/m at 46% strain. HCl was then added to reduce the pH of the solution to 3.8. After HCl addition and further aging, the interfacial elasticity modulus was 4 mN/m and the maximum interfacial stress was 0.1 mN/m. NaOH was then added to restore the pH of the solution to 7.4. After NaOH addition and further aging, the interfacial elasticity modulus was 93 mN/m and the maximum interfacial stress was 6.9 mN/m at 40% strain.

Example 10

Effects of Added Cu(II) on Force Transmission at the Air-Water Interface by a Peptide Network Formed from Peptides having SEQ ID NO:2 and Disruption of Force Transmission by Addition of EDTA An air-water interface was prepared using peptides having SEQ ID NO:2 (5.0 µM in 25 mM HEPES buffer, 100 mM NaCl, pH 7.4) in the absence of added metal ions. After aging, the interfacial elasticity modulus was 30 mN/m and the maximum interfacial stress was 0.5 mN/m. CuSO$_4$ was added to give a bulk solution concentration of 100 µM. After CuSO$_4$ addition and further aging, the interfacial elasticity modulus was 118 mN/m and the maximum interfacial stress was 8.4 mN/m at 33% strain. EDTA was then added to give a bulk solution concentration of 100 µM. After EDTA addition and further aging, the interfacial elasticity modulus was 19 mN/m and the maximum interfacial stress was 0.4 mN/m.

Example 11

Disruption of Force Transmission at the Air-Water Interface by a Cu(II)-Containing Peptide Network Formed from Peptides having SEQ ID NO:2 by the Addition of Acid and Restoration of Force Transmission by Neutralization with Base An air-water interface was prepared using peptides having SEQ ID NO:2 (5.0 µM in 25 mM HEPES, 100 mM NaCl, pH 7.4 containing 100 µM CuSO$_4$). After aging, the interfacial elasticity modulus was 235 mN/m and the maximum interfacial stress was 11.1 mN/m at 76% strain. HCl was then added to reduce the pH of the solution to 3.8. After the HCl addition and further aging, the interfacial modulus was 15 mN/m and the maximum interfacial stress was 0.4 mN/m. NaOH was then added to restore the pH of the solution to 7.4. After NaOH addition and further aging, the interfacial elasticity modulus was 204 mN/m and the maximum interfacial stress was 11.7 mN/m at 62% strain.

Example 12

Metal Ion Dependence of Kinetics of Adsorption at the Air-Water Interface for Peptides having SEQ ID NO:2

Drop tensiometry measurements were made as described above for solutions of peptides having SEQ ID NO:2 (5.0 µM in 25 mM HEPES, 100 mM NaCl at pH 7.4 and containing either 100 µM ZnSO$_4$, 100 µM CuSO$_4$, 100 µM Ni(NO$_3$)$_2$ or 100 µM EDTA). A drop of solution of peptide having SEQ ID NO:2 was formed at 10-20 µL initial volume and changes in the interfacial tension of the drop were determined over 500 seconds by axisymmetric drop shape analysis. In the presence of 100 µM EDTA, peptide having SEQ ID NO:2 rapidly lowered the interfacial tension of the drop, indicating rapid adsorption at the air-water interface. The reduction in interfacial tension occurred as a single kinetic phase. In the presence of 100 µM Zn(II), and particularly in the presence of 100 µM Ni(II), the reduction in interfacial tension was much slower but still monophasic. In the presence of 100 µM Cu(II), the shape of the curve was distinctly different, showing two kinetic phases. The results are consistent with a model in which peptide having SEQ ID NO:2 is highly structured in bulk solution in the presence of Cu(II) (see also Example 13) and experiences a kinetic barrier to entering the interface once moderate interfacial coverage has been achieved (Middelberg et al., 2000). The final interfacial tension is similar for peptide having SEQ ID NO:2 in the presence of all additives, indicating that in this case, the peptide is present at a similar surface excess at the interface whether networked or not. The slower adsorption of peptide having SEQ ID NO:2 in the presence of Zn(II) or Ni(II) may indicate that the peptide is present in the form of larger complexes, in which the metal crosslinks different peptide molecules.

Example 13

Effect of Added Metal Ion on Bulk Solution Structure for Peptide having SEQ ID NO:2

To clarify the mode of action of added metal ion on force transmission by peptides having SEQ ID NO:2, circular dichroism spectra were recorded for the peptide in bulk solution in the presence of added Cu(II), Zn(II), Ni(II) or EDTA. Solutions of peptide having SEQ ID NO:2 were prepared (100 μM peptide in 25 mM MOPS, pH 6.2 containing either 100 μM $CuSO_4$, 100 μM $ZnSO_4$, 100 μM $Ni(NO_3)_2$, or 100 μM EDTA) and circular dichroism spectra were recorded. The spectra in the presence of EDTA, Zn(II) or Ni(II) are equivalent to each other and are dominated by the features of random coil peptide spectra, indicating that the addition of Zn(II) or Ni(II) to peptide having SEQ ID NO:2 does not significantly change the conformation of the peptide in bulk solution, and that the peptide is largely unstructured under these conditions. However, the spectrum for peptide having SEQ ID NO:2 in the presence of Cu(II) is dominated by the characteristic double minimum of an α-helical peptide conformation, indicating that binding of Cu(II) to the peptide stabilizes the helical structure. The results suggest that Cu(II) may act by a different mechanism to Zn(II) or Ni(II) in promoting network formation at the interface, with intramolecular helix stabilization more dominant than intermolecular peptide-peptide cross-linking for Cu(II), while intermolecular peptide-peptide cross-linking may play a dominant role for Zn(II) and Ni(II).

Figure 4:
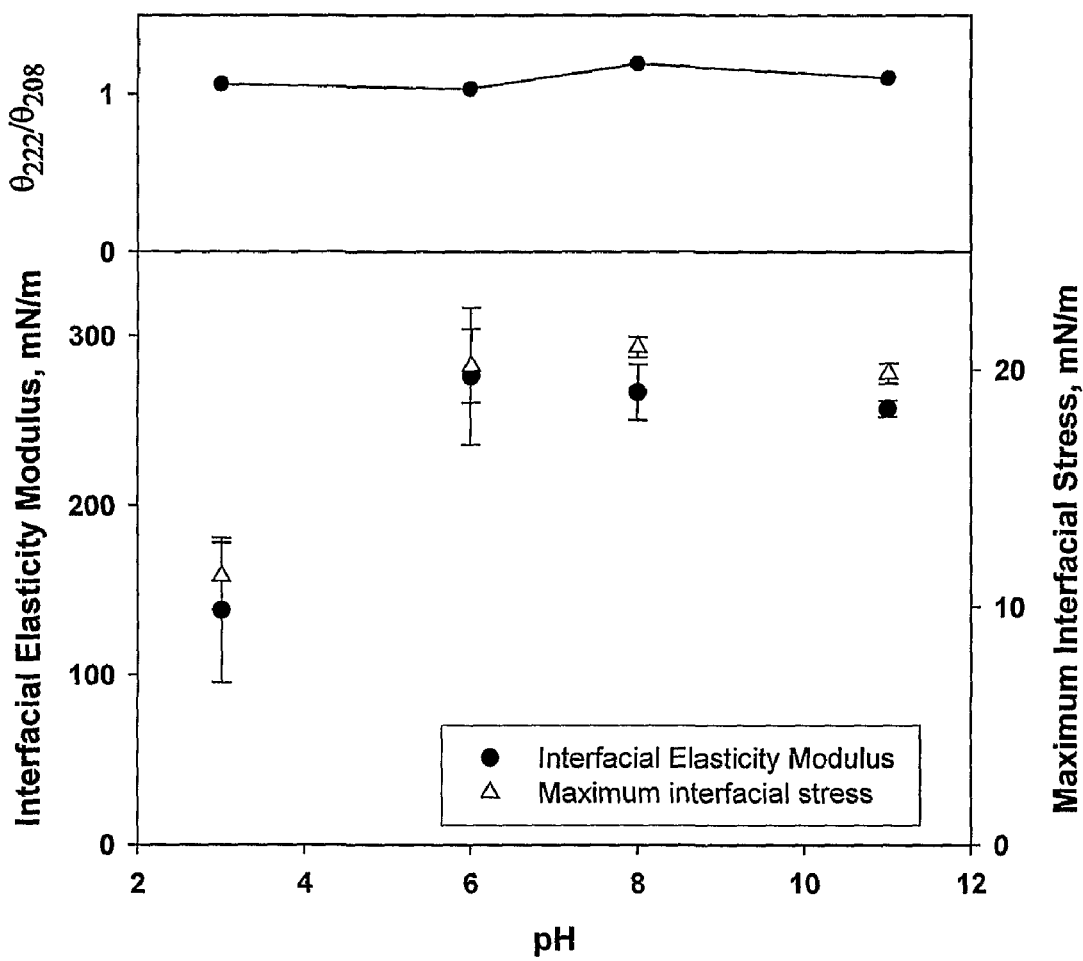
FIG. 4 graphically represents the pH dependence of the secondary structure of, and force transmission by, a peptide network formed from peptides having SEQ ID NO:3.

Example 14 pH Dependence of Peptide Networks Formed at the Air-Water Interface from Peptides having SEQ ID NO:3, and Peptide Secondary Structure in Bulk Solution Air-water interfaces were prepared using peptides having SEQ ID NO:3 (2.5 μM in 1 mM sodium phosphate, 1 mM sodium citrate, 1 mM sodium borate at pH 3.0, 6.0, 8.0 or 11.0). Circular dichroism measurements (FIG. 4, top graph) gave $\theta_{222}/\theta_{208}$ ratios consistent with a coiled-coil structure for SEQ ID NO:3 as shown in FIG. 1,C at all pH values. The interfacial elasticity modulus and maximum interfacial stress were determined in replicate at each pH. Data points show mean values with error bars to two standard deviations from mean. FIG. 4, bottom graph, shows a plot of interfacial elasticity modulus or maximum interfacial stress versus pH.

At pH 8, peptide networks formed by peptides having SEQ ID NO:3 display an average interfacial elasticity modulus of 266.8 mN/m and an average maximum interfacial stress at 20.5 mN/m.

At pH 6.0 and 11.0, force transmission by a peptide network formed from peptides having SEQ ID NO:3 is equivalent within experimental error to that measured at pH 8.0. However, at pH 3.0 the values of the interfacial elasticity modulus and maximum interfacial stress fall by a factor of two. It appears that an increased positive charge on peptides having SEQ ID NO:3 at lower pH weakens either the affinity of peptides having SEQ ID NO:3 for the hydrophobic air-water interface or the strengths of interactions between peptides having SEQ ID NO:3 in the interface, without affecting the peptide secondary structure in bulk solution.

Example 15

Effect of Chaotropic Agent on Force Transmission at the Air-Water Interface by Peptide Network Formed from Peptides having SEQ ID NO:3

An air-water interface was prepared using peptides having SEQ ID NO:3 (1.0 μM in 1 mM sodium phosphate, 1 mM sodium citrate, 1 mM sodium borate at pH 8, in the presence or absence of 6.0 M urea). After aging, the interfacial elasticity modulus was 17.8 mN/m in the presence of urea and 273.2 mN/m in the absence of urea and the maximum interfacial stress was 0.3 mN/m in the presence of urea and 17.7 mN/m at 19% strain in the absence of urea.

The results show that the presence of a chaotropic agent disrupts the secondary structure of the peptide and/or intermolecular interactions between peptides and thereby disrupts the peptide network and abolishes force transmission.

Example 16

Effect of Metal Ion Addition on the Emulsifying Properties of a Peptide having SEQ ID NO:2

An oil-in-water emulsion was prepared using peptide having SEQ ID NO:2 (63 μM in 1.8 mL 25 mM MOPS, 100 mM NaCl, pH 6.2 containing 70 μM $CuSO_4$) and silicone oil (10% volume fraction).

The EAI was 106 $m^2 g^{-1}$. To determine the effects of metal ions on emulsification by peptides having SEQ ID NO:2, the experiment was repeated in the same buffer in the presence of 100 μM EDTA. An EAI of 90 $m^2 g^{-1}$ was determined for peptide having SEQ ID NO:2 in the presence of 100 μM EDTA.

For comparison, a silicone oil-in-water emulsion was also prepared using peptide having SEQ ID NO:2 in low-salt buffer. An oil-in-water emulsion was prepared using peptide having SEQ ID NO:2 (63 μM in 25 mM MOPS, pH 6.2 containing 70 μM $CuSO_4$, in the absence of added NaCl) and silicone oil (10% volume fraction). The EAI was determined to be 91 $m^2 g^{-1}$. Three separate 1 mL samples of the peptide-containing emulsion were removed into 4 mL glass vials. No additions were made to the first vial. EDTA was added to the second vial to give a concentration of 1 mM. HCl was added to the third vial to lower the pH to approximately 2.0. The three aliquots were mixed gently on a tube roller at room temperature and the EAI was redetermined after 10 minutes. After this time, the EAI was 89 $m^2 g^{-1}$ in the absence of additives, 92 $m^2 g^{-1}$ in the presence of added HCl and 1 $m^2 g^{-1}$ in the presence of added EDTA. In the presence of added EDTA the oil and water phases separated completely within 1 minute, indicating switching of the emulsion.

Visual comparison of emulsions formed in the presence of Cu(II) and their breaking with the addition of EDTA was also performed. An oil-in-water emulsion was prepared using peptide having SEQ ID NO:2 (63 μM in 25 mM MOPS, pH 6.2 containing 70 μM $CuSO_4$ in the absence of added NaCl), and silicone oil (10% volume fraction). The emulsion was divided into two separate 1 mL samples in 4 mL glass vials. No additions were made to the first vial. EDTA was added to the second vial to give a concentration of 1 mM. Coalescence was observed to begin within several minutes after EDTA addition.

For comparison, an oil-in-water emulsion was prepared using peptide having SEQ ID NO:1 (200 μg mL$^{-1}$ in 1.8 mL 25 mM HEPES, 100 mM NaCl, pH 7.4) and silicone oil (10% volume fraction). The EAI was 33 m$^2$ g$^{-1}$, significantly lower than for peptide having SEQ ID NO:2 under network-forming conditions.

For comparison, a 10% silicone oil-in-water emulsion was also prepared using the protein β-casein (156 μg mL$^{-1}$ in 1 mM Na$^+$phosphate, 50 mM NaCl, pH 7.0), an emulsifier used extensively in food products. The EAI was 49 m$^2$ g$^{-1}$ (averaged over two emulsification trials), significantly lower than for peptide having SEQ ID NO:2 under network-forming conditions.

For comparison, a 10% silicone oil-in-water emulsion was also prepared using the protein β-lactoglobulin, (156 μg mL$^{-1}$ in 1 mM Na$^+$ phosphate, 50 mM NaCl, pH 7.0), an emulsifier also used extensively in food products. The EAI was 51 m$^2$ g$^{-1}$ (averaged over two emulsification trials), significantly lower than for peptide having SEQ ID NO:2 under network-forming conditions.

Example 17

Disruption of Zn(II)-Enhanced Force Transmission at the Air-Water Interface by a Peptide Network Formed from Peptides having SEQ ID NO:2 by the Addition of Acid and Restoration of Force Transmission by Neutralization with Base An air-water interface was prepared using peptide having SEQ ID NO:2 (5.0 μM in 25 mM HEPES, pH 7.4). After aging, the interfacial elasticity modulus was less than 30 mN/m and the maximum interfacial stress was 0.5 mN/m. ZnSO$_4$ was then added to give a bulk solution concentration of 100 μM. After aging, the interfacial elasticity modulus was 121 mN/m and the maximum interfacial stress was 6.9 mN/m. H$_2$SO$_4$ was then added to reduce the pH to 3.6. after H$_2$SO$_4$ addition and further aging, the interfacial elasticity modulus was 17 mN/m and the maximum interfacial stress was 0.2 mN/m. NaOH was then added to restore the pH to 7.4. After NaOH addition and further aging, the interfacial elasticity modulus was 120 mN/m and the maximum interfacial stress was 7.8 mN/m.

Example 18

Bubble Tensiometry of Interfacial Networks Formed from Peptides having SEQ ID NO:2

Bubble tensiometry measurements were made as described above for solutions of peptide having SEQ ID NO:2 (5 μM in 25 mM HEPES, pH 7.4 containing 100 μM ZnSO$_4$ or 100 μM EDTA or 5.0 μM in 25 mM HEPES adjusted to pH 3.6 by addition of H$_2$SO$_4$). Changes in the interfacial tension were determined automatically over 1000 s by axisymmetric bubble shape analysis. Interfacial tension at 1000 seconds was determined as an average of 15 values determined from bubble shape analysis. Parallel experiments in buffer in the absence of peptide showed a stable interfacial tension close to 73 mN/m, indicating that insignificant levels of surface-active contaminant were present.

Bubble tensiometry showed that peptides having SEQ ID NO:2 adsorbed at the air-water interface to a similar extent at neutral pH in the presence or absence of Zn(II) ions, or following acidification to pH 3.6. In the presence of EDTA, added to scavenge adventitious metal ions, peptides having SEQ ID NO:2 rapidly lowered the interfacial tension at the air-water interface, achieving a value of 52.9 mN/m after 1000 s. When 100 μM Zn(II) was present, the interfacial tension at 1000 s was 52.1 mN/m, while inclusion of H$_2$SO$_4$ to a pH of 3.6 gave a slightly higher interfacial tension of 54.6 mN/m. The results show that formation of network rather than non-network states was therefore not accompanied by large changes in peptide concentration at the interface.

Example 19

Effect of Acidification on Emulsifying Properties of a Peptide Network containing Zinc(II) Ions and Peptides having SEQ ID NO:2

An oil-in-water emulsion was prepared using peptide having SEQ ID NO:2 (60 μM in 25 mM HEPES, pH 7.4 containing 200 μM ZnSO$_4$) and toluene (20% volume fraction). The EAI was 360 m$^2$ g$^{-1}$.

For enhanced visual observation of emulsion switching, a second oil-in-water emulsion was prepared using peptides having SEQ ID NO:2 (60 μM in 25 mM HEPES, pH 7.4 containing 250 μM ZnSO$_4$ and 10 μM methylene blue dye) and toluene (20% volume fraction containing 50 μM Sudan III dye). The peptide —Zn(II) network stabilized emulsion was stable to phase coalescence over 20 hours at room temperature. However, when an aliquot (8 μL) of acid (1.9 M H$_2$SO$_4$) was added to 1 mL emulsion with stirring, gross separation of the oil (red) and water (blue) phases occurred in a matter of seconds. Clean recovery of both phases occurred within 10 minutes.

Example 20

Effect of EDTA on Emulsifying Properties of a Peptide Network Containing Zinc(II) Ions and Peptides having SEQ ID NO:2

The experiment described in Example 19 was repeated but instead of addition of acid, EDTA was substituted as described below.

When an aliquot (8 μL) of chelating agent (100 mM Na$^+$ ethylene-diamine tetraacetate (EDTA), pH 8.0) was added to 1 mL 20% (v/v) toluene-in-water emulsion with stirring, the emulsion rapidly coalesced with gross separation of the oil (red) and water (blue) phases occurring in a matter of seconds and clean recovery of both phases occurred within 20 minutes.

Example 21

Disruption of Force Transmission at the Air-Water Interface by a Peptide Network Formed from Peptides having SEQ ID NO:9 by the Addition of Base and Restoration of Force Transmission by Neutralization with Acid An air-water interface was prepared using peptide having SEQ ID NO:9 (5.0 μM in mixed 1 mM sodium phosphate, 1 mM sodium citrate, 1 mM sodium borate buffer at pH 4.0 containing 1 mM spermine to act as a proton transfer agent). After aging, the interfacial elasticity modulus was 496 mN/m and the maximum interfacial stress was 16.9 mN/m at 45% strain. NaOH was added to increase the pH of the solution to 8.0. After NaOH addition and further aging the interfacial elasticity modulus was 7 mN/m and the maximum interfacial stress was 0.3 mN/m. HCl was then added to restore the pH of the solution to 4.0. After HCl addition and further aging, the elasticity modulus was 355 mN/m and the maximum interfacial stress was 17.0 mN/m at 48% strain.

Example 22

Disruption of Force Transmission at the Air-Water Interface by a Peptide Network Formed from Peptides having SEQ ID NO:10 by the Addition of Acid and Restoration of Force Transmission by Neutralization with Base An air-water interface was prepared using peptide having SEQ ID NO:10 (5.0 μM in mixed 1 mM sodium phosphate, 1 mM sodium citrate, 1 mM sodium borate at pH 11.0). After aging, the interfacial elasticity modulus was 91 mN/m and the maximum interfacial stress was 4.8 mN/m at 36% strain. HCl was then added to reduce the pH of the solution below 7.0. After HCl addition and further aging, the interfacial elasticity modulus was 33 mN/m and the maximum interfacial stress was 0.9 mN/m. NaOH was then added to restore the pH of the solution to 11.0. After NaOH addition and further aging, the interfacial elasticity modulus was 65 mN/m and the maximum interfacial stress was 4.7 mN/m at 30% strain.

Example 23

Alteration of Force Transmission at the Air-Water Interface by a Mixed Peptide Network Formed from Peptides having SEQ ID NO:9 and Peptides having SEQ ID NO:10 by the Addition of Acid and Subsequent Neutralization with Base An air-water interface was prepared using peptide having SEQ ID NO:9 and peptide having SEQ ID NO:10 (2.5 μM each in mixed 1 mM sodium phosphate, 1 mM sodium citrate, 1 mM sodium borate at pH 7.0). After aging, the interfacial elasticity modulus was 53 mN/m and the maximum interfacial stress was 2.0 mN/m at 77% strain. HCl was then added to reduce the pH of the solution to 3.0. After HCl addition and further aging, the interfacial elasticity modulus was 146 mN/m and the maximum interfacial stress was 9.1 mN/m at 26% strain. NaOH was then added to restore the pH of the solution to 7.0. After NaOH addition and further aging, the interfacial elasticity modulus was 60 mN/m and the maximum interfacial stress was 2.6 mN/m at 69% strain.

Example 24

Enhancement of Force Transmission at the Air-Water Interface by a Peptide Network Formed from Peptides having SEQ ID NO:9 by the Addition of $Ca^{2+}$ Ions An air-water interface was prepared using peptide having SEQ ID NO:9 (3.5 μM in 25 mM HEPES, pH 7.0). After aging, the interfacial elasticity modulus was 5 mN/m and the maximum interfacial stress was 0.3 mN/m. $CaCl_2$ was then added to give a bulk solution concentration of 100 mM. After $Ca^{2+}$ addition and further aging, the interfacial elasticity modulus was 80 mN/m and the maximum interfacial stress was 4.0 mN/m at 13% strain.

Example 25

Enhancement of Force Transmission at the Air-Water Interface by a Peptide Network Formed from Peptides having SEQ ID NO:9 by the Addition of La(III) Ions and Alteration of Force Transmission by Subsequent Addition of EDTA An air-water interface was prepared using peptide having SEQ ID NO:9 (3.5 μM in 25 mM HEPES, pH 7.0). After aging, the interfacial elasticity modulus was 4 mN/m and the maximum interfacial stress was 0.3 mN/m. $LaCl_3$ was then added to give a bulk solution concentration of 10 mM. After $LaCl_3$ addition and further aging, the interfacial elasticity modulus was 1561 mN/m and the maximum interfacial stress was 36.7 mN/m at 294% strain. EDTA was then added to give a bulk solution concentration of 40 mM. After EDTA addition and further aging, the interfacial elasticity modulus was 406 mN/m and the maximum interfacial stress was 17.6 mN/m at 36% strain.

Example 26

Enhancement of Force Transmission at the Air-Water Interface by a Peptide Network Formed from Peptides having SEQ ID NO:9 by the Addition of Polyethyleneimine (PEI)

An air-water interface was prepared using peptide having SEQ ID NO:9 (2.5 μM in 25 mM HEPES, pH 8.0). After aging, the interfacial elasticity modulus was 3 mN/m and the maximum interfacial stress was 0.3 mN/m. Polyethyleneimine (PEI) was then added to give a bulk solution concentration of 0.2% (w/v). After PEI addition and further aging, the interfacial elasticity modulus was 18 mN/m and the maximum interfacial stress was 0.9 mN/m at 21% strain.

Example 27

Enhancement of Force Transmission at the Air-Water Interface by a Peptide Network Formed from Peptides having SEQ ID NO:9 by the Addition of Spermine An air-water interface was prepared using peptide having SEQ ID NO:9 (3.5 μM in mixed 1 mM sodium phosphate, 1 mM sodium citrate, 1 mM sodium borate at pH 7.0). After aging, the interfacial elasticity modulus was 4 mN/m and the maximum interfacial stress was 0.3 mN/m. Spermine was then added to give a bulk solution concentration of 10 mM. After spermine addition and further aging, the interfacial elasticity modulus was 25 mN/m and the maximum interfacial stress was 0.4 mN/m.

Example 28

Enhancement of Force Transmission at the Air-Water Interface by a Peptide Network Formed from Peptides having SEQ ID NO: 10 by the Addition of Mixed Phosphate, Citrate and Borate (PCB) Buffer An air-water interface was prepared using peptide having SEQ ID NO:10 (5.0 μM in 25 mM Tris.HCl, 100 mM NaCl at pH 7.3). After aging, the interfacial elasticity modulus was 29 mN/m and the maximum interfacial stress was 0.5 mN/m. A mixed sodium phosphate, sodium citrate, sodium borate (PCB) buffer at pH 7.0 was then added to give bulk solution concentrations of 1 mM phosphate, 1 mM citrate, and 1 mM borate. After PCB addition and further aging, the interfacial elasticity modulus was 51 mN/m and the maximum interfacial stress was 1.4 mN/m at 39% strain.

Example 29

Enhancement of Force Transmission at the Air-Water Interface by a Peptide Network Formed from Peptides having SEQ ID NO:4 by the Addition of Zn(II) Ions and Abolition of Force Transmission by Subsequent Addition of EDTA An air-water interface was prepared using peptide having SEQ ID NO:4 (5.0 μM in 25 mM Tris.HCl, 100 mM NaCl at pH 8.0). After aging, the interfacial elasticity modulus was 8 mN/m and the maximum interfacial stress was 0.2 mN/m. ZnSO$_4$ was then added to give a bulk solution concentration of 200 µM. After ZnSO$_4$ addition and further aging, the interfacial elasticity modulus was 132 mN/m and the maximum interfacial stress was 6.3 mN/m at 31% strain. EDTA was then added to give a bulk solution concentration of 250 µM. After EDTA addition and further aging, the interfacial elasticity modulus was 8 mN/m and the maximum interfacial stress was 0.3 mN/m.

Example 30

Enhancement of Force Transmission at the Air-Water Interface by a Peptide Network Formed from Peptides having SEQ ID NO:4 by the Addition of La(III) Ions and Abolition of Force Transmission by Subsequent Addition of EDTA An air-water interface was prepared using peptide having SEQ ID NO:4 (5.0 µM in 25 mM Tris.HCl, 100 mM NaCl at pH 8.0). After aging, the interfacial elasticity modulus was 1 mN/m and the maximum interfacial stress was 0.2 mN/m. LaCl$_3$ was then added to give a bulk solution concentration of 1 mM La(III). After LaCl$_3$ addition and further aging, the interfacial elasticity modulus was 165 mN/m and the maximum interfacial stress was 7.2 mN/m at 66% strain. EDTA was then added to give a bulk solution concentration of 2 mM. After EDTA addition and further aging, the interfacial elasticity modulus was 26 mN/m and the maximum interfacial stress was 0.4 mN/m.

Example 31

Enhancement of Force Transmission at the Air-Water Interface by a Peptide Network Formed from Peptides having SEQ ID NO:4 by the Addition of Acid and Disruption of Force Transmission by Neutralization with Base An air-water interface was prepared using peptide having SEQ ID NO:4 (5.0 µM in 25 mM Tris.HCl, 100 mM NaCl at pH 8.0). After aging, the interfacial elasticity modulus was 7 mN/m and the maximum interfacial stress was 0.1 mN/m. HCl was then added to reduce the pH of the solution to 6.0. After HCl addition and further aging, the interfacial elasticity modulus was 244 mN/m and the maximum interfacial stress was 7.9 mN/m at 10% strain. NaOH was then added to restore the pH of the solution to 8.0. After NaOH addition and further aging, the interfacial elasticity modulus was 8 mN/m and the maximum interfacial stress was 0.4 mN/m.

Example 32

Disruption of Force Transmission at the Air-Water Interface by a Peptide Network Formed from Peptides having SEQ ID NO:13 by the Addition of Acid and Restoration of Force Transmission by Neutralization with Base An air-water interface was prepared using peptide having SEQ ID NO:13 (6.0 µM in 25 mM Tris.HCl, 100 mM NaCl at pH 8.0). After aging, the interfacial elasticity modulus was 55 mN/m and the maximum interfacial stress was 2.0 mN/m at 60% strain. HCl was added to reduce the pH of the solution to 6.0. After HCl addition and further aging, the interfacial elasticity modulus was 21 mN/m and the maximum interfacial stress was 0.3 mN/m. NaOH was then added to restore the pH of the solution to 8.0. After NaOH addition and further aging, the interfacial elasticity modulus was 53 mN/m and the maximum interfacial stress was 1.8 mN/m at 21% strain.

Example 33

Enhancement of Force Transmission at the Air-Water Interface by a Peptide Network Formed from Peptides having SEQ ID NO:13 by the Addition of Zn(II) Ions and Reduction in Force Transmission by Subsequent Addition of EDTA An air-water interface was prepared using peptide having SEQ ID NO:13 (6.0 µM in 25 mM Tris.HCl, 100 mM NaCl at pH 7.3). After aging, the interfacial elasticity modulus was 62 mN/m and the maximum interfacial stress was 2.5 mN/m at 46% strain. ZnSO$_4$ was then added to give a solution concentration of 200 µM. After ZnSO$_4$ addition and further aging, the interfacial elasticity modulus was 677 mN/m and the maximum interfacial stress was 24.4 mN/m at 161% strain. EDTA was then added to give a solution concentration of 1 mM. After EDTA addition and further aging, the interfacial elasticity modulus was 49 mN/m and the maximum interfacial stress was 1.3 mN/m at 22% strain.

Example 34

Disruption of Ni(II)-Enhanced Force Transmission at the Air-Water Interface by a Peptide Network Formed from Peptides having SEQ ID NO:13 by the Addition of Acid, Restoration of Force Transmission by Subsequent Neutralization with Base, and Further Enhancement of Force Transmission by Addition of Excess Base to Raise the pH above the Initial Value An air-water interface was prepared using peptide having SEQ ID NO:13 (6.0 µM in 25 mM MES at pH 6.0 containing 200 M Ni(NO$_3$)$_2$). After aging, the interfacial elasticity modulus was 179 mN/m and the maximum interfacial stress of 11.1 mN/m at 61% strain. HCl was then added to reduce the solution pH to 3.0. After HCl addition and further aging, the interfacial elasticity modulus was 10 mN/m and the maximum interfacial stress was 0.2 mN/m. NaOH was then added to restore the solution pH to 6.0. After NaOH addition and further aging, the interfacial elasticity modulus was 191 mN/m and the maximum interfacial stress was 13.3 mN/m at 93% strain. NaOH was then added to further increase the solution pH to 8.0). After NaOH addition and further aging, the interfacial elasticity modulus was 589 mN/m and the maximum interfacial stress was 21.0 mN/m at 121% strain.

Example 35

Effect of Changes in pH on Force Transmission at the Air-Water Interface by a Peptide Network Formed from Peptides having SEQ ID NO:6

An air-water interface was prepared using peptide having SEQ ID NO:6 (18 µM in 25 mM MES at pH 6.0). After aging, the interfacial elasticity modulus was 355 mN/m and the maximum interfacial stress was 14.6 mN/m at 109% strain. HCl was then added to reduce the solution pH to 3. After HCl addition and further aging, the interfacial elasticity modulus was 119 mN/m and the maximum interfacial stress was 6.1 mN/m at 38% strain. NaOH was then added to restore the solution pH to 6. After NaOH addition and further aging, the interfacial elasticity modulus was 315 mN/m and the maximum interfacial stress was 14.3 mN/m at 204% strain.

Example 36

Effect of Added NaOH, HCl, Zn(II) and EDTA on the Stability of Foams Prepared from a Solution of Peptide having SEQ ID NO:2

A foam was prepared as described above using peptide having SEQ ID NO:2 (0.3 mg/mL in 25 mM HEPES pH 7.4). Foam collapse was slow, with a significant volume of foam still remaining at 10 minutes after foam formation. $ZnSO_4$ was then added to give a bulk solution concentration of 400 µM. A new foam prepared from the peptide solution after $ZnSO_4$ addition showed enhanced stability, with the height of the foam only slightly reduced at 20 minutes after foam formation. $H_2SO_4$ was then added to reduce the solution pH to 3.6, leading to collapse of the foam within 30 seconds. A new foam prepared from the peptide solution adjusted to pH 3.6 collapsed completely within 2 minutes after foam formation. NaOH was then added to restore the solution pH to 7.4. A new foam prepared from the peptide solution adjusted to pH 7.4 showed good stability, with the height of the foam column only slightly reduced at 10 minutes after foam formation. EDTA was then added to give a bulk solution concentration of 0.5 mM, leading to foam collapse within 60 seconds. A new foam prepared from the peptide solution after EDTA addition collapsed almost completely within 60 seconds. $ZnSO_4$ was then added to give a total bulk solution concentration of 800 µM, taking into account the amount previously added. A new foam prepared from the peptide solution after further $ZnSO_4$ addition showed enhanced stability, with very little collapse evident after 10 minutes.

Example 37

Effect of added NaOH, HCl, La(III) and EDTA on the Stability of Foams Prepared from a Solution of Peptide having SEQ ID NO:9

A foam was prepared using peptide having SEQ ID NO:9 (0.3 mg/mL in 1 mM sodium phosphate, 1 mM sodium citrate, 1 mM sodium borate buffer, pH 3.0). Slow collapse of the foam was observed where at 120 seconds, only limited thinning of the foam had occurred.

NaOH was then added to the foam column to bring the bulk solution pH to 7.0, causing foam collapse within 30 seconds. New foam prepared from the peptide solution to pH 7.0 showed essentially complete collapse after 30 seconds.

$LaCl_3$ was then added to the collapsed foam to give a bulk solution concentration of 10 mM. A new foam was prepared from the peptide solution. In the presence of added La(III) the foam collapsed extremely slowly with significant foam height still present after 1 h.

HCl was then added to the remaining foam to restore the solution pH to 3.0, causing foam collapse over 15 mM. A new foam prepared from the peptide solution at pH 3 collapsed slowly where foam collapse was not complete after 120 seconds.

Example 38

Effect of Added NaOH, HCl, Ni(II) and EDTA on the Stability of Foams Prepared from a Solution of Peptide having SEQ ID NO:10

A foam was prepared using peptide having SEQ ID NO:10 (0.3 mg/mL in 1 mM sodium phosphate, 1 mM sodium citrate, 1 mM sodium borate buffer, pH 6.0). Foam collapse was essentially complete after 60 seconds.

NaOH was then added to bring the solution pH to 11.0. A new foam prepared from the peptide solution at pH 11.0 showed slow collapse which was essentially complete after 15 min.

$Ni(NO_3)_2$ was then added to give a Ni(II) concentration of 280 µM. A new foam prepared from the peptide solution in the presence of $Ni(NO_3)_2$ showed foam collapse was essentially complete after 120 seconds.

HCl was then added to restore the solution pH to 6.0. A new foam prepared from the peptide solution adjusted to pH 6.0 showed essentially complete collapse after 60 seconds.

NaOH was then added to again bring the solution pH to 11.0. A new foam prepared from the peptide solution adjusted to pH 11.0 was more stable than previous foams formed at either pH 6 or pH 11 in the presence of Ni(II), possibly reflecting the effects of additional salt from pH titrations.

EDTA was then added to give a final concentration of 1.4 mM. A new foam prepared from the peptide solution with EDTA showed essentially complete collapse after 30 seconds.

Example 39

Effect of Added NaOH, HCl, La(III) and EDTA on the Stability of Foams Prepared from a Solution of Peptide having SEQ ID NO:4

A foam was prepared using peptide having SEQ ID NO:4 (0.3 mg/mL in 1 mM sodium phosphate, 1 mM sodium citrate, 1 mM sodium borate buffer, pH 3.0). Foam collapse was slow.

NaOH was then added to the foam column to bring the solution pH to 7.0, causing foam collapse within 90 seconds. A new foam prepared from the peptide solution at pH 7.0 showed essentially complete collapse after 90 seconds.

$LaCl_3$ was then added to give a bulk solution La(III) concentration of 250 µM. A new foam prepared from the peptide solution in the presence of La(III) showed significantly slower collapse than in the absence of added La(III).

HCl was then added to the remaining foam to restore the solution pH to 3.0. A new foam prepared from the peptide solution adjusted to pH 3.0 showed more rapid collapse than at pH 3 in the absence of La(III).

NaOH was then added to again bring the solution pH to 7.0. A new foam prepared from the peptide solution adjusted to pH 7 was moderately stable.

EDTA was then added to give a bulk solution concentration of 2.5 mM, leading to rapid foam collapse within 60 seconds. A new foam prepared from the peptide solution showed only slow collapse which may reflect inefficient binding of La(III) by this chelating agent at the pH of the experiment.

Example 40

Effect of Added NaOH, HCl, Ni(II) and EDTA on the Stability of Foams Prepared from a Solution of Peptide having SEQ ID NO:13

A foam was prepared using peptide having SEQ ID NO:13 (0.3 mg/mL in 25 mM MES pH 6.0). Foam collapse was essentially complete after 60 seconds.

NaOH was then added to bring the solution pH to 8.0. A new foam prepared from the peptide solution adjusted to pH 8 showed essentially complete collapse after 90 seconds.

Ni(NO$_3$)$_2$ was then added to give a bulk solution concentration of 500 µM. A new foam prepared from the peptide solution in the presence of Ni(NO$_3$)$_2$ showed significantly slower foam collapse than in the absence of added Ni(II).

HCl was then added to restore the solution pH to 6.0 causing rapid foam collapse within 30 seconds. A new foam prepared from peptide solution adjusted to pH 6.0 showed essentially complete collapse after 120 seconds.

NaOH was then added to bring the solution pH to 8.0. A new foam prepared from the peptide solution adjusted to pH 8.0 showed significantly slower collapse than at pH 6.0.

EDTA was then added to the remaining foam to give a final concentration of 2.5 mM, causing rapid foam collapse within 60 seconds. A new foam prepared from the peptide solution in the presence of EDTA showed essentially complete collapse after 30 seconds.

Example 41

Effect of Added NaOH. HCl, Ni(II) and EDTA on the Stability of Foams Prepared from a Solution of Peptide having SEQ ID NO:6

A foam was prepared using peptide having SEQ ID NO:6 (0.3 mg/mL in 25 mM MES pH 6.0). Foam collapse was essentially complete after 60 seconds.

NaOH was then added to bring the solution pH to 8.0. A new foam prepared from the peptide solution adjusted to pH 8.0 was slightly more stable but still showed essentially complete collapse after 120 seconds.

Ni(NO$_3$)$_2$ was then added to give a bulk solution concentration of 500 µM. A new foam prepared from the peptide solution after Ni(NO$_3$)$_2$ addition showed significantly slower collapse with very little reduction in the height of the foam column at 120 seconds.

HCl was then added to restore the solution pH to 6.0. Addition of HCl caused foam collapse. A new foam prepared from the peptide solution adjusted to pH 6.0 showed essentially complete collapse after 60 seconds, similar to foam prepared at pH 6 in the absence of Ni(II).

NaOH was then added to bring the solution pH to 8.0. A new foam prepared from the peptide solution adjusted to pH 8.0 showed slow collapse, with very little reduction in the height of the foam column at 120 seconds.

EDTA was then added to give a bulk solution concentration of 2.5 mM. Addition of EDTA caused rapid foam collapse within 30 s. A new foam prepared from the peptide solution after EDTA addition showed essentially complete collapse after 60 seconds.

Example 42

Effect of Added NaOH, HCl, Ni(II) and EDTA on the Stability of Foams Prepared from a Solution of Peptide having SEQ ID NO:7

A foam was prepared using peptide having SEQ ID NO:7 (0.3 mg/mL in 25 mM MES pH 6.0). Foam collapse was essentially complete after 60 seconds.

NaOH was then added to bring the solution pH to 8.0. A new foam prepared from the peptide solution adjusted to pH 8 was unstable, with foam collapse essentially complete after 60 seconds.

Ni(NO$_3$)$_2$ was then added to give a bulk solution concentration of 500 µM. A new foam prepared from the peptide solution after Ni(NO$_3$)$_2$ addition showed significantly slower collapse, with very little reduction in the height of the foam column at 120 seconds.

HCl was then added to the remaining foam to restore the solution pH to 6.0. Addition of HCl caused rapid foam collapse within 60 s. A new foam prepared from the peptide solution adjusted to pH 6.0 showed good stability with foam collapse near complete only after 15 min.

NaOH was then added to bring the solution pH to 8.0. A new foam prepared from the peptide solution adjusted to pH 8.0 showed good stability, with foam collapse near complete only after 20 mM.

EDTA was then added to give a bulk solution concentration of 2.5 mM. A new foam prepared from the peptide solution after EDTA addition showed essentially complete collapse after 60 seconds.

Example 43

Effect of Added NaOH, HCl, Ni(II) and EDTA on the Stability of Foams Prepared from a Solution of Peptide having SEQ ID NO:8

A foam was prepared using peptide having SEQ ID NO:8 (0.3 mg/mL in 25 mM MES pH 6.0). Foam collapse was complete only after 30 mM.

NaOH was then added to bring the solution pH to 8.0. A new foam prepared from the peptide solution adjusted to pH 8.0 was unstable, with foam collapse essentially complete after 60 seconds.

Ni(NO$_3$)$_2$ was then added to give a bulk solution concentration of 500 µM. A new foam prepared from the peptide solution after Ni(NO$_3$)$_2$ addition showed significantly slower collapse, with very little reduction in the height of the foam column at 120 seconds.

HCl was then added to restore the solution pH to 6.0. Addition of HCl caused foam collapse. A new foam prepared from the peptide solution adjusted to pH 6.0 showed good stability, with foam collapse near complete only after 8 mM.

NaOH was then added to bring the solution pH to 8.0. A new foam prepared from the peptide solution adjusted to pH 8.0 showed good stability, with very little reduction in the height of the foam column at 120 seconds.

EDTA was then added to give a bulk solution concentration of 2.5 mM. Addition of EDTA caused foam collapse. A new foam prepared from the peptide solution after EDTA addition showed essentially complete collapse after 15 seconds.

Example 44

Effect of Added NaOH, HCl, Ni(II) and EDTA on the Stability of Foams Prepared from a Solution of Peptide having SEQ ID NO:11

A foam was prepared using peptide having SEQ ID NO:11 (0.3 mg/mL in 25 mM MES pH 6.0). Foam collapse was essentially complete after 60 seconds.

NaOH was then added to bring the solution pH to 8.0. A new foam prepared from the peptide solution adjusted to pH 8.0 was unstable, with essentially complete collapse after 60 seconds.

Ni(NO$_3$)$_2$ was then added to give a bulk solution concentration of 500 µM. A new foam prepared from the peptide solution after Ni(NO$_3$)$_2$ addition showed essentially complete collapse after 120 seconds.

HCl was then added to restore the solution pH to 6.0. A new foam prepared from the peptide solution adjusted to pH 6.0 showed essentially complete collapse after 60 seconds.

NaOH was then added to bring the solution pH to 8.0. A new foam prepared from the peptide solution adjusted to pH 8.0 showed essentially complete collapse after 120 seconds.

EDTA was then added to give a bulk solution concentration of 2.5 mM. A new foam prepared from the peptide solution after EDTA addition showed essentially complete collapse after 20 seconds.

Example 45

Effect of Added NaOH, HCl, Ni(II) and EDTA on the Stability of Foams Prepared from a Solution of Peptide having SEQ ID NO:12

A foam was prepared using peptide having SEQ ID NO:12 (0.3 mg/mL in 25 mM MES pH 6.0). Foam collapse was complete after 30 seconds.

NaOH was then added to bring the solution pH to 8.0. A new foam prepared from the peptide solution adjusted to pH 8.0 was unstable, with essentially complete collapse after 10 seconds.

Ni(NO$_3$)$_2$ was then added to give a bulk solution concentration of 500 µM. A new foam prepared from the peptide solution after Ni(NO$_3$)$_2$ addition showed essentially complete collapse after 10 seconds.

HCl was then added to restore the solution pH to 6.0. A new foam prepared from the peptide solution adjusted to pH 6.0 was significantly more stable than before addition of HCl, with foam collapse only complete after 10 min.

NaOH was then added to bring the solution pH to 8.0. A new foam prepared from the peptide solution adjusted to pH 8.0 showed relatively slow collapse.

EDTA was then added to give a bulk solution concentration of 2.5 mM. A new foam prepared from the peptide solution after EDTA addition showed rapid collapse.

Example 46

Effect of Acidification on Crude Oil Emulsifying Properties of a Peptide Network Containing Zinc(II) Ions and Peptides having SEQ ID NO:2

An oil-in-water emulsion was prepared using peptide having SEQ ID NO:2 (147 µM in 25 mM HEPES, pH 7.4 containing 400 µM ZnSO$_4$) and Rang Dong crude oil previously liquefied by mild heat treatment (20% volume fraction). Aliquots (1 mL) of the emulsions were transferred into 4 mL glass vials under magnetic stirring. A control vial was used to demonstrate stability of the emulsion during the test period. When an aliquot (10 µL) of 1.9 M H$_2$SO$_4$ was added to 1 mL of emulsion with stirring, the emulsion rapidly coalesced, with gross phase separation occurring in a matter of seconds after addition. The aqueous phase continued to clear over several minutes after H$_2$SO$_4$ addition. No separation was observed in the control vial.

Example 47

Effect of EDTA Addition on Crude Oil Emulsifying Properties of a Peptide Network Containing Zinc(II) Ions and Peptides having SEQ ID NO:2

An oil-in-water emulsion was prepared and divided as for Example 46. When an aliquot (20 µL) of 100 mM EDTA was added to 1 mL of emulsion with stirring, the emulsion rapidly coalesced, with gross phase separation occurring in a matter of seconds after addition. The aqueous phase continued to clear over several minutes after EDTA addition. No separation was observed in the control vial.

Example 48

Biocatalysis in Toluene Emulsions Stabilized by a Peptide Network Containing Zn(II) ions and Peptides having SEQ ID NO:2

To demonstrate the utility of peptide-stabilized emulsions in increasing the productivity of biocatalytic reactions on poorly water-soluble substrates, a series of biocatalysis reactions were carried out using a commercial immobilized lipase (Lipolase) and the lipase substrate methyl mandelate. The substrate was present initially in the oil phase of a toluene-in-water emulsion stabilized by peptides having SEQ ID NO:2 in the presence of Zn(II) ions. For comparison, the same reaction was carried out in water in the presence of a water-miscible organic cosolvent at the same total substrate concentration. In this case, the water-miscible organic solvent chosen was acetonitrile. Addition of water-miscible organic cosolvents (such as acetone, acetonitrile, or C1-C4 alcohols) to increase the solubility of a poorly water-soluble substrate is a method that has been frequently used to increase the productivity of biocatalytic reactions. However, the addition of water-miscible organic cosolvents at concentrations above approximately 20% (v/v) often leads to enzyme inactivation, thus limiting the extent to which hydrophobic substrates can be solubilized.

A series of oil-in-water emulsions were prepared using peptide having SEQ ID NO:2 (228-410 µM in 25 mM Tris.HCl, 100 mM NaCl at pH 8.0 containing 0.49-0.89 mM ZnSO$_4$) and a 1 M solution of methyl mandelate in toluene (10-50% volume fraction giving methyl mandelate concentrations of 100-500 mM in the emulsion). The total amounts of peptide and zinc in the emulsion were equal in each case. To carry out the biocatalysis reaction aliquots (1 mL) of each emulsion were transferred into a 4 mL glass vial containing 5 mg Lipolase. (Lipase acrylic resin containing immobilized *Candida antarctica*, lipase B) and shaken at 37° C. Samples were taken at intervals for analysis by HPLC to determine the extent of the reaction.

For comparison, a series of biocatalysis reactions were carried out in 10-50% (v/v) acetonitrile with the same buffer, enzyme and substrate composition. For example, an aliquot (0.4 mL) of 25 mM Tris.HCl, 100 mM NaCl at pH 8.0 was mixed with 0.5 mL MilliQ H$_2$O and 0.1 mL 1 M methyl mandelate in acetonitrile and 5 mg Lipolase was added to give a reaction medium containing 10% (v/v) acetonitrile. Reactions were then conducted and analysed as for the peptide-containing emulsions.

The results showed higher levels of hydrolysis of methyl mandelate in the peptide-containing emulsions than in the acetonitrile media for all solvent concentrations. For a solvent volume fraction of 10%, at 4 hours, the concentration of the product mandelic acid in the toluene-in-water emulsion was 61.4 mM or 39% higher than the product concentration obtained in the reaction using acetonitrile as cosolvent (44.2 mM). For a solvent fraction of 20%, at 4.5 hours, the concentration of the product mandelic acid in the toluene-in-water emulsion was 129 mM or 2.5-fold higher than the product concentration obtained in the reaction using acetonitrile as cosolvent (51.0 mM). For a solvent volume fraction of 30%, at 4 hours, the concentration of the product mandelic acid in the toluene-in-water emulsion was 143 mM or 5.3-fold higher than the product concentration obtained in the reaction using acetonitrile as cosolvent (26.9 mM). Finally, for a solvent volume fraction of 50%, at 3 hours, the concentration of the product mandelic acid in the toluene-in-water emulsion was 139 mM or 10-fold higher than the product concentration obtained in the reaction using acetonitrile as cosolvent (13.9 mM).

It can be seen that the relative productivity advantage of the peptide-stabilized toluene-in-water emulsion over the acetonitrile cosolvent system increases with the volume fraction of solvent (toluene or acetonitrile). While biocatalytic productivity in the toluene-in-water emulsion did not increase significantly above a toluene volume fraction of 20-30%, biocatalytic productivity in the acetonitrile reaction medium fell significantly above this volume fraction, presumably due to enzyme inactivation. The ability to efficiently convert a poorly water-soluble substrate at higher concentrations, amounting to a higher volumetric productivity, is a significant advantage of the peptide-containing emulsion as a reaction medium.

Example 49

Effect of Changes in pH on Force Transmission at the Air-Water Interface by a Peptide Network Formed from Peptides having SEQ ID NO:6

An air-water interface was prepared using peptide having SEQ ID NO:6 (5 µM in 10 mM NaOH, pH 12). After aging, the interfacial elasticity modulus was 515 mN/m and the maximum interfacial stress was 21.5 mN/m at 43% strain. HCl was then added to reduce the solution pH to below 2. After HCl addition and further aging, the interfacial elasticity modulus was 17 mN/m and the maximum interfacial stress was 0.7 mN/m. NaOH was then added to restore the bulk solution pH to 12. After NaOH addition and further aging, the interfacial elasticity modulus was 425 mN/m and the maximum interfacial stress was 19.2 mN/m at 47% strain.

Example 50

Effect of Metal Ion Sequestration on Force Transmission at the Air-Water Interface by a Peptide Network Formed from Peptides having SEQ ID NO:6

An air-water interface was prepared using peptide having SEQ ID NO:6 (18 µM in 25 mM Tris.HCl, 100 mM NaCl, pH 8.0 containing 200 µM Ni(NO$_3$)$_2$). After aging, the interfacial elasticity modulus was 516 mN/m and the maximum interfacial stress was 15.4 mN/m at 92% strain. EDTA was then added to give a bulk solution concentration of 1 mM. After EDTA addition and further aging, the interfacial elasticity modulus was 282 mN/m and the maximum interfacial stress was 11.1 mN/m at 103% strain.

Example 51

Effect of pH and Metal Ion Addition on the Rate of Network Formation at the Air-Water Interface by a Peptide Network Formed from Peptides having SEQ ID NO:6

A series of air-water interfaces were prepared using peptide having SEQ ID NO:6 (5 µM in 25 mM MES pH 6.0 or 25 mM HEPES pH 8.0 in the presence or absence of 200 µM Ni(NO$_3$)$_2$. Measurements of interfacial elasticity modulus were made every 5 seconds after interface preparation, by repeated tension-compression cycles to 5% strain. The most rapid network formation was observed for peptide having SEQ ID NO:6 in 25 mM HEPES pH 8.0 in the presence of 200 µM Ni(NO$_3$)$_2$, with an interfacial elasticity of modulus of 193 mN/m at 100 seconds. At 100 seconds, the interfacial elasticity modulus was 83 mN/m for peptide having SEQ ID NO:6 in 25 mM HEPES pH 8.0 in the absence of added metal ions. At 100 seconds, the interfacial elasticity modulus was 55 mN/m for peptide having SEQ ID NO:6 in 25 mM MES pH 6.0 in the presence of 200 µM Ni(NO$_3$)$_2$. At 100 seconds, the interfacial elasticity modulus was 45 mN/m for peptide having SEQ ID NO:6 in 25 mM MES pH 6.0 in the absence of added metal ions. At longer times (300 seconds), network strengths achieved were similar at either pH for peptide having SEQ ID NO:6 in the absence of added metal ions (interfacial elasticity modulus 112 mN/m in 25 mM MES pH 6.0; interfacial elasticity modulus 130 mN/m in 25 mM HEPES pH 8.0). Also at longer times (300 seconds), network strengths achieved were similar at either pH for peptide having SEQ ID NO:6 in the presence of 200 µM Ni(NO$_3$)$_2$ (interfacial elasticity modulus 221 mN/m in 25 mM MES pH 6.0; interfacial elasticity modulus 232 mN/m in 25 mM HEPES pH 8.0).

Example 52

Effect of pH and Metal Ion Addition on the Rate of Network Formation at the Air-Water Interface by a Peptide Network Formed from Peptides having SEQ ID NO:7

A series of air-water interfaces were prepared using peptide having SEQ ID NO:7 (5 µM in 25 mM MES pH 6.0 or 25 mM HEPES pH 8.0 in the presence or absence of 200 µM Ni(NO$_3$)$_2$. Measurements of interfacial elasticity modulus were made every 5 seconds after interface preparation, by repeated tension-compression cycles to 5% strain. The most rapid network formation was observed for peptide having SEQ ID NO:7 in 25 mM HEPES pH 8.0 in the presence of 200 µM Ni(NO$_3$)$_2$, with an interfacial elasticity of modulus of 414 mN/m at 30 seconds. At 30 seconds, the interfacial elasticity modulus was 67 mN/m for peptide having SEQ ID NO:6 in 25 mM HEPES pH 8.0 in the absence of added metal ions. At 30 seconds, the interfacial elasticity modulus was 78 mN/m for peptide having SEQ ID NO:6 in 25 mM MES pH 6.0 in the presence of 200 µM Ni(NO$_3$)$_2$. At 30 seconds, the interfacial elasticity modulus was 11 mN/m for peptide having SEQ ID NO:6 in 25 mM MES pH 6.0 in the absence of added metal ions. At longer times (300 seconds), network strengths achieved were similar at either pH for peptide having SEQ ID NO:7 in the absence of added metal ions (interfacial elasticity modulus 315 mN/m in 25 mM MES pH 6.0; interfacial elasticity modulus 308 mN/m in 25 mM HEPES pH 8.0). Also at longer times (300 seconds), network strengths achieved were similar at either pH for peptide having SEQ ID NO:7 in the presence of 200 µM Ni(NO$_3$)$_2$ (interfacial elasticity modulus 536 mN/m in 25 mM MES pH 6.0; interfacial elasticity modulus 483 mN/m in 25 mM HEPES pH 8.0).

Example 53

Effect of Changes in pH on Force Transmission at the Air-Water Interface by a Peptide Network Formed from Peptides having SEQ ID NO:11

An air-water interface was prepared using peptide having SEQ ID NO:11 (5 µM in 10 mM HCl, pH 2). After aging, the interfacial elasticity modulus was 1 mN/m and the maximum interfacial stress was 0.2 mN/m. NaOH was then added to neutralize the bulk solution. After NaOH addition and further aging, the interfacial elasticity modulus was 774 mN/m and the maximum interfacial stress was 18.5 mN/m at 44% strain. HCl was then added to restore the solution pH to 2. After HCl addition and further aging, the interfacial elasticity modulus was 11 mN/m and the maximum interfacial stress was 0.3 mN/m.

Example 54

Effect of Changes in pH on Force Transmission at the Air-Water Interface by a Peptide Network Formed from Peptides having SEQ ID NO:12

An air-water interface was prepared using peptide having SEQ ID NO:12 (5 µM in 10 mM HCl, pH 2). After aging, the interfacial elasticity modulus was 1 mN/m and the maximum interfacial stress was 0.2 mN/m. NaOH was then added to neutralize the bulk solution. After NaOH addition and further aging, the interfacial elasticity modulus was 475 mN/m and the maximum interfacial stress was 14.7 mN/m at 23% strain. HCl was then added to restore the solution pH to 2. After HCl addition and further aging, the interfacial elasticity modulus was 6 mN/m and the maximum interfacial stress was 0.3 mN/m.

Example 55

Effect of Changes in pH on Force Transmission at the Air-Water Interface by a Peptide Network Formed from Peptides having SEQ ID NO:8

An air-water interface was prepared using peptide having SEQ ID NO:8 (5 µM in 10 mM HCl, pH 2). After aging, the interfacial elasticity modulus was 176 mN/m and the maximum interfacial stress was 10.2 mN/m at 29% strain. NaOH was then added to increase the bulk solution pH to approximately 10. After NaOH addition and further aging, the interfacial elasticity modulus was 102 mN/m and the maximum interfacial stress was 7.4 mN/m at 294% strain. HCl was then added to restore the solution pH to 2. After HCl addition and further aging, the interfacial elasticity modulus was 81 mN/m and the maximum interfacial stress was 7.3 mN/m at 268% strain.

Example 56

Effect of Changes in pH on Force Transmission at the Air-Water Interface by a Peptide Network Formed from Peptides having SEQ ID NO:7

An air-water interface was prepared using peptide having SEQ ID NO:7 (5 µM in 10 mM HCl, pH 2). After aging, the interfacial elasticity modulus was 76 mN/m and the maximum interfacial stress was 4.5 mN/m at 34% strain. NaOH was then added to increase the bulk solution pH to approximately 7. After NaOH addition and further aging, the interfacial elasticity modulus was 115 mN/m and the maximum interfacial stress was 6.5 mN/m at 57% strain.

Example 57

Effect of the Anionic Detergent SDS on Force Transmission at the Air-Water Interface by a Peptide Network Formed from Peptides having SEQ ID NO:2

An air-water interface was prepared using the negatively charged detergent sodium dodecyl sulfate (SDS, 0.05 mg/mL in 25 mM HEPES, pH 7.4). After aging, the interfacial elasticity modulus was 5 mN/m and the maximum interfacial stress was 0.2 mN/m. Peptide having SEQ ID NO:2 was then added to give a bulk solution concentration of 20 µM. After addition of peptide having SEQ ID NO:2 and further aging, the interfacial elasticity modulus was 33 mN/m and the maximum interfacial stress was 1.4 mN/m at 28% strain. For comparison, an air-water interface was prepared using peptide having SEQ ID NO:2 (20 µM in 25 mM HEPES, pH 7.4) in the absence of added surfactants. After aging, the interfacial elasticity modulus was 8 mN/m and the maximum interfacial stress was 0.4 mN/m.

Example 58

Effect of EDTA or Acidification on Emulsifying Properties of a Peptide Network Containing Nickel(II) Ions and Peptides having SEQ ID NO:6

An oil-in-water emulsion was prepared using peptide having SEQ ID NO:6 (97 µM in 25 mM HEPES, pH 8 containing 200 µM $Ni(NO_3)_2$) and toluene (20% volume fraction). The EAI was 307 $m^2 g^{-1}$. For enhanced visual observation of emulsion switching, a second oil-in-water emulsion was prepared containing 10 µM methylene blue in the aqueous phase and 50 µM Sudan III in the oil phase. The emulsion was stable to phase coalescence over at least 1 h at room temperature. However, when EDTA was added with stirring to give a concentration of 1 mM, phase coalescence was visible within 30 seconds. Similarly, when $H_2SO_4$ was added with stirring to give a concentration of 16 mM, phase coalescence was visible within 10 seconds.

Example 59

Effect of Acidification on Emulsifying Properties of a Peptide Network Containing Nickel(II) Ions and Peptides having SEQ ID NO:7

An oil-in-water emulsion was prepared using peptide having SEQ ID NO:7 (100 µM in 25 mM MES, pH 6 containing 200 µM $Ni(NO_3)_2$) and toluene (20% volume fraction). The EAI was 165 $m^2 g^{-1}$. The emulsion was stable to phase coalescence over at least 1 h at room temperature. However, when $H_2SO_4$ was added with stirring to give a concentration of 16 mM, phase coalescence was visible after 5 minutes.

Example 60

Effect of EDTA or Acidification on Emulsifying Properties of a Peptide Network Containing Nickel(II) Ions and Peptides having SEQ ID NO:8

An oil-in-water emulsion was prepared using peptide having SEQ ID NO:8 (100 µM in 25 mM HEPES, pH 8 containing 200 µM $Ni(NO_3)_2$) and toluene (20% volume fraction). The EAI was 224 $m^2 g^{-1}$. For enhanced visual observation of emulsion switching, a second oil-in-water emulsion was prepared containing 10 µM methylene blue in the aqueous phase and 50 µM Sudan III in the oil phase. The emulsion was stable to phase coalescence over at least 1 h at room temperature. However, when EDTA was added with stirring to give a concentration of 1 mM, phase coalescence was visible within 10 seconds. Similarly, when $H_2SO_4$ was added with stirring to give a concentration of 16 mM, phase coalescence was visible within 10 seconds.

Example 61

Effect of Acidification on Emulsifying Properties of a Peptide Network Containing Nickel(II) Ions and Peptides having SEQ ID NO:11

An oil-in-water emulsion was prepared using peptide having SEQ ID NO:11 (97 µM in 25 mM HEPES, pH 8 containing 200 µM Ni(NO$_3$)$_2$) and toluene (20% volume fraction). The EAI was 107 m$^2$ g$^{-1}$. For enhanced visual observation of emulsion switching, a second oil-in-water emulsion was prepared containing 10 µM methylene blue in the aqueous phase and 50 µM Sudan III in the oil phase. The emulsion was stable to phase coalescence over at least 1 h at room temperature. However, when H$_2$SO$_4$ was added with stirring to give a concentration of 16 mM, phase coalescence was visible within 10 seconds.

Example 62

Effect of EDTA or Acidification on Emulsifying Properties of a Peptide Network Containing Nickel(II) Ions and Peptides having SEQ ID NO:12

An oil-in-water emulsion was prepared using peptide having SEQ ID NO:12 (97 µM in 25 mM HEPES, pH 8 containing 200 µM Ni(NO$_3$)$_2$) and toluene (20% volume fraction). The EAI was 92 m$^2$ g$^{-1}$. The emulsion was stable to phase coalescence over at least 1 h at room temperature. However, when EDTA was added with stirring to give a concentration of 1 mM, phase coalescence was visible within 10 seconds. Similarly, an oil-in-water emulsion was prepared using peptide having SEQ ID NO:12 (97 µM in 25 mM MES, pH 6 containing 200 µM Ni(NO$_3$)$_2$) and toluene (20% volume fraction). The EAI was 160 m$^2$ g$^{-1}$. For enhanced visual observation of emulsion switching, a second oil-in-water emulsion was prepared containing 10 µM methylene blue in the aqueous phase and 50 µM Sudan III in the oil phase. The emulsion was stable to phase coalescence over at least 1 h at room temperature. However, when H$_2$SO$_4$ was added with stirring to give a concentration of 16 mM, phase coalescence was visible within 30 seconds.

Example 63

Effect of Acidification on Emulsifying Properties of a Peptide Network Containing Nickel(II) Ions and Peptides having SEQ ID NO:13

An oil-in-water emulsion was prepared using peptide having SEQ ID NO:13 (100 µM in 25 mM HEPES, pH 8 containing 200 µM Ni(NO$_3$)$_2$) and toluene (20% volume fraction). The EAI was 80 m$^2$ g$^{-1}$. The emulsion was stable to phase coalescence over at least 1 h at room temperature. However, when H$_2$SO$_4$ was added with stirring to give a concentration of 16 mM, phase coalescence was visible after 60 seconds.

Example 64

Effect of Changes in pH on the Stability of Foams Prepared from a Solution of Peptide having SEQ ID NO:9 and Peptide having SEQ ID NO:10

A foam was prepared using peptide having SEQ ID NO:9 (0.15 mg/mL in 1 mM sodium phosphate, 1 mM sodium citrate, 1 mM sodium borate buffer, pH 3.0) and peptide having SEQ ID NO:10 (0.15 mg/mL in 1 mM sodium phosphate, 1 mM sodium citrate, 1 mM sodium borate buffer, pH 3.0). Foam collapse was essentially complete after 120 seconds. NaOH was then added to bring the solution pH to approximately 12. A new foam prepared from the peptide solution adjusted to pH 12 showed enhanced stability, with foam collapse not complete after 10 minutes. HCl was then added to bring the solution pH to 7.0. A new foam prepared from the peptide solution adjusted to pH 7 showed essentially complete collapse after 120 seconds.

Example 65

Biocatalysis in Toluene Emulsions Stabilized by a Peptide Network Containing Zn(II) Ions and Peptides having SEQ ID NO:2

To further demonstrate the utility of peptide-stabilized emulsions in increasing the productivity of biocatalytic reactions on poorly water-soluble substrates, a series of biocatalysis reactions were carried out using a soluble lipase (*Candida rugosa* lipase) and the lipase substrate methyl mandelate. Oil-in-water emulsions were prepared using peptide having SEQ ID NO:2 (final composition: 122 µM in 17 mM HEPES pH 7.0 containing 280 µM ZnSO$_4$ and 5.5 mg/mL partly purified *Candida rugosa* lipase) and a 1 M solution of either (R)- or (S)-methyl mandelate in toluene (final composition: 10% volume fraction, giving a concentration of (R)- or (S)-methyl mandelate of 100 mM in the emulsion). To carry out the biocatalysis, aliquots (1 mL) of each emulsion were transferred into a 4 mL glass vial and shaken at 37° C. Samples were taken at intervals for analysis by high performance liquid chromatography to determine the extent of reaction. For comparison, biocatalysis reactions were carried out in 10% (v/v) acetonitrile with the same buffer, enzyme and substrate composition. Reactions were then conducted and analyzed as for the peptide-containing emulsions.

The results showed a higher rate of hydrolysis of both (R)- and (S)-methyl mandelate in the peptide-containing emulsions than in the acetonitrile reaction medium. For (S)-methyl mandelate, the reaction productivity was 0.49 grams of methyl mandelate hydrolyzed per gram of enzyme per hour in the peptide-containing emulsion, but only 0.11 grams of methyl mandelate hydrolyzed per gram of enzyme per hour in the acetonitrile reaction medium. In addition, the selectivity of the enzyme reaction, expressed as the ratio of (S)-methyl mandelate hydrolysis rates to (R)-methyl mandelate hydrolysis rate, was higher in the peptide-containing emulsion, having a ratio of 27 for the peptide-containing emulsion but only 12 for the acetonitrile reaction medium, suggesting that the presence of acetonitrile rather than toluene as a cosolvent may have a deleterious effect on the enzyme selectivity as well as the enzyme activity.

Example 66

Effect of Admixture of Peptide having SEQ ID NO:2 and the Anionic Detergent SDS on the Stability of a Foam A foam was prepared using peptide having SEQ ID NO:2 (0.05 mg/mL in 25 mM HEPES pH 7.7 containing 67 µM EDTA). Foam collapse was complete after 30 seconds. Separately, a foam was prepared using the anionic detergent sodium dodecyl sulfate (SDS) (0.2 mg/mL in 25 mM HEPES pH 7.4 containing 67 µM EDTA). Foam collapse was essentially complete after 90 seconds. Separately, a foam was prepared using a mixture of peptide having SEQ ID NO:2 (0.05 mg/mL) and SDS (0.2 mg/mL), both in 25 mM HEPES pH 7.4 containing 67 µM EDTA. Foam stability was greatly enhanced in the mixture, with very little reduction in the height of the foam column at 10 minutes. $H_2SO_4$ was then added to reduce the solution pH to 3.6. A new foam prepared from the peptide solution adjusted to pH 3.6 showed a coarser structure and reduced stability, with foam thinning apparent at 120 seconds, although foam collapse was not complete at 5 minutes.

The disclosure of every patent, patent application and publication cited herein is hereby incorporated by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

REFERENCES

Andrews, M. J. I. and Tabor, A. B. 1999. *Forming stable helical peptides using natural and artificial amino acids*, Tetrahedron, 55, 11711-11743.

Ariga, K., Nakanishi, T., Hill, J. P., Shirai, M., Okuno, M., Abe, T. and Kikuchi, J. I. 2005. *Tunable pK of Amino Acid Residues at the Air-Water Interface Gives an L-zyme (Langmuir Enzyme)*, J. Am. Chem. Soc., 127, 12074-12080.

Arndt, K. M., Pelletier, J. N., Muller, K. M., Alber, T., Michnick, S. W. and Pluckthun, A. 2000. *A heterodimeric coiled-coil peptide pair selected in vivo from a designed library-versus-library ensemble*, J Mol Biol, 295, 627-639.

Arndt, K. M., Pelletier, J. N., Muller, K. M., Pluckthun, A. and Alber, T. 2002. *Comparison of in vivo selection and rational design of heterodimeric coiled coils*, Structure, 10, 1235-1248.

Benhar, I. 2001. *Biotechnological applications of phage and cell display*, Biotechnol Adv, 19, 1-33.

Boon, C. L., Frost, D. and Chakrabartty, A. 2004. *Identification of stable helical bundles from a combinatorial library of amphipathic peptides*, Biopolymers, 76, 244-257.

Bosshard, H. R., Marti, D. N. and Jelesarov, I. 2004. *Protein stabilization by salt bridges: concepts, experimental approaches and clarification of some misunderstandings*, J Mol Recognit, 17, 1-16.

Caessens, P., Daamen, W. F., Gruppen, H., Visser, S, and Voragen, A. G. J. 1999a. *beta-lactoglobulin hydrolysis. 2. Peptide identification, SH/SS exchange, and functional properties of hydrolysate fractions formed by the action of plasmin*, J. Agric. Food Chem., 47, 2980-2990.

Caessens, P., Visser, S., Gruppen, H. and Voragen, A. G. J. 1999b. *beta-lactoglobulin hydrolysis. 1. Peptide composition and functional properties of hydrolysates obtained by the action of plasmin, trypsin, and Staphylococcus aureus V8 protease*, J. Agric. Food Chem., 47, 2973-2979.

Cameron, D. R., Weber, M. E., Idziak, E. S., Neufeld, R. J. and Cooper, D. G. 1991. *Determination of interfacial areas in emulsions using turbidimetric and droplet size data: correction of the formula for emulsifying activity index*, J. Agric. Food Chem., 39, 655-659.

Cascao-Pereira, L. G., Hickel, A., Radke, C. J. and Blanch, H. W. 2003a. *Interfacial versus homogeneous enzymatic cleavage of mandelonitrile by hydroxynitrile lyase in a biphasic system*, Biotechnol. Bioeng., 83, 498-501.

Cascao-Pereira, L. G., Johansson, C., Radke, C. J. and Blanch, H. W. 2003b. *Surface forces and drainage kinetics of protein-stabilized aqueous films*, Langmuir, 19, 7503-7513.

Cascao-Pereira, L. G., Theodoly, O., Blanch, H. W. and Radke, C. J. 2003c. *Dilatational rheology of BSA conformers at the air/water interface*, Langmuir, 19, 2349-2356.

Cho, S. J., Zheng, W. F. and Tropsha, A. 1998. *Rational combinatorial library design. 2. Rational design of targeted combinatorial peptide libraries using chemical similarity probe and the inverse QSAR approaches*, J. Chem. Inf. Comput. Sci., 38, 259-268.

Cochran, D. A. E. and Doig, A. J. 2001. *Effect of the N2 residue on the stability of the alpha-helix for all 20 amino acids*, Protein Sci., 10, 1305-1311.

Cochran, D. A. E., Penel, S, and Doig, A. J. 2001. *Effect of the N1 residue on the stability of the alpha-helix for all 20 amino acids*, Protein Sci., 10, 463-470.

Cohen, C. and Parry, D. A. D. 1990. *α-Helical coiled coils and bundles: how to design an α-helical protein*, Proteins: Struct., Funct., Genet., 7, 1-15.

De Alba, E., Santoro, J., Rico, M. and Jimenez, M. A. 1999. *De novo design of a monomeric three-stranded antiparallel beta-sheet*, Protein Sci., 8, 854-865.

De Crescenzo, G., Litowski, J. R., Hodges, R. S, and O'Connor-McCourt, M. D. 2003. *Real-time monitoring of the interactions of two-stranded de novo designed coiled-coils: Effect of chain length on the kinetic and thermodynamic constants of binding*, Biochemistry, 42, 1754-1763.

DeGrado, W. F. 2001. *Introduction: Protein design*, Chem. Rev., 101, 3025-3026.

DeGrado, W. F., Schneider, J. P. and Hamuro, Y. 1999a. *The twists and turns of beta-peptides*, J Pept Res, 54, 206-217.

DeGrado, W. F., Summa, C. M., Pavone, V., Nastri, F. and Lombardi, A. 1999b. *De novo design and structural characterization of proteins and metalloproteins*, Annu Rev Biochem, 68, 779-819.

Dickinson, E., Murray, B. S, and Stainsby, G. 1988. *Coalescence Stability of Emulsion-Sized proplets at a Planar Oil-Water Interface and the Relationship to Protein Film Surface Rheology*, J. Chem. Soc., Faraday Trans. I, 84, 871-883.

Faergemand, M., Murray, B. S, and Dickinson, E. 1997. *Cross-linking of milk proteins with transglutaminase at the oil-water interface*, J. Agric. Food Chem., 45, 2514-2519.

Fairman, R., Chao, H. G., Lavoie, T. B., Villafranca, J. J., Matsueda, G. R. and Novotny, J. 1996. *Design of heterotetrameric coiled coils: Evidence for increased stabilization by Glu(-)-Lys(+) ion pair interactions*, Biochemistry, 35, 2824-2829.

Fairman, R., Chao, H. G., Mueller, L., Lavoie, T. B., Shen, L. Y., Novotny, J. and Matsueda, G. R. 1995. *Characterization of a new four-chain coiled-coil: influence of chain length on stability*, Protein Sci., 4, 1457-1469.

Fung, S. Y., Keyes, C., Duhamel, J. and Chen, P. 2003. *Concentration effect on the aggregation of a self-assembling oligopeptide*, Biophys J, 85, 537-548.

Gauthier, S. F., Paquin, P., Pouliot, Y. and Turgeon, S. 1993. *Surface-Activity and Related Functional-Properties of Peptides Obtained from Whey Proteins*, J Dairy Sci, 76, 321-328.

Girardet, J. M., Debomy, L., Courthaudon, J. L., Miclo, L., Humbert, G. and Gaillard, J. L. 2000. *Viscoelastic properties of oil-water interfaces covered by bovine beta-casein tryptic peptides*, J Dairy Sci, 83, 2410-2421.

Hill, R. B., Raleigh, D. P., Lombardi, A. and Degrado, N. F. 2000. *De novo design of helical bundles as models for understanding protein folding and function*, Acc. Chem. Res., 33, 745-754.

Hong, Y. S., Legge, R. L., Zhang, S, and Chen, P. 2003. *Effect of amino acid sequence and pH on nanofiber formation of self-assembling peptides EAK16-II and EAK16-IV*, Biomacromolecules, 4, 1433-1442.

Huang, X. L. L., Catignani, G. L. and Swaisgood, H. E. 1996. *Improved emulsifying properties of beta-barrel domain peptides obtained by membrane fractionation of a limited tryptic hydrolysate of beta-lactoglobulin*, J. Agric. Food Chem., 44, 3437-3443.

Huyghues Despointes, B. M. P. and Baldwin, R. L. 1997. *Ion-pair and charged hydrogen-bond interactions between histidine and aspartate in a peptide helix*, Biochemistry, 36, 1965-1970.

Jelesarov, I., Dun, E., Thomas, R. M. and Bosshard, H. R. 1998. *Salt effects on hydrophobic interaction and charge screening in the folding of a negatively charged peptide to a coiled coil (leucine zipper)*, Biochemistry, 37, 7539-7550.

Jones, D. B. and Middelberg, A. P. J. 2002a. *Direct determination of the mechanical properties of an interfacially adsorbed protein film*, Chem. Eng. Sci., 57, 1711-1722.

Jones, D. B. and Middelberg, A. P. J. 2002b. *Mechanical properties of interfacially adsorbed peptide networks*, Langmuir, 18, 10357-10362.

Jones, D. B. and Middelberg, A. P. J. 2002c. *Micromechanical testing of interfacial protein networks demonstrates ensemble behaviour characteristic of a nanostructured biomaterial*, Langmuir, 18, 5585-5591.

Jones, D. B. and Middelberg, A. P. J. 2003. *Interfacial protein networks and their impact on droplet breakup*, AIChE J., 49, 1533-1541.

Jones J, 1992, Amino Acid and Peptide Synthesis. Oxford Chemistry Primers, Oxford University Press.

Keith, A., Erbe, A., Dathe, M. and Blume, A. 2004. *Infrared reflection absorption spectroscopy of amphipathic model peptides at the air/water interface*, Biophys J, 86, 3750-3758.

Kohn, W. D. and Hodges, R. S. 1998. *De novo design of α-helical coiled coils and bundles: models for the development of protein-design principles*, Trends Biotechnol., 16, 379-389.

Kohn, W. D., Kay, C. M. and Hodges, R. S. 1997a. *Positional dependence of the effects of negatively charged Glu side chains on the stability of two-stranded alpha-helical coiled-coils*, J Pept Sci, 3, 209-223.

Kohn, W. D., Kay, C. M. and Hodges, R. S. 1997b. *Salt effects on protein stability: Two-stranded alpha-helical coiled-coils containing inter-or intrahelical ion pairs*, J Mol Biol, 267, 1039-1052.

Kohn, W. D., Monera, O. D., Kay, C. M. and Hodges, R. S. 1995. *The Effects of Interhelical Electrostatic Repulsions between Glutamic-Acid Residues in Controlling the Dimerization and Stability of 2-Stranded Alpha-Helical Coiled-Coils*, J Biol Chem, 270, 25495-25506.

Krylov, D., Barchi, J. and Vinson, C. 1998. *Inter-helical interactions in the leucine zipper coiled coil dimer: pH and salt dependence of coupling energy between charged amino acids*, J Mol Biol, 279, 959-972.

Kwok, S. C. and Hodges, R. S. 2004. *Effect of chain length on coiled-coil stability: Decreasing stability with increasing chain length*, Biopolymers, 76, 378-390.

Litowski, J. R. and Hodges, R. S. 2001. *Designing heterodimeric two-stranded alpha-helical coiled-coils: the effect of chain length on protein folding, stability and specificity*, J Pept Res, 58, 477-492.

Litowski, J. R. and Hodges, R. S. 2002. *Designing heterodimeric two-stranded alpha-helical coiled-coils—Effects of hydrophobicity and alpha-helical propensity on protein folding, stability, and specificity*, J Biol Chem, 277, 37272-37279.

Marti, D. N. and Bosshard, H. R. 2003. *Electrostatic interactions in leucine zippers: Thermodynamic analysis of the contributions of Glu and his residues and the effect of mutating salt bridges*, J Mol Biol, 330, 621-637.

Middelberg, A. P. J., Radke, C. J. and Blanch, H. W. 2000. *Peptide interfacial adsorption is kinetically limited by the thermodynamic stability of self association*, Proc. Natl. Acad. Sci. USA, 97, 5054-5059.

Mohammed, R. A., Bailey, Ad., Luckham, P. F. and Taylor, S. E. 1993. *Dewatering of Crude-Oil Emulsions 1. Rheological Behavior of the Crude-Oil Water Interface*, Colloids Surf., A, 80, 223-235.

Mucha, M., Frigato, T., Levering, L. M., Allen, H. C., Tobias, D. J., Dang, L. X. and Jungwirth, P. 2005. *Unified molecular picture of the surfaces of aqueous acid, base, and salt solutions*, J. Phys. Chem. B, 109, 7617-7623.

Rahali, V., Chobert, J. M., Haertle, T. and Gueguen, J. 2000. *Emulsification of chemical and enzymatic hydrolysates of beta-lactoglobulin: characterization of the peptides adsorbed at the interface*, Nahrung-Food, 44, 89-95.

Rapaport, H., Kjaer, K., Jensen, T. R., Leiserowitz, L. and Tirrell, D. A. 2000. *Two-dimensional order in beta-sheet peptide monolayers*, J. Am. Chem. Soc., 122, 12523-12529.

Rapaport, H., Moller, G., Knobler, C. M., Jensen, T. R., Kjaer, K., Leiserowitz, L. and Tinell, D. A. 2002. *Assembly of triple-stranded beta-sheet peptides at interfaces*, J. Am, Chem. Soc., 124, 9342-9343.

Rausch, J. M., Marks, J. R. and Wimley, W. C. 2005. *Rational combinatorial design of pore-forming beta-sheet peptides*, Proc. Natl. Acad. Sci. USA, 102, 10511-10515.

Regan, L. 1995. *Protein Design—Novel Metal-Binding Sites*, Trends Biochem Sci, 20, 280-285.

Sarikaya, M., Tamerler, C., Schwartz, D. T. and Baneyx, F. O. 2004. *Materials assembly and formation using engineered polypeptides*, Annu. Rev. Mater. Res., 34, 373-408.

Sneer, R., Weygand, M. J., Kjaer, K., Tirrell, D. A. and Rapaport, H. 2004. *Parallel beta-sheet assemblies at interfaces*, ChemPhysChem, 5, 747-750.

Su, J. Y., Hodges, R. S, and Kay, C. M. 1994. *Effect of Chain-Length on the Formation and Stability of Synthetic Alpha-Helical Coiled Coils*, Biochemistry, 33, 15501-15510.

Tamerler, C., Dincer, S., Heidel, D., Zareie, M. H. and Sarikaya, M. 2003. *Biomimetic multifunctional molecular coatings using engineered proteins*, Prog. Org. Coat., 47, 267-274.

van der Ven, C., Gruppen, H., de Bont, D. B. A. and Voragen, A. G. J. 2001. *Emulsion properties of casein and whey protein hydrolysates and the relation with other hydrolysate characteristics*, J. Agric. Food Chem., 49, 5005-5012.

van der Ven, C., Gruppen, H., de Bont, D. B. A. and Voragen, A. G. J. 2002. *Correlations between biochemical characteristics and foam-forming and -stabilizing ability of whey and casein hydrolysates*, J. Agric. Food Chem., 50, 2938-2946.

Vu, C., Robblee, J., Werner, K. M. and Fairman, R. 2001. *Effects of charged amino acids at b and c heptad positions on specificity and stability of four-chain coiled coils*, Protein Sci., 10, 631-637.

Wang, K., Keasling, J. D. and Muller, S. J. 2005. *Effects of the sequence and size of non-polar residues on self-assembly of amphiphilic peptides*, Int J Biol Macromol, 36, 232-240.

Wang, T., Zhu, Y. J., Getahun, Z., Du, D. G., Huang, C. Y., DeGrado, W. F. and Gai, F. 2004. *Length dependent helix-coil transition kinetics of nine alanine-based peptides*, J. Phys. Chem. B, 108, 15301-15310.

Williams, A., Janssen, J. J. M. and Prins, A. 1997. *Behaviour of droplets in simple shear flow in the presence of a protein emulsifier*, Colloids Surf., A, 125, 189-200.

Xu, G. F., Wang, W. X., Groves, J. T. and Hecht, M.H.2001. *Self-assembled monolayers from a designed combinatorial library of de novo beta-sheet proteins*, Proc. Natl. Acad. Sci. USA, 98, 3652-3657.

Xu, Z., Brauner, J. W., Flach, C. R. and Mendelsohn, R. 2004. *Orientation of peptides in aqueous monolayer films. Infrared reflection-absorption spectroscopy studies of a synthetic amphipathic beta-sheet*, Langmuir, 20, 3730-3733.

Yu, Y., Monera, O. D., Hodges, R. S, and Privalov, P. L. 1996. *Ion pairs significantly stabilize coiled-coils in the absence of electrolyte*, J Mol Biol, 255, 367-372.

Zhang, S. G. and Altman, M. 1999. *Peptide self-assembly in functional polymer science and engineering*, React. Funct. Polym., 41, 91-102.

What is claimed is:

1. A peptide selected from the group consisting of:

SEQ ID NO: 2    Ac-MKQLADSLHQLARQVSRLEHA-CONH$_2$

SEQ ID NO: 4    Ac-MKELADSLMQLARQVDRLESA-CONH$_2$

SEQ ID NO: 5    Ac-MKQLADSLHQLAHQVSHLEHA-CONH$_2$.

2. A self-assembled, force-transmitting peptide network formed at a fluid-fluid interface wherein the peptide network comprises peptides comprising the amino acid sequence of SEQ ID NO: 2, SEQ ID NO: 4, or SEQ ID NO: 5 and that interact with one another and that have an affinity for the fluid-fluid interface and wherein the force transmission of the peptide network is manipulable by exposure to a stimulus which alters the physical and/or chemical properties of the peptide, wherein the stimulus is selected from the group consisting of an acid, a base, a metal ion, a chelating agent, an organic counterion, an inorganic counterion, a chaotropic agent, a salt, temperature, and mixtures thereof.

3. The self-assembled, force-transmitting peptide network according to claim 2 wherein the peptides in the peptide network have an amphipathic structure.

4. The self-assembled, force-transmitting peptide network according to claim 3 wherein the amphipathic structure is ordered.

5. The self-assembled, force-transmitting peptide network according to claim 4 wherein the ordered amphipathic structure is an α-helix or a β-sheet.

6. The self-assembled, force-transmitting peptide network according to claim 2 wherein the peptides in the peptide network interact with one another by one or more of ion-pair interactions, dipole interactions, salt bridge formation, hydrogen bonding, short range solvation forces, hydrophobic interactions, osmotic attractive potential, metal ion bridging and surface charge interactions.

7. The self-assembled, force-transmitting peptide network according to claim 2 wherein the stimulus which alters the chemical and/or physical properties of the peptide alters at least one of
i) the ability of peptides within the peptide network to participate in intermolecular interactions,
ii) stabilization or destabilization of the conformation of a peptide with a network,
iii) increasing or reducing the affinity of a peptide for the fluid-fluid interface, or
iv) the rate of formation of the peptide network.

8. A foam comprising a self-assembled, force-transmitting peptide network formed at a fluid-fluid interface wherein the peptide network comprises peptides comprising the amino acid sequence of SEQ ID NO: 2, SEQ ID NO: 4, or SEQ ID NO: 5 and that interact with one another and that have an affinity for the fluid-fluid interface and wherein the force transmission of the peptide network is manipulable by exposure to a stimulus which alters the chemical and/or physical properties of the peptide, wherein the stimulus is selected from the group consisting of an acid, a base, a metal ion, a chelating agent, an organic counterion, an inorganic counterion, an oxidizing agent, a reducing agent, a chaotropic agent, a salt, temperature, and mixtures thereof.

9. An oil-in-water emulsion comprising a self-assembled, force-transmitting peptide network formed at a fluid-fluid interface wherein the peptide network comprises peptides comprising the amino acid sequence of SEQ ID NO: 2, SEQ ID NO: 4, or SEQ ID NO: 5 and that interact with one another and that have an affinity for the fluid-fluid interface and wherein the force transmission of the peptide network is manipulable by exposure to a stimulus which alters the chemical and/or physical properties of the peptide, wherein the stimulus is selected from the group consisting of an acid, a base, a metal ion, a chelating agent, an organic counterion, an inorganic counterion, an oxidizing agent, a reducing agent, a chaotropic agent, a salt, temperature, and mixtures thereof.

10. A method of modulating interfacial characteristics in a self-assembled, force-transmitting peptide network at a fluid-fluid interface comprising exposing a peptide capable of participating in a self-assembled, force-transmitting peptide network, either before or after it interacts with other peptides to form the peptide network, to a stimulus that alters the chemical and/or physical properties of the peptide, wherein the stimulus is selected from the group consisting of an acid, a base, a metal ion, a chelating agent, an organic counterion, an inorganic counterion, a chaotropic agent, a salt, temperature and mixtures thereof wherein the peptide comprises the amino acid sequence of SEQ ID NO: 2, SEQ ID NO: 4, or SEQ ID NO: 5.

11. A method according to claim 10 wherein the interfacial characteristic modulated is the ability of the peptide network to transmit force.

12. A method according to claim 10 wherein the stimulus results in the formation of a stable peptide network.

13. A method according to claim 10 wherein the stimulus results in the destabilization or dissipation of a peptide network.

14. A method according to claim 10 wherein the stimulus which alters the chemical and/or physical properties of the peptide alters at least one of
i) the ability of peptides within the peptide network to participate in intermolecular interactions,
ii) stabilization or destabilization of the conformation of a peptide with a network,
iii) increasing or reducing the affinity of a peptide for the fluid-fluid interface, or
iv) the rate of formation of the peptide network.

15. A method according to claim 10 wherein the stimulus which alters the chemical and/or physical properties of the peptide acts by removing a stimulus present or previously introduced into contact with the peptide network.

16. A method of modulating interfacial characteristics in a self-assembled, force transmitting peptide network at a fluid-fluid interface comprising the steps of:
i) exposing a peptide capable of participating in a self-assembled, force-transmitting peptide network, either before or after it interacts with other peptides to form the peptide network, to a first stimulus that alters the chemical and/or physical properties of the peptide at a first time; and
ii) exposing the peptide to a second stimulus that alters the chemical and/or physical properties of the peptide adopted upon exposure to the first stimulus at a second time;

wherein the first and second stimulus are independently selected from the group consisting of an acid, a base, a metal ion, a chelating agent, an organic counterion, an inorganic counterion, an oxidizing agent, a reducing agent, a chaotropic agent, a salt, temperature, and mixtures thereof, wherein the peptide comprises the amino acid sequence of SEQ ID NO: 2, SEQ ID NO: 4, or SEQ ID NO: 5.

17. A method according to claim 16 wherein the first stimulus causes formation or strengthening of a peptide network and the second stimulus causes a reduction in the strength or the dissipation of the peptide network formed or strengthened upon exposure to the first stimulus.

18. A method according to claim 16 wherein the first stimulus prevents the formation of or reduces the rate of formation of a peptide network and the second stimulus enhances formation of a peptide network at the fluid-fluid interface.

19. A method according to claim 16 wherein steps i) and/or ii) are repeated one or more times.

20. A method according to claim 16 wherein the interfacial characteristic that is modulated is the ability of the peptide network to transmit force.

21. A method of modulating interfacial characteristics in a self-assembled, force-transmitting peptide network at a fluid-fluid interface comprising exposing a peptide capable of participating in a self-assembled, force-transmitting peptide network, either before or after it interacts with other peptides to form the peptide network, to a stimulus that alters the chemical and/or physical properties of the peptide, wherein the peptide capable of participating in a self-assembled, force-transmitting peptide network is selected from the group consisting of:

```
SEQ ID NO: 2  Ac-MKQLADSLHQLARQVSRLEHA-CONH2
SEQ ID NO: 4  Ac-MKELADSLMQLARQVDRLESA-CONH2
SEQ ID NO: 5  Ac-MKQLADSLHQLAHQVSHLEHA-CONH2,
```

22. A method of modulating the formation of a peptide network at a fluid-fluid interface comprising exposing peptides capable of participating in a self-assembled, force-transmitting peptide network to a first condition or to a second condition, wherein under the first condition individual peptides have a first chemical and/or physical property that causes the peptides to interact with one another to thereby form the network and wherein under the second condition individual peptides have a second physical and/or chemical property that causes the peptides to separate thereby dissipating the network, wherein the first and second condition are provided by addition of a stimulus selected from the group consisting of an acid, a base, a metal ion, a chelating agent, an organic counterion, an inorganic counterion, a chaotropic agent, a salt, temperature, and mixtures thereof, wherein the peptide comprises the amino acid sequence of SEQ ID NO: 2, SEQ ID NO: 4, or SEQ ID NO: 5.

23. A method of modulating the stability of a foam comprising a self-assembled, force-transmitting peptide network at a liquid-gas interface; said method comprising
i) exposing the liquid-gas interface to a first stimulus that alters the chemical and/or physical properties of a peptide in the peptide network at a first time; and
ii) exposing the liquid-gas interface to a second stimulus that alters the chemical and/or physical properties of the peptide in the peptide network adopted upon exposure to the first stimulus at a second time;
wherein the first and second stimulus are independently selected from the group consisting of an acid, a base, a metal ion, a chelating agent, an organic counterion, an inorganic counterion, an oxidizing agent, a reducing agent, a chaotropic agent, a salt, temperature, and mixtures thereof, wherein the peptide comprises the amino acid sequence of SEQ ID NO: 2, SEQ ID NO: 4, or SEQ ID NO: 5.

24. A method according to claim 23 wherein the first stimulus allows formation of the peptide network, increases the rate of formation of the peptide network or increases force transmission of the peptide network and the second stimulus causes a reduction in force transmission of the peptide network or abolition of force transmission by the peptide network.

25. A method according to claim 24 wherein the second stimulus causes collapse of the foam.

26. A method according to claim 23 wherein the first stimulus reduces the force transmission of the peptide network and the second stimulus increases the force transmission of the peptide network.

27. A method according to claim 23 wherein steps i) and/or ii) are repeated one or more times.

28. A method of modulating the stability of an emulsion comprising a self-assembled, force-transmitting peptide network at a liquid-liquid interface; said method comprising:
ia) exposing the liquid-liquid interface to a first stimulus that alters the chemical and/or physical properties of a peptide in the peptide network at a first time; and
iia) exposing the liquid-liquid interface to a second stimulus that alters the chemical and/or physical properties of the peptide in the peptide network adopted upon exposure to the first stimulus at a second time;
wherein the first and second stimulus are independently selected from the group consisting of an acid, a base, a metal ion, a chelating agent, an organic counterion, an inorganic counterion, an oxidizing agent, a reducing agent, a chaotropic agent, a salt, temperature, and mixtures thereof, wherein the peptide comprises the amino acid sequence of SEQ ID NO: 2, SEQ ID NO: 4, or SEQ ID NO: 5.

29. A method according to claim 28 wherein the first stimulus allows formation of the peptide network, increases the rate of formation of the peptide network or increases force transmission of the peptide network and the second stimulus causes a reduction in force transmission of the peptide network or abolition of force transmission by the peptide network.

30. A method according to claim 29 wherein the second stimulus causes coalescence of the emulsion.

31. A method according to claim 28 wherein the first stimulus reduces the force transmission of the peptide network and the second stimulus increases the force transmission of the peptide network.

* * * * *

UNITED STATES PATENT AND TRADEMARK OFFICE
CERTIFICATE OF CORRECTION

| | | |
|---|---|---|
| PATENT NO. | : 8,039,582 B2 | |
| APPLICATION NO. | : 11/817144 | |
| DATED | : October 18, 2011 | |
| INVENTOR(S) | : Anton Peter Jacob Middelberg et al. | |

It is certified that error appears in the above-identified patent and that said Letters Patent is hereby corrected as shown below:

In column 1 (page 2 item 56) at line 67, Under Other Publications, Change "(AlChE)" to --(AIChE)--.

In column 14 at line 33 (approx), Change "L-N-methylisolleucine" to --L-N-methylisoleucine--.

In column 14 at line 71 (approx), Change "N-cyclododeclglycine" to --N-cyclododecylglycine--.

In column 15 at line 4 (approx), Change "D-N-methylasparatate" to --D-N-methylaspartate--.

In column 15 at line 7 (approx), Change "N-(1-hydroxyethy)glycine" to --N-(1-hydroxyethyl)glycine--.

In column 15 at line 8 (approx), Change "N-(hydroxyethy)glycine" to --N-(hydroxyethyl)glycine--.

In column 15 at line 18 (approx), Change "Nva" to --Nval--.

In column 15 at line 37 (approx), Change "Mtrp" to --Mval--.

In column 20 at line 13, Change "al," to --al.,--.

In column 20 at line 13, Change "at," to --al.,--.

In column 20 at line 38, Change "peptides)" to --peptides--.

In column 24 at line 42, Change "(abcdefg)" to --(abcdefg)$_n$--.

In column 35 at line 15, Change "peptides," to --peptides.--.

In column 50 at line 20 (approx), Change "Ac-PFFSFHFSP-CONH$_2$" to --Ac-PHFSFHFSP-CONH$_2$--.

In column 59 at line 7 (approx), Change "Ac-PFFSFHFSP-CONH$_2$" to --Ac-PHFSFHFSP-CONH$_2$--.

Signed and Sealed this
Fifteenth Day of January, 2013

David J. Kappos
*Director of the United States Patent and Trademark Office*

CERTIFICATE OF CORRECTION (continued)

U.S. Pat. No. 8,039,582 B2

In column 60 at lines 20-38, Delete "Peptide having ..... were present." and insert the same on Col. 60, Line 19, after "tensiometry" as a continuation of the same Paragraph.

In column 60 at line 32, Change "prop" to --Drop--.

In column 72 at line 39, Change "200 M" to --200 μM--.

In column 73 at line 55, Change "15 mM." to --15 min.--.

In column 73 at line 62 (approx), Change "Ni(H)" to --Ni(II)--.

In column 75 at line 21 (approx), Change "NaOH." to --NaOH,--.

In column 76 at line 13 (approx), Change "20 mM." to --20 min.--.

In column 76 at line 27, Change "30 mM." to --30 min.--.

In column 76 at line 41 (approx), Change "8 mM." to --8 min.--.

In column 87 at line 23, Change "Dun," to --Durr,--.

In column 87 at line 43, Change "Keith," to --Kerth,--.

In column 88 at line 21, Change "Ad.," to --A.I.,--.

In column 88 at line 38, Change "Tinell," to --Tirrell,--.

In column 95 at line 14 (approx), In Claim 1, change "$CONH_2$" to --$CONH_2$,--.

In column 95 at line 15 (approx), In Claim 1, change "$CONH_2$" to --$CONH_2$,--.

In column 96 at line 32, In Claim 10, change "thereof" to --thereof,--.

In column 97 at line 35 (approx), In Claim 21, change "$CONH_2$" to --$CONH_2$,--.

In column 97 at line 36 (approx), In Claim 21, change "$CONH_2$" to --$CONH_2$,--.

In column 97 at line 37 (approx), In Claim 21, change "$CONH_2$," to --$CONH_2$.--.